(12) United States Patent
Budyansky et al.

(10) Patent No.: US 11,801,060 B2
(45) Date of Patent: Oct. 31, 2023

(54) SYSTEMS AND METHODS FOR BONE AND TISSUE HARVESTING

(71) Applicant: Avitus Orthopaedics, Inc., Farmington, CT (US)

(72) Inventors: Maxim Budyansky, Farmington, CT (US); Neil Shah, Farmington, CT (US); Christopher Chiang, Baltimore, MD (US); Brandon Craft, Edgewater, MD (US); Paul Fearis, Owings Mills, MD (US); Edward Land, Owings Mills, MD (US); Douglas Pattison, East Hartford, CT (US); Marton Varady, Baltimore, MD (US); Charles R. Satti, III, Branford, CT (US)

(73) Assignee: Avitus Orthopaedics, Inc., Shelton, CT (US)

( * ) Notice: Subject to any disclaimer, the term of this patent is extended or adjusted under 35 U.S.C. 154(b) by 0 days.

(21) Appl. No.: 15/572,267

(22) PCT Filed: May 9, 2016

(86) PCT No.: PCT/US2016/031503
§ 371 (c)(1),
(2) Date: Nov. 7, 2017

(87) PCT Pub. No.: WO2016/179594
PCT Pub. Date: Nov. 10, 2016

(65) Prior Publication Data
US 2018/0147071 A1      May 31, 2018

Related U.S. Application Data

(60) Provisional application No. 62/158,226, filed on May 7, 2015.

(51) Int. Cl.
*A61M 1/00* (2006.01)
*A61B 10/02* (2006.01)
(Continued)

(52) U.S. Cl.
CPC ...... *A61B 17/1635* (2013.01); *A61B 17/1642* (2013.01); *A61B 17/3472* (2013.01);
(Continued)

(58) Field of Classification Search
CPC .......... A61B 17/1635; A61B 2217/005; A61B 10/0096; A61B 10/0283; A61M 1/0062;
(Continued)

(56) References Cited

U.S. PATENT DOCUMENTS 1,685,655 A * 9/1928 Wenzka ............... B01D 29/902
                                                    210/120
1,941,982 A * 1/1934 Gill ........................ B01D 35/04
                                                    210/233
(Continued)

FOREIGN PATENT DOCUMENTS

RU         2223056 C2    2/2004
RU          65382 U1     8/2007
(Continued)

OTHER PUBLICATIONS

PCT International Search Report and Written Opinion for PCT/US2013/032531 dated Jun. 3, 2013.
(Continued)

*Primary Examiner* — David W Bates
(74) *Attorney, Agent, or Firm* — McCarter & English, LLP

(57) ABSTRACT

Tools, devices and systems that include a generally cylindrical, hollow shaft, and a suction canister are provided with advantageous interconnectivity features and functions that enable ease of manufacturing, lowered manufacturing costs,
(Continued)

and allow for a platform of different shaft embodiments and canister embodiments that may be manufactured in different combinations to form an array of unique instruments. The interconnectivity may be irreversible or reversible, and the connection features maintain an air tight seal between the components. Tools, devices and systems are also provided that include collection functionality that can be employed to manipulate the volume of tissue collected while using a tissue collection feature/function. This may be undertaken to restrict total volume of the collection chamber in a way that allows for continuous suction flow rate to take place while collecting the desired amount of tissue. Containing the tissue to a pre-set volume can enable a user to effectively ascertain the volume of tissue collected.

22 Claims, 73 Drawing Sheets

(51) Int. Cl.
| | |
|---|---|
| *A61B 17/16* | (2006.01) |
| *A61B 17/34* | (2006.01) |
| *A61F 2/46* | (2006.01) |
| *A61B 17/00* | (2006.01) |
| *A61B 17/3207* | (2006.01) |
| *A61B 17/32* | (2006.01) |
| *A61F 2/28* | (2006.01) |

(52) U.S. Cl.
CPC .............. *A61F 2/4644* (2013.01); *A61M 1/60* (2021.05); *A61M 1/772* (2021.05); *A61M 1/79* (2021.05); *A61B 10/02* (2013.01); *A61B 17/1631* (2013.01); *A61B 17/1633* (2013.01); *A61B 17/320708* (2013.01); *A61B 2017/00477* (2013.01); *A61B 2017/00876* (2013.01); *A61B 2017/00969* (2013.01); *A61B 2017/320008* (2013.01); *A61B 2017/320064* (2013.01); *A61B 2217/005* (2013.01); *A61F 2002/2835* (2013.01); *A61F 2002/4649* (2013.01); *A61M 2202/10* (2013.01); *A61M 2205/123* (2013.01); *A61M 2205/583* (2013.01)

(58) Field of Classification Search
CPC ...... A61M 1/0003; A61M 1/79; A61M 1/774; A61M 1/76; B01D 2201/24; B01D 2201/26; B01D 35/16; B01D 2201/02; B01D 2201/0423; B01D 29/96; A61C 17/065
See application file for complete search history.

(56) References Cited

U.S. PATENT DOCUMENTS

| | | | | |
|---|---|---|---|---|
| 2,689,048 A * | 9/1954 | Powers | ............... | B01D 35/30 210/457 |
| 3,889,657 A * | 6/1975 | Baumgarten | ........... | A61M 1/79 606/119 |
| 3,929,133 A * | 12/1975 | Ragab | ............... | A61B 17/42 604/246 |
| 4,468,217 A * | 8/1984 | Kuzmick | ............... | A61M 1/76 433/92 |
| 4,654,141 A * | 3/1987 | Frentzel | ............... | E04H 4/1681 210/232 |
| 4,675,110 A * | 6/1987 | Fay | ............... | B01D 36/001 210/453 |
| 4,801,292 A * | 1/1989 | Watson | ............... | A61M 3/0229 604/185 |
| 4,850,964 A * | 7/1989 | Cotter | ............... | A61M 1/0001 604/319 |
| 4,870,975 A | 10/1989 | Cronk et al. | | |
| 4,886,492 A * | 12/1989 | Brooke | ............... | A61M 1/79 604/902 |
| 5,049,136 A | 9/1991 | Johnson | | |
| 5,195,427 A | 3/1993 | Germano | | |
| 5,202,020 A * | 4/1993 | Desjoyaux | ............. | B01D 29/35 4/490 |
| 5,269,785 A * | 12/1993 | Bonutti | ............... | A61B 10/025 606/167 |
| 5,338,294 A * | 8/1994 | Blake, III | ............. | A61M 1/772 604/38 |
| 5,464,397 A * | 11/1995 | Powers Jr. | ............. | A61M 1/76 433/95 |
| 5,482,624 A * | 1/1996 | Swiatek | ................. | B01D 29/39 210/323.1 |
| 5,567,310 A * | 10/1996 | Nakashima | ........... | B01D 29/01 210/357 |
| 5,571,412 A * | 11/1996 | Nerli | ..................... | A61C 17/065 210/DIG. 17 |
| 5,593,578 A * | 1/1997 | Bryan | ................. | B01D 29/902 210/450 |
| 5,630,939 A * | 5/1997 | Bulard | ................... | B01D 35/02 433/92 |
| 5,766,134 A * | 6/1998 | Lisak | ................... | A61B 10/025 604/320 |
| 5,817,032 A * | 10/1998 | Williamson, IV | ........................ | A61B 10/0096 600/562 |
| 5,868,701 A * | 2/1999 | Powers, Jr. | ............. | F16K 15/00 604/28 |
| 5,954,961 A * | 9/1999 | Carchidi | ............... | B01D 35/02 210/455 |
| 6,083,175 A * | 7/2000 | Lundgren | ............. | B01D 29/23 600/573 |
| 6,139,509 A | 10/2000 | Yuan et al. | | |
| 6,299,763 B1 * | 10/2001 | Ashman | ............... | A61M 1/3633 210/450 |
| 6,406,454 B1 * | 6/2002 | Hajianpour | ............ | A61M 1/84 604/48 |
| 6,478,957 B1 * | 11/2002 | Terry, III | ............... | B01D 29/56 210/337 |
| 6,554,803 B1 * | 4/2003 | Ashman | ................ | A61M 37/00 433/89 |
| 6,592,756 B1 * | 7/2003 | Felix, Jr. | ................... | E04H 4/14 210/477 |
| 6,602,408 B1 * | 8/2003 | Berkey | ................ | B01D 35/027 210/477 |
| 6,908,455 B2 * | 6/2005 | Hajianpour | ............. | A61M 1/84 604/266 |
| 7,214,059 B2 * | 5/2007 | Takahashi | ............... | A61C 17/08 433/91 |
| 7,270,284 B2 * | 9/2007 | Liao | ........................ | C12M 45/02 241/2 |
| 7,556,622 B2 * | 7/2009 | Mark | .................. | A61B 10/0275 210/348 |
| 7,637,872 B1 | 12/2009 | Fox et al. | | |
| 8,430,880 B2 * | 4/2013 | Gil | ..................... | A61B 17/1635 30/282 |
| 8,491,497 B2 * | 7/2013 | Houser | .................. | C12M 45/02 241/69 |
| 8,815,099 B1 * | 8/2014 | Dubois | .................. | A61M 1/79 210/488 |
| 8,840,614 B2 * | 9/2014 | Mikhail | ................. | A61F 2/4644 606/86 R |
| 9,777,257 B2 * | 10/2017 | Howard | ............... | C12N 5/0653 |
| 10,172,983 B2 * | 1/2019 | Beer | ........................ | A61M 1/76 |
| 10,201,331 B2 * | 2/2019 | Fleming | ................... | G01N 1/00 |
| 10,822,248 B1 * | 11/2020 | Wagner | ................... | B05B 17/08 |
| 2002/0177785 A1 * | 11/2002 | Brannon | ........... | A61B 5/150755 600/562 |
| 2003/0078586 A1 | 4/2003 | Shapira | | |
| 2004/0082915 A1 | 4/2004 | Kadan | | |
| 2004/0115590 A1 * | 6/2004 | Takahashi | ............ | A61C 17/065 433/92 |
| 2004/0124129 A1 * | 7/2004 | Booth | ................. | B01D 29/96 210/450 |

(56) References Cited

U.S. PATENT DOCUMENTS

| | | | |
|---|---|---|---|
| 2004/0193071 A1* | 9/2004 | Binette | A61F 2/4644 |
| | | | 600/562 |
| 2005/0105385 A1* | 5/2005 | McGill | A61B 17/8805 |
| | | | 366/139 |
| 2005/0199560 A1* | 9/2005 | Jagt | C22B 9/023 |
| | | | 210/791 |
| 2005/0234408 A1 | 10/2005 | Chong et al. | |
| 2006/0106353 A1* | 5/2006 | Geneve | A61C 1/0076 |
| | | | 604/319 |
| 2006/0213374 A1* | 9/2006 | Shippert | A61M 1/0062 |
| | | | 99/472 |
| 2006/0229556 A1 | 10/2006 | Pressly, Sr. et al. | |
| 2006/0287579 A1* | 12/2006 | Okada | A61B 10/06 |
| | | | 600/156 |
| 2007/0055264 A1 | 3/2007 | Parmigiani | |
| 2007/0055282 A1* | 3/2007 | Muschler | A61B 17/32002 |
| | | | 606/92 |
| 2007/0227959 A1* | 10/2007 | Sinur | B01D 29/96 |
| | | | 210/232 |
| 2007/0270771 A1 | 11/2007 | Ralph et al. | |
| 2008/0119881 A1* | 5/2008 | Vetter | A61B 10/0041 |
| | | | 606/170 |
| 2009/0227893 A1* | 9/2009 | Coonahan | A61B 10/0283 |
| | | | 600/566 |
| 2009/0306669 A1* | 12/2009 | Takahashi | A61C 17/08 |
| | | | 606/80 |
| 2010/0016878 A1 | 1/2010 | Smith | |
| 2011/0213336 A1 | 9/2011 | Cucin | |
| 2011/0306951 A1 | 12/2011 | Marler | |
| 2013/0237843 A1* | 9/2013 | Linares | A61B 17/1606 |
| | | | 600/476 |
| 2014/0017771 A1* | 1/2014 | Mark | A01N 1/0263 |
| | | | 435/284.1 |
| 2014/0336599 A1* | 11/2014 | Patel | A61M 1/79 |
| | | | 604/319 |
| 2015/0045799 A1* | 2/2015 | Budyansky | A61B 17/32053 |
| | | | 606/84 |
| 2016/0184744 A1 | 6/2016 | Jakop | |
| 2017/0311935 A1* | 11/2017 | Choung | A61B 10/0275 |
| 2018/0001234 A1* | 1/2018 | Wildermuth | B01D 29/11 |
| 2018/0344327 A1* | 12/2018 | Jeng | A61B 10/025 |
| 2019/0142395 A1* | 5/2019 | Bartelucci | B01L 3/502 |
| | | | 422/536 |
| 2019/0381224 A1* | 12/2019 | Jaeger | A61M 1/0056 |
| 2020/0163657 A1* | 5/2020 | Stuba | A61B 10/02 |

FOREIGN PATENT DOCUMENTS

| | | |
|---|---|---|
| WO | WO 97/16118 A1 | 5/1997 |
| WO | WO 2007/057928 A1 | 5/2007 |
| WO | WO 2009/149250 A1 | 12/2009 |
| WO | WO 2012/037552 A2 | 3/2012 |

OTHER PUBLICATIONS

PCT International Search Report and Written Opinion for PCT/US2016/031503 dated Aug. 13, 2016.
U.S. Appl. No. 61/6640,313, filed Apr. 30, 2012.
PCT/US2013/032531, Mar. 15, 2013, WO 2013/165616.
U.S. Appl. No. 62/158,226, filed May 7, 2015.
PCT/US2016/31503, May 9, 2016, WO 2016/179594.
Extended European Search Report for EP 16790234.5 dated Jan. 2, 2019.
DuPuy Synthes part of the Johnson & Johnson family of companies, For Intramedullary Reaming and Bone Harvesting: Reamer/Irrigator/Aspirator (RIA) Surgical Technique, ps 1-35, 2015-2017.
Non-Final Office Action U.S. Appl. No. 15/896,450 dated Jan. 24, 2020.

* cited by examiner

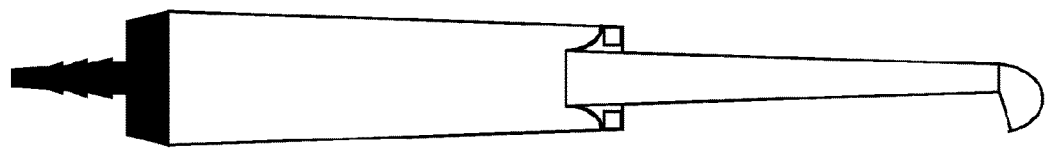
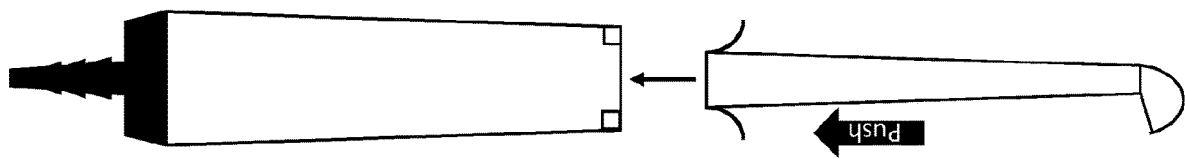
Snap-Fit Connection
Figure 3

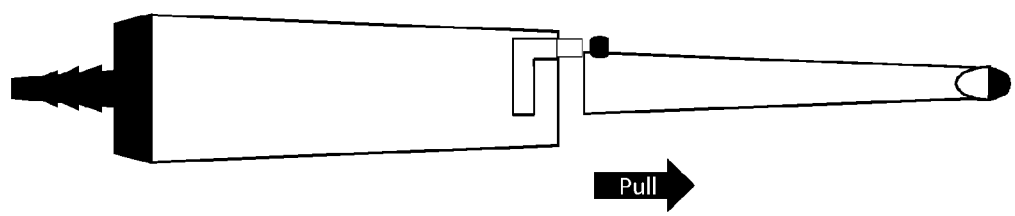
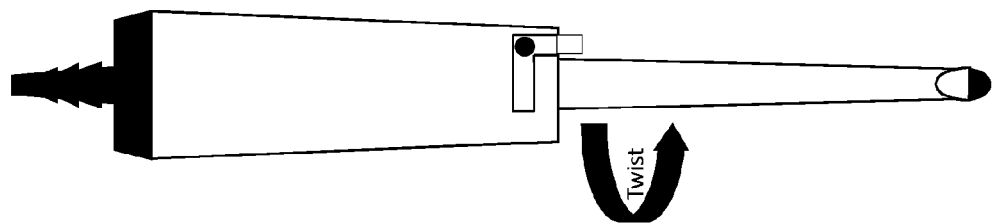
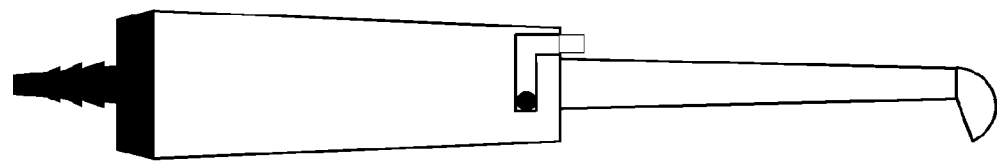
Slotted-Gate and Pin
Figure 6a

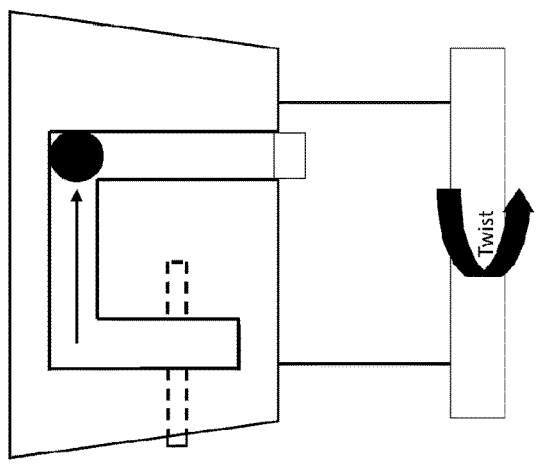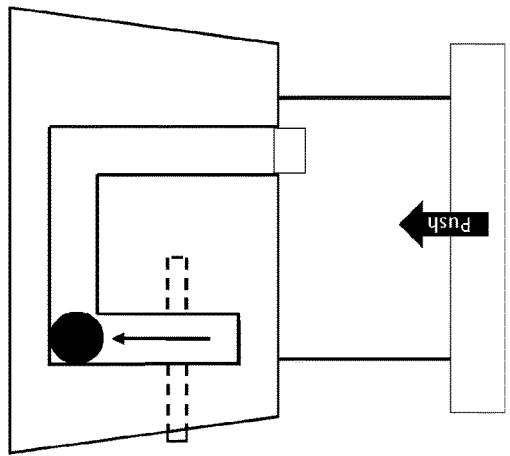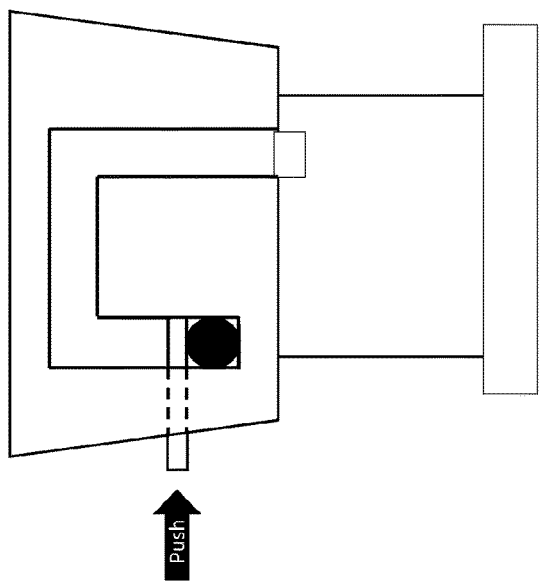
Figure 6b

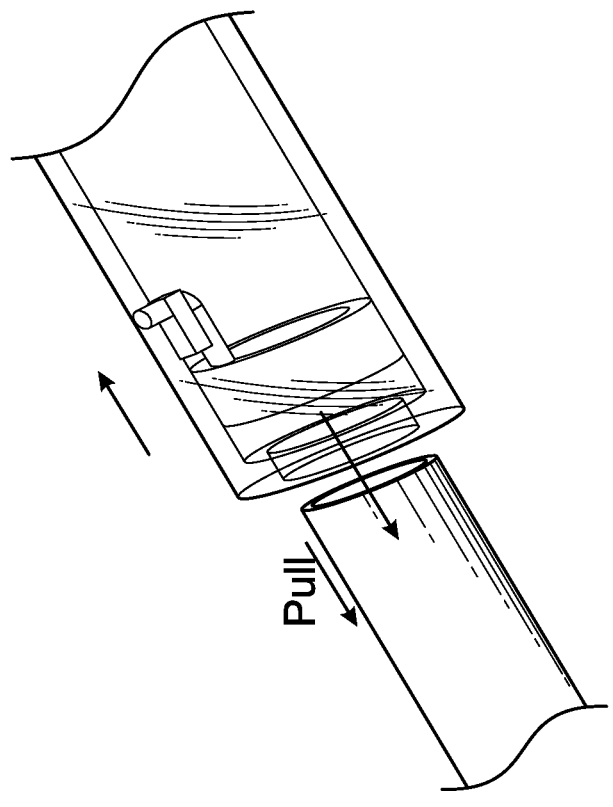
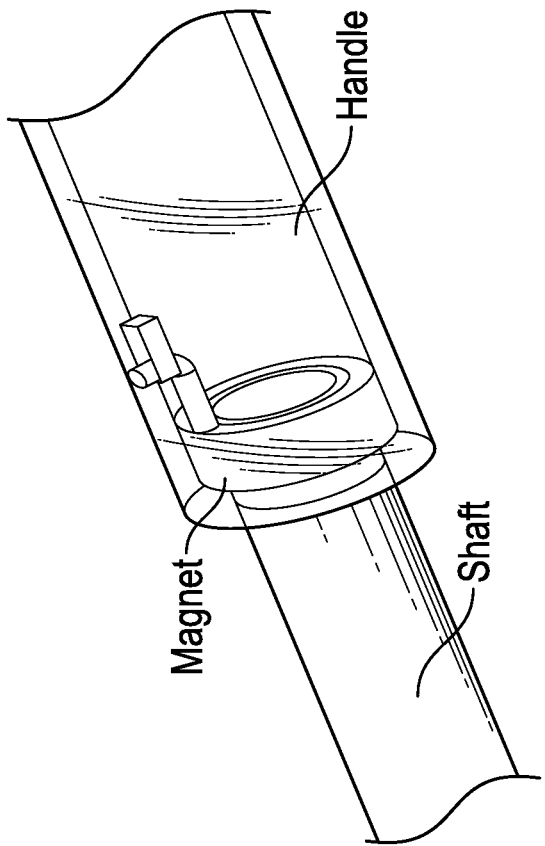
FIG. 7A

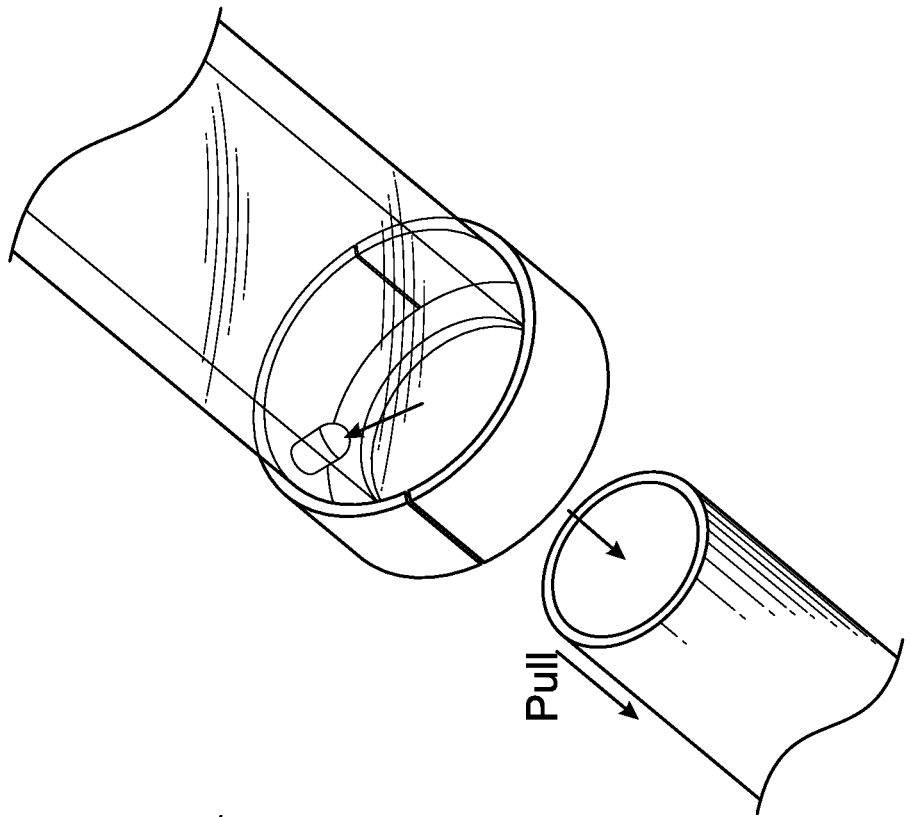
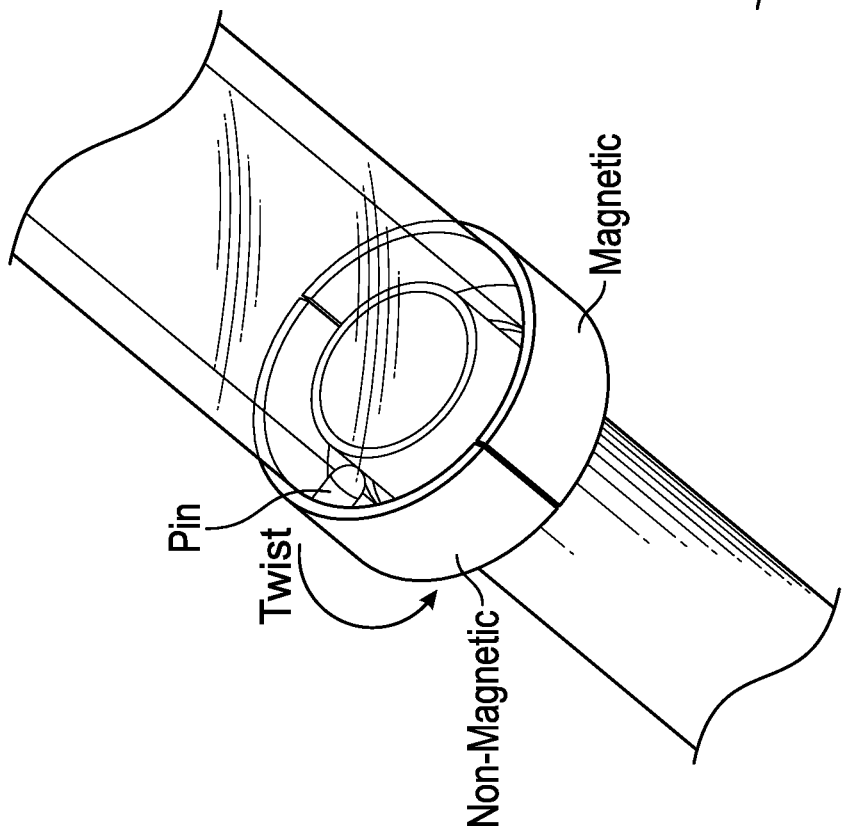
FIG. 7B

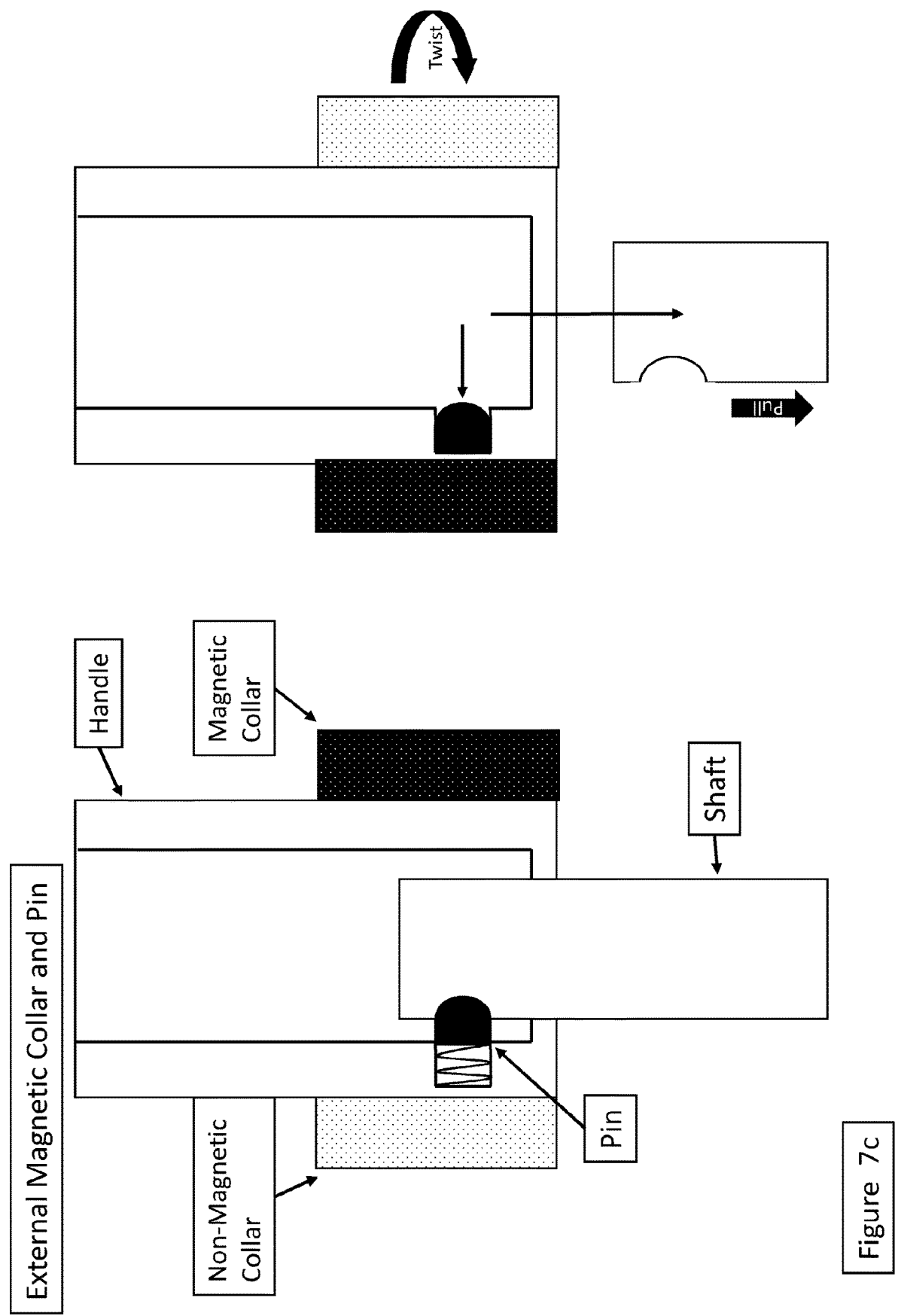

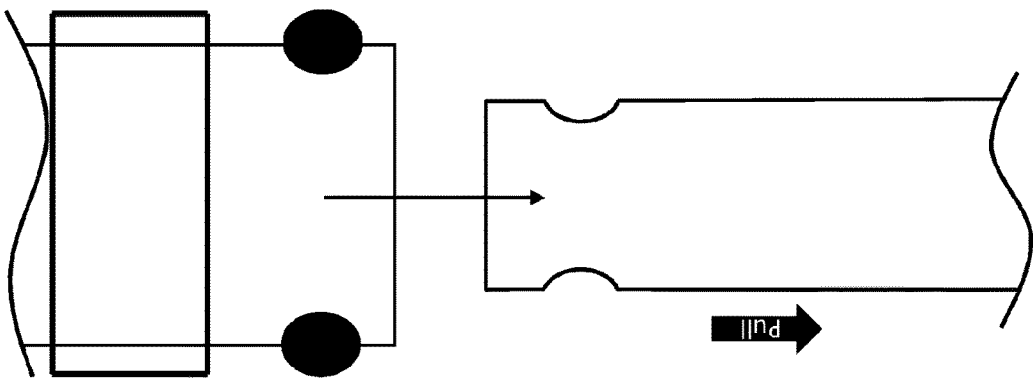
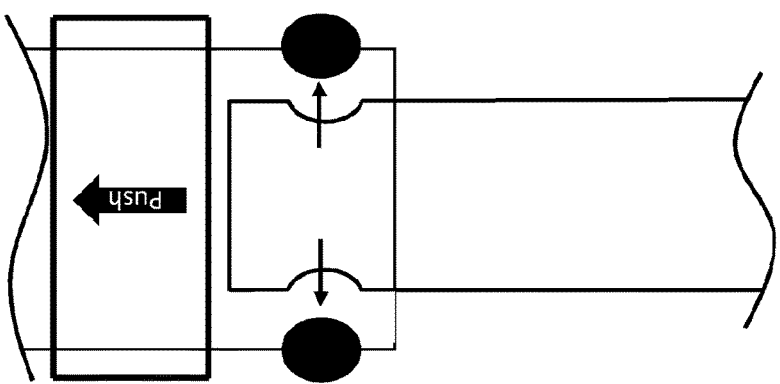
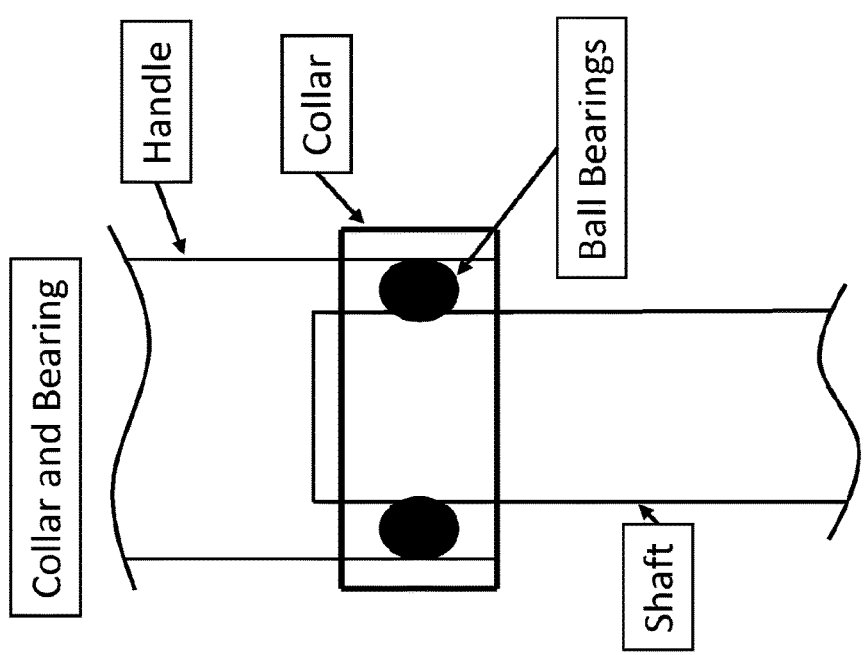
Figure 8a

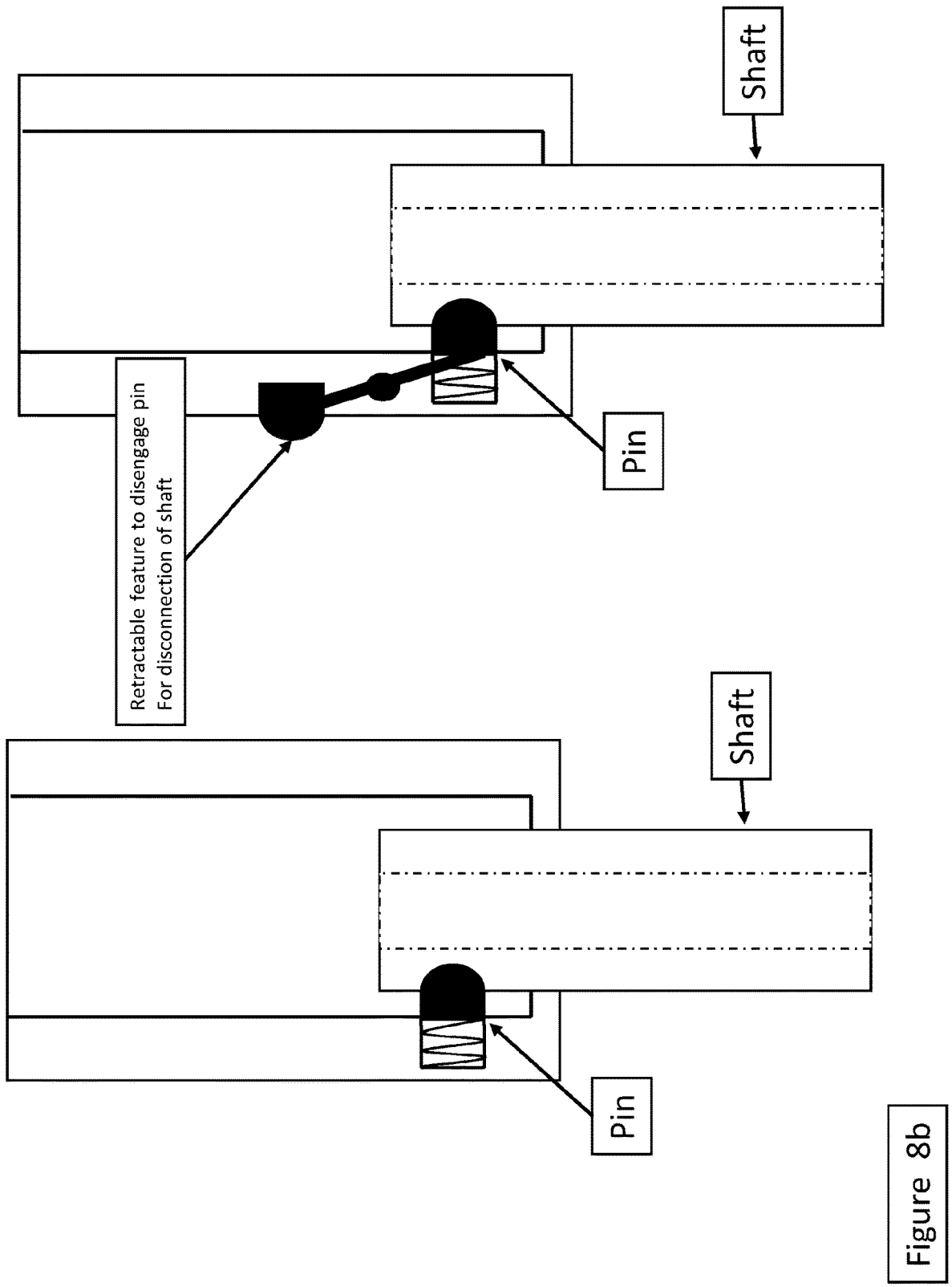

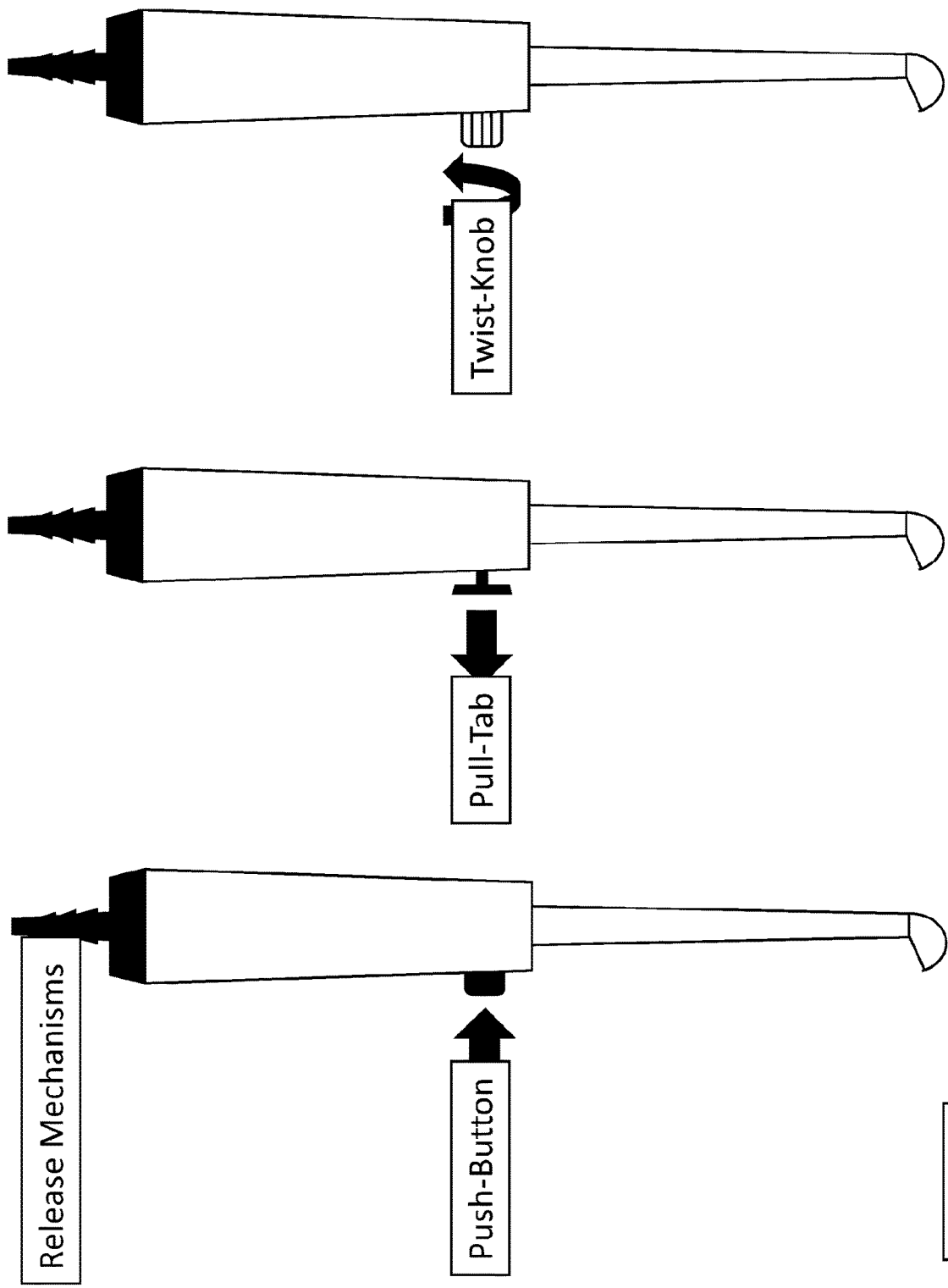

Metal Shaft Design Features Bosses on Metal Shaft

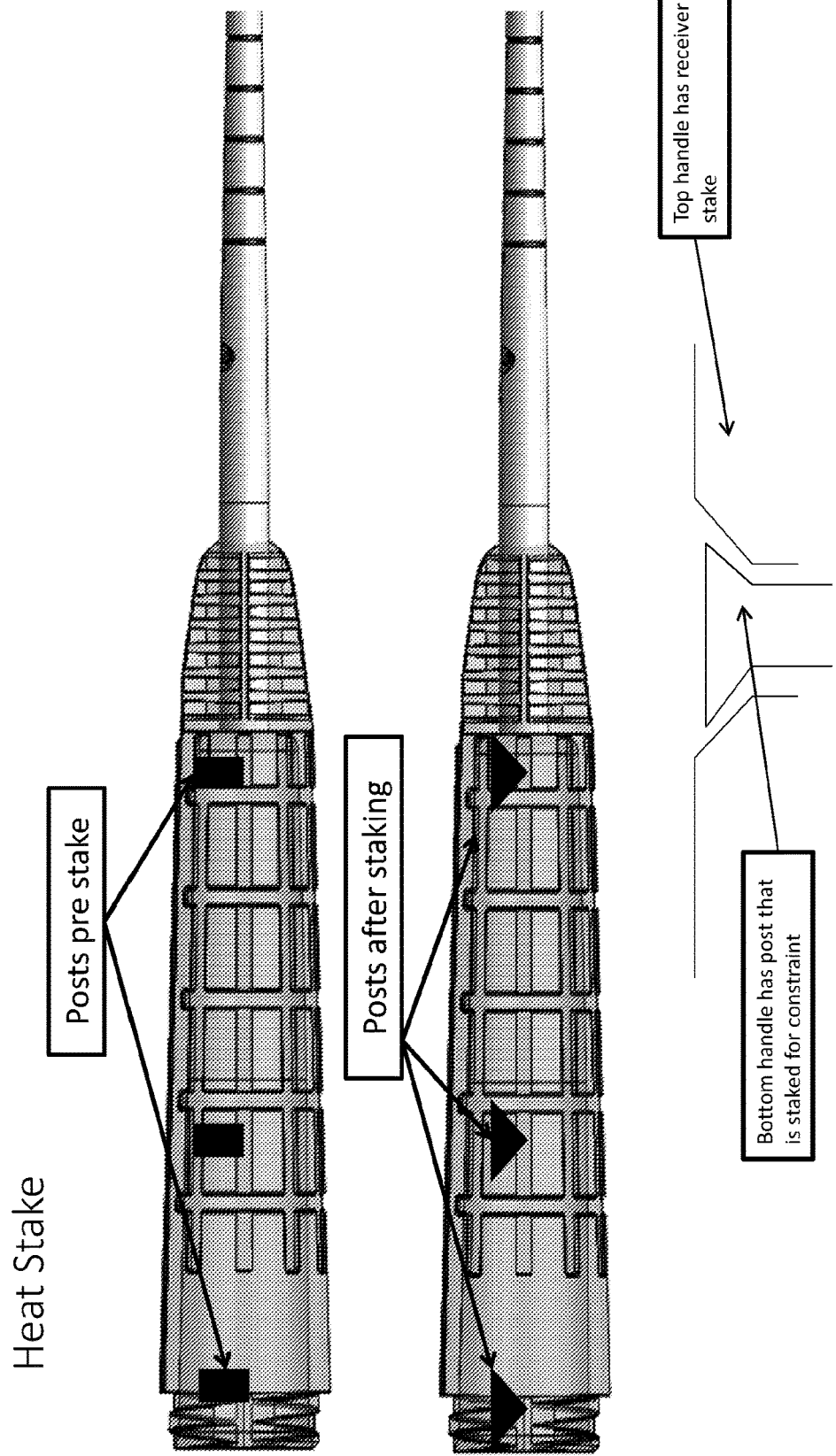

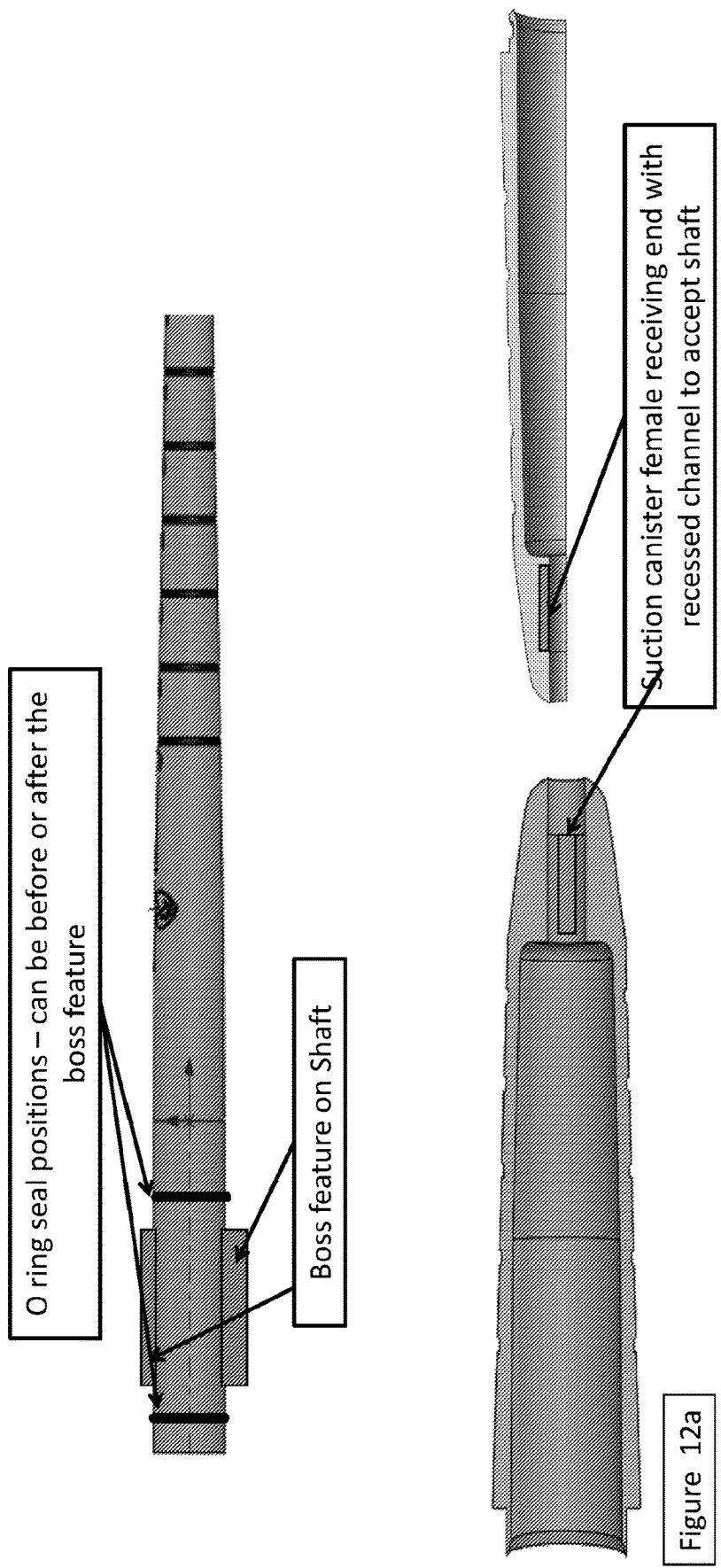

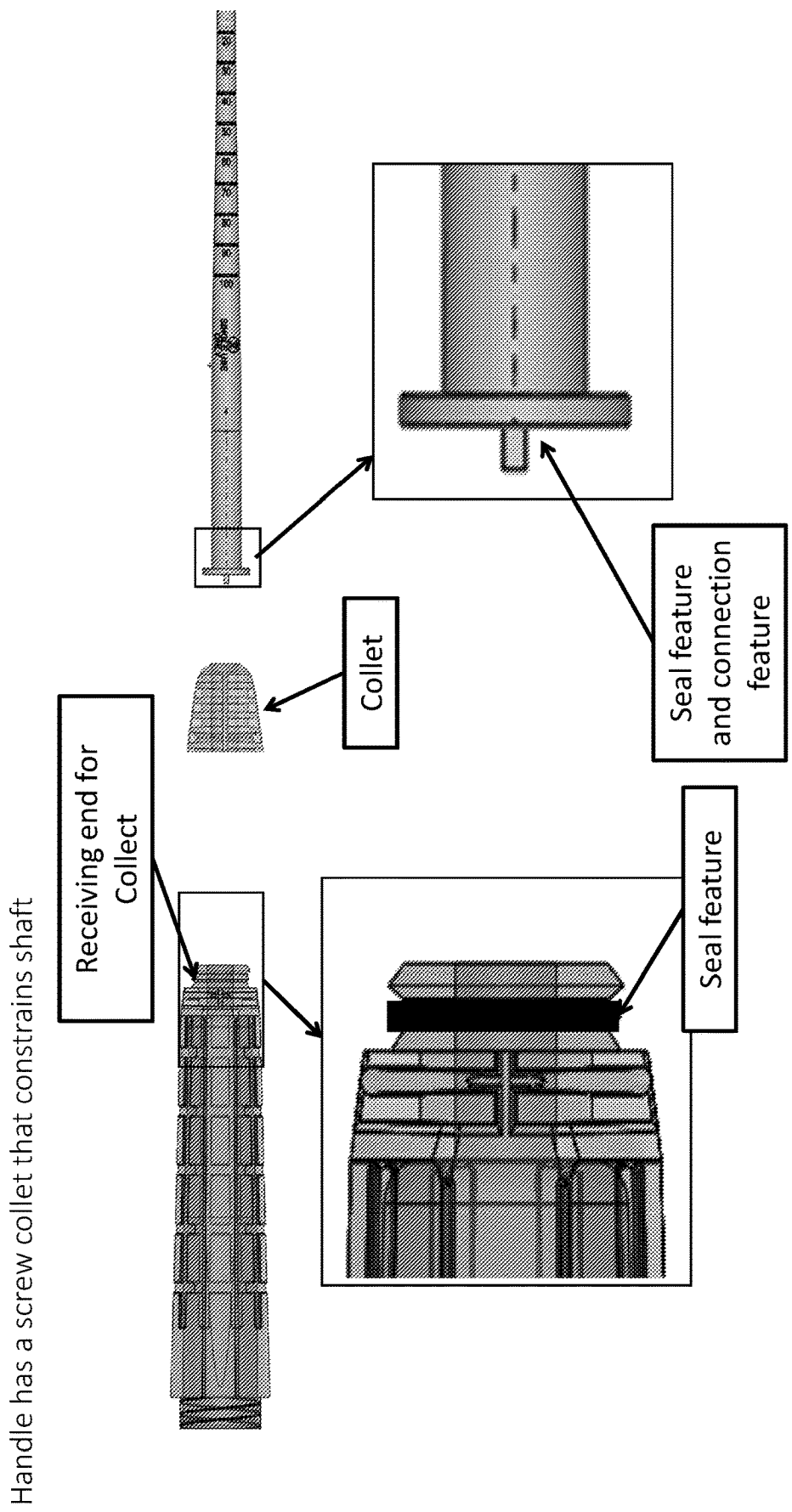

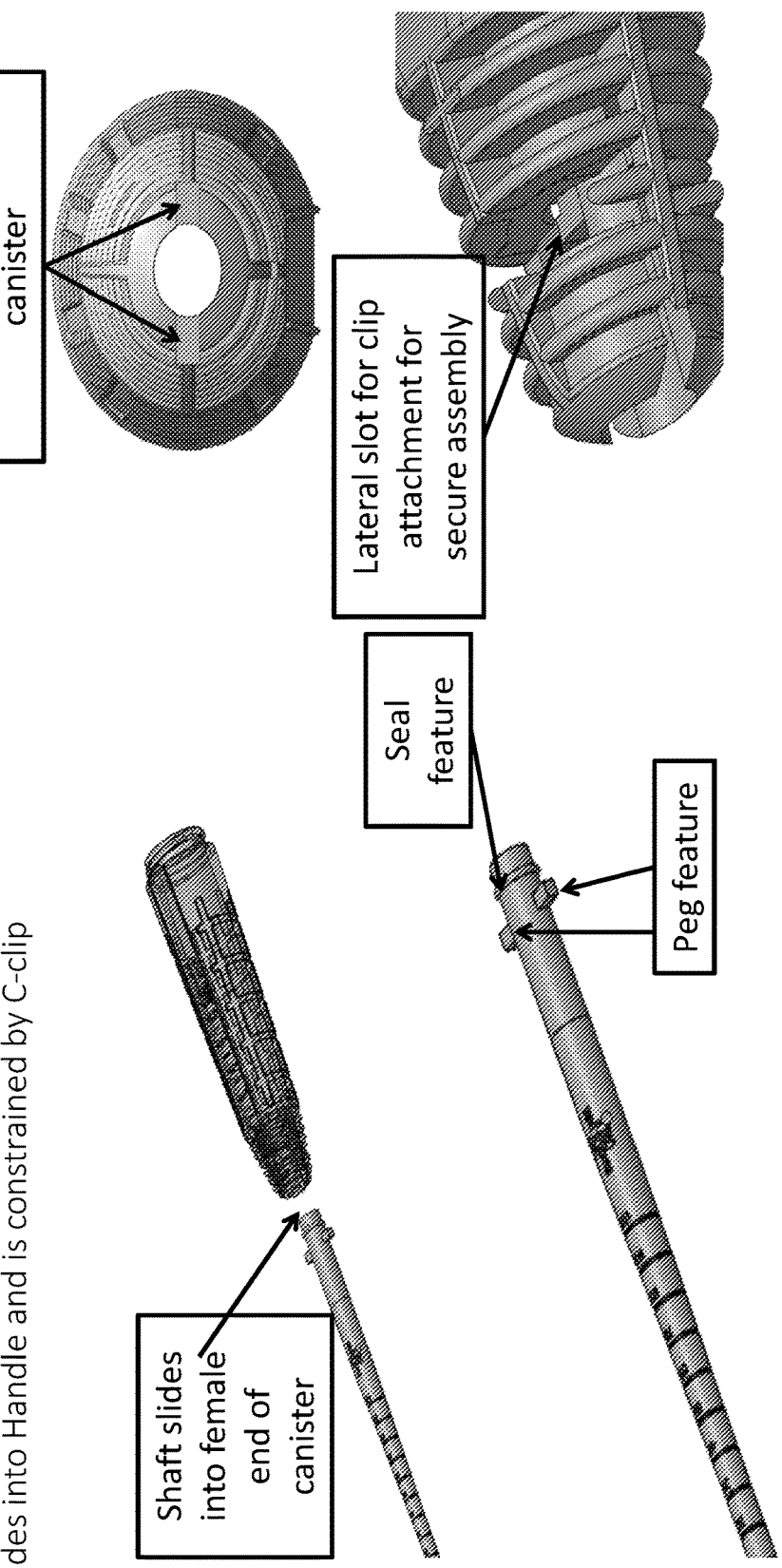

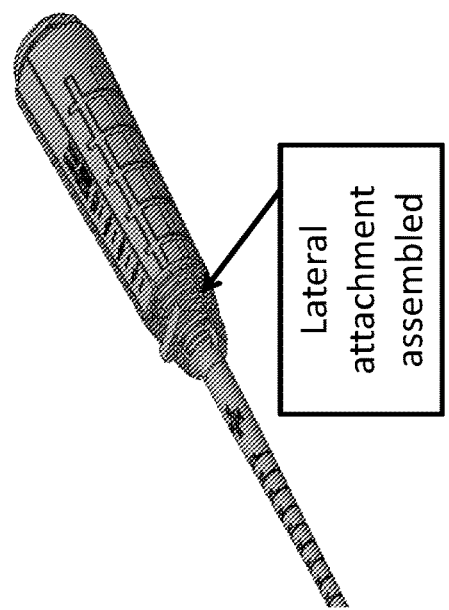
Figure 14b — Lateral attachment assembled
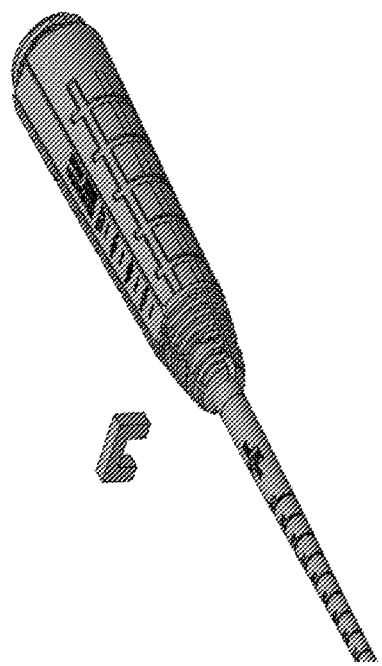
C-Clip inserted into handle to fully constrain shaft Once c-clip is inserted into handle an additional tool will be used to pop out c-clip If temporary connection, an accessory can be used to detach the lateral attachment to release the shaft from the canister C-clip geometry allows for compression to constrain shaft and then a pull to eject Alternative engaging/disengaging feature Figure 14f
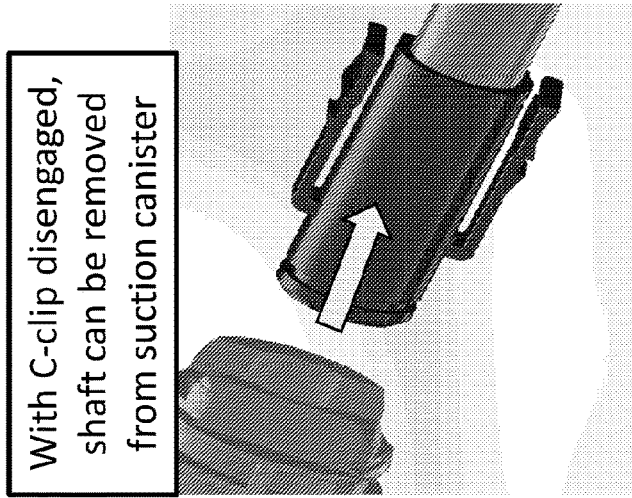
With C-clip disengaged, shaft can be removed from suction canister
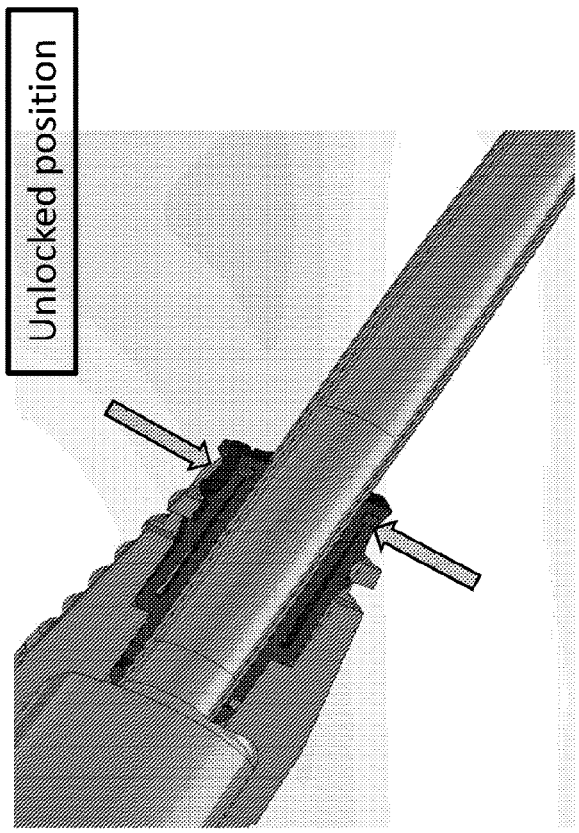
Unlocked position
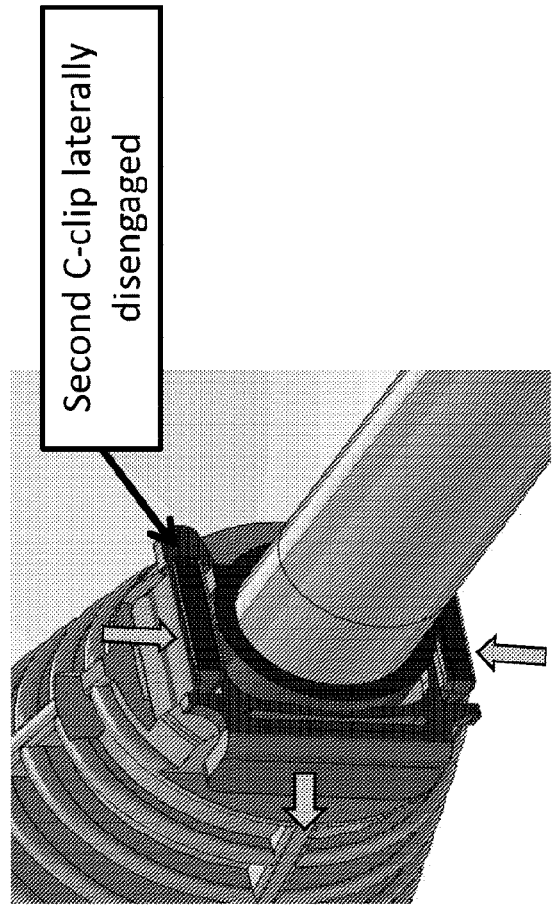
Second C-clip laterally disengaged

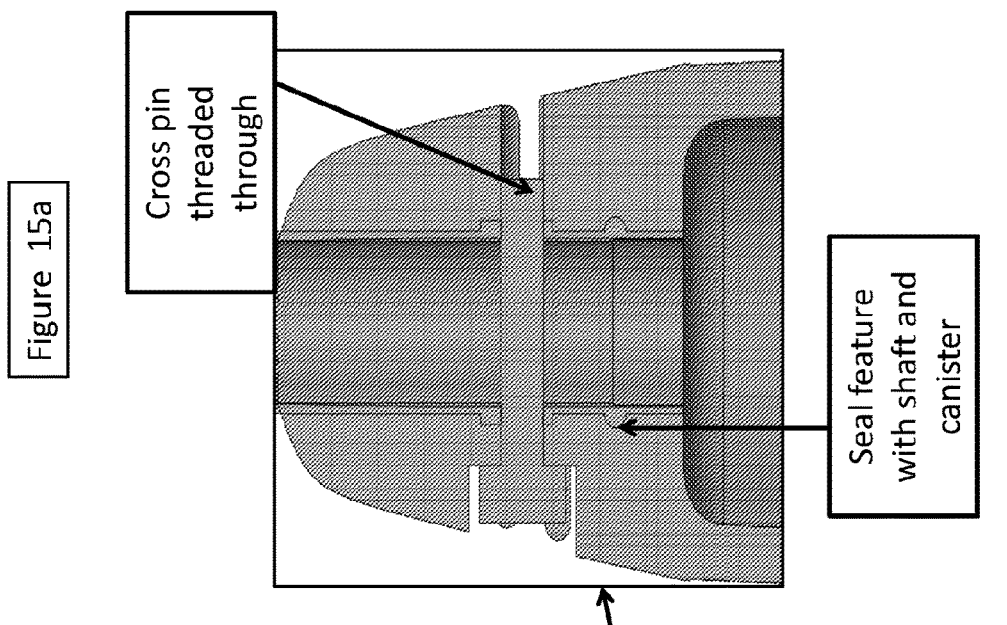
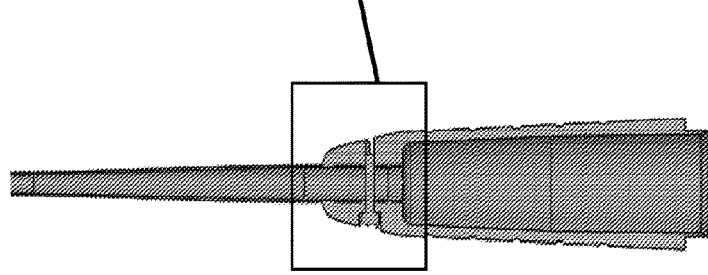
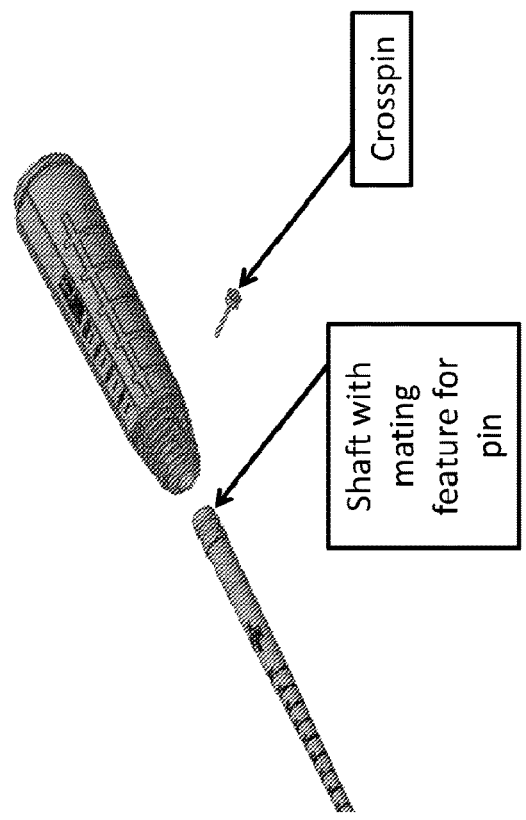
Figure 15a

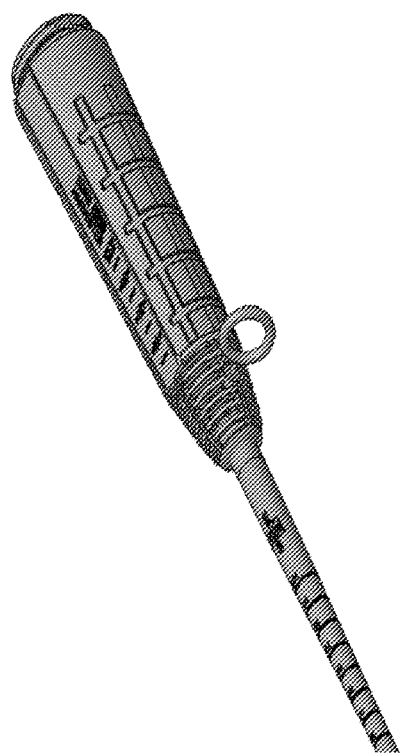
Figure 15b
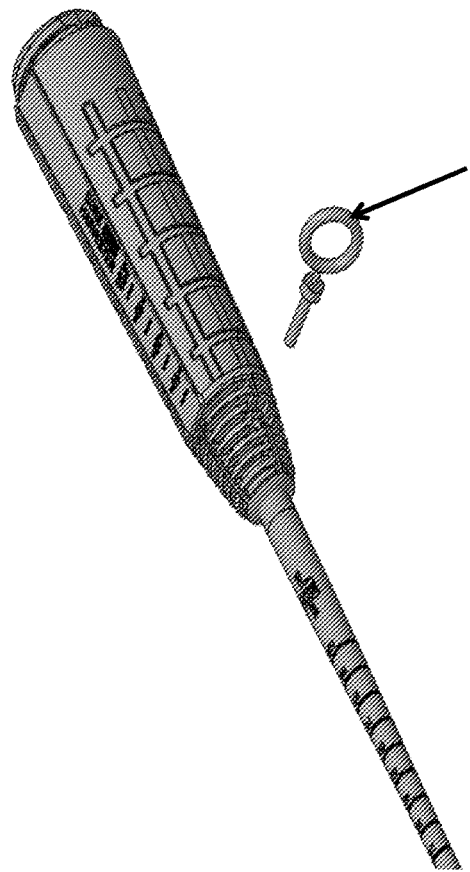
Removable pin snapped into handle to constrain shaft

Different Pin Concepts

Push Button with Retaining Balls for Security

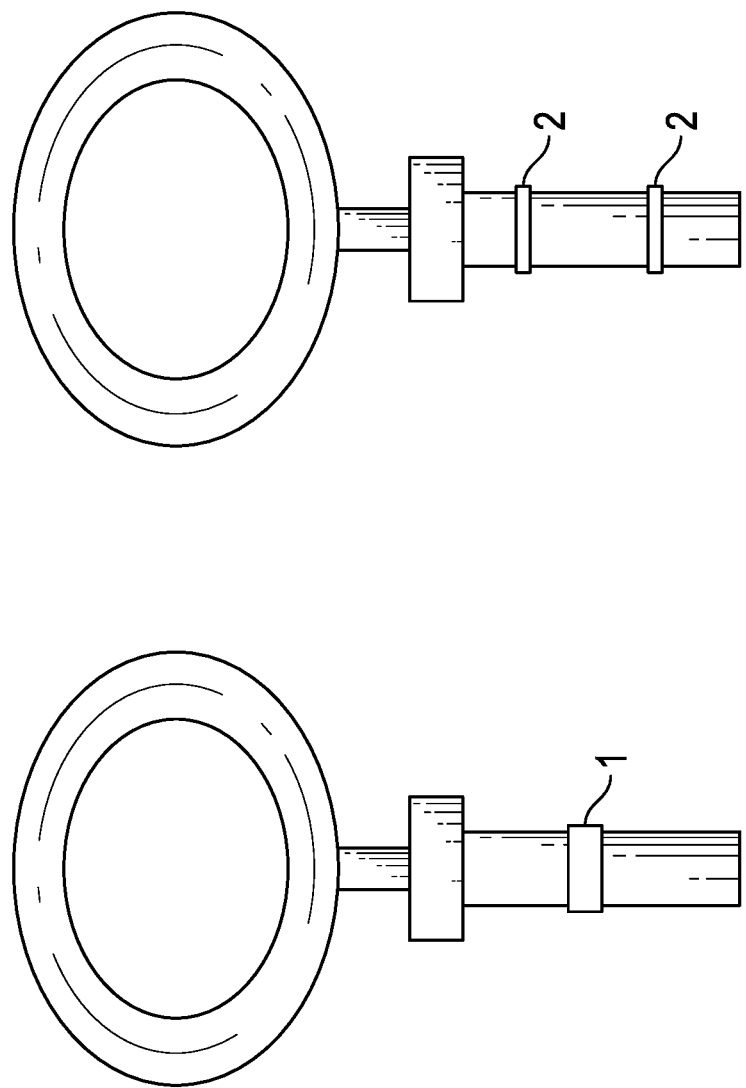

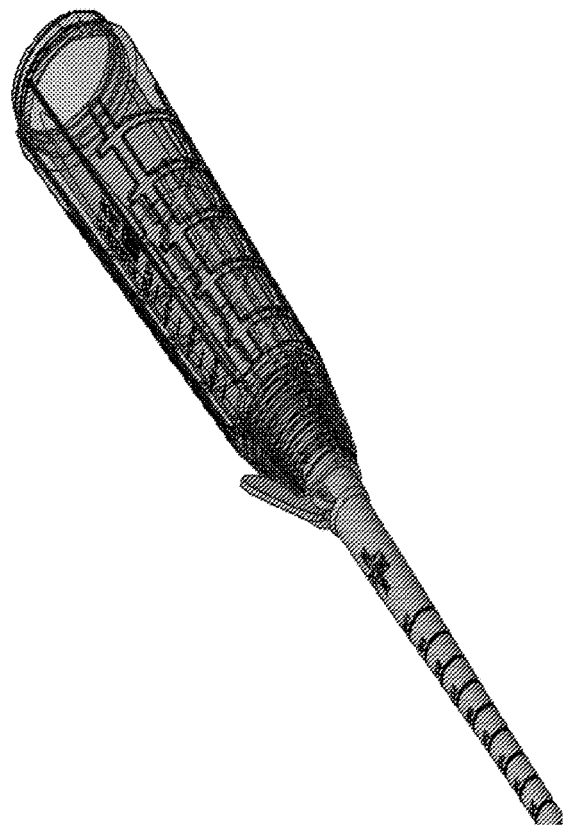
Figure 16a
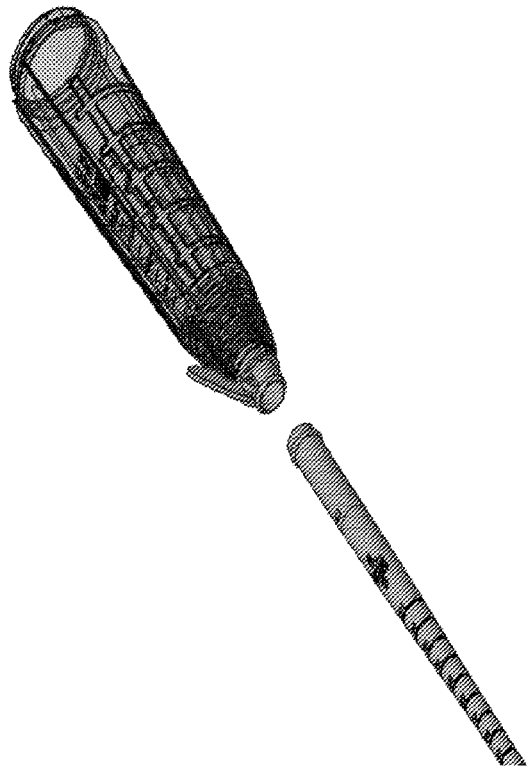
Cam lever to allow for insertion and removal of different shafts

Figure 18

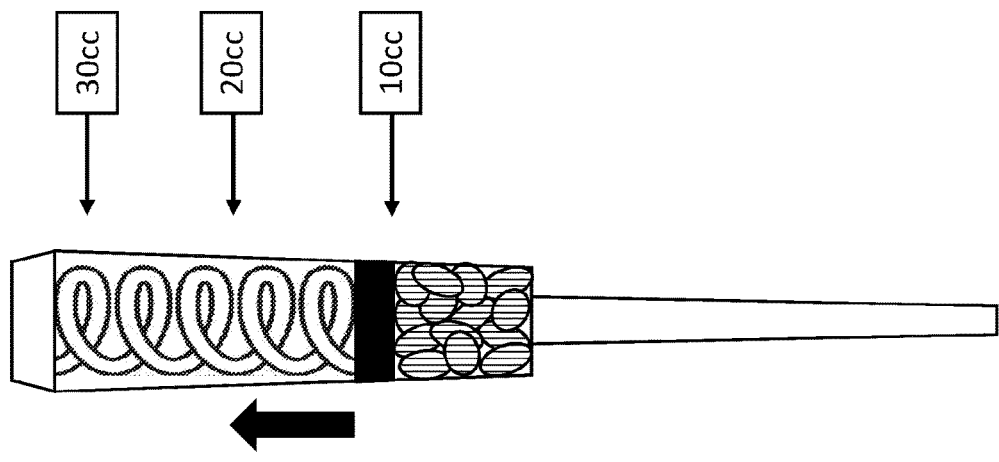
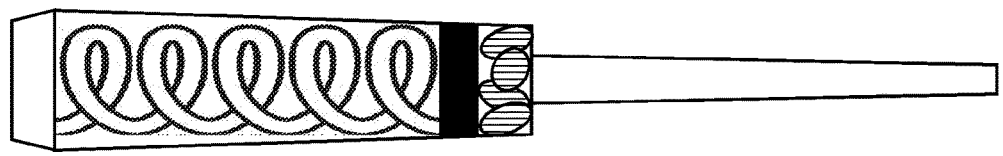
Spring Loaded Plunger
Figure 21

15ml Cylinder Insert
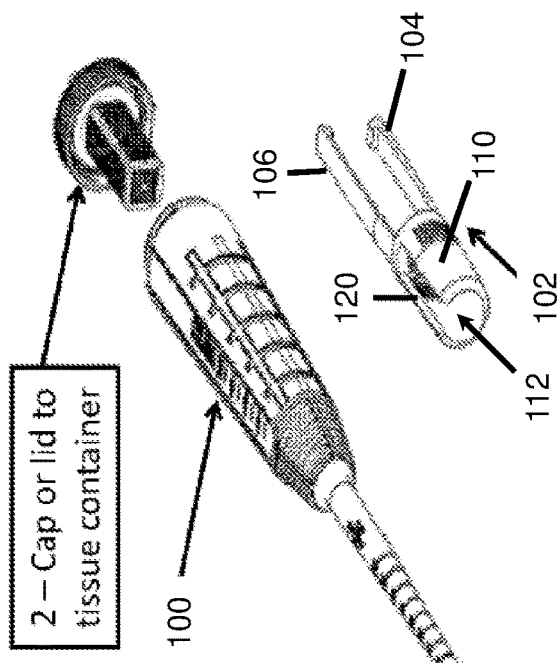
2 – Cap or lid to tissue container
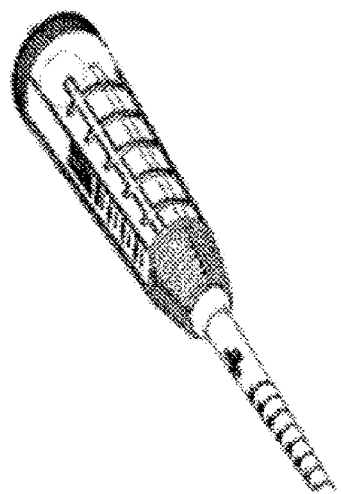
Figure 23a

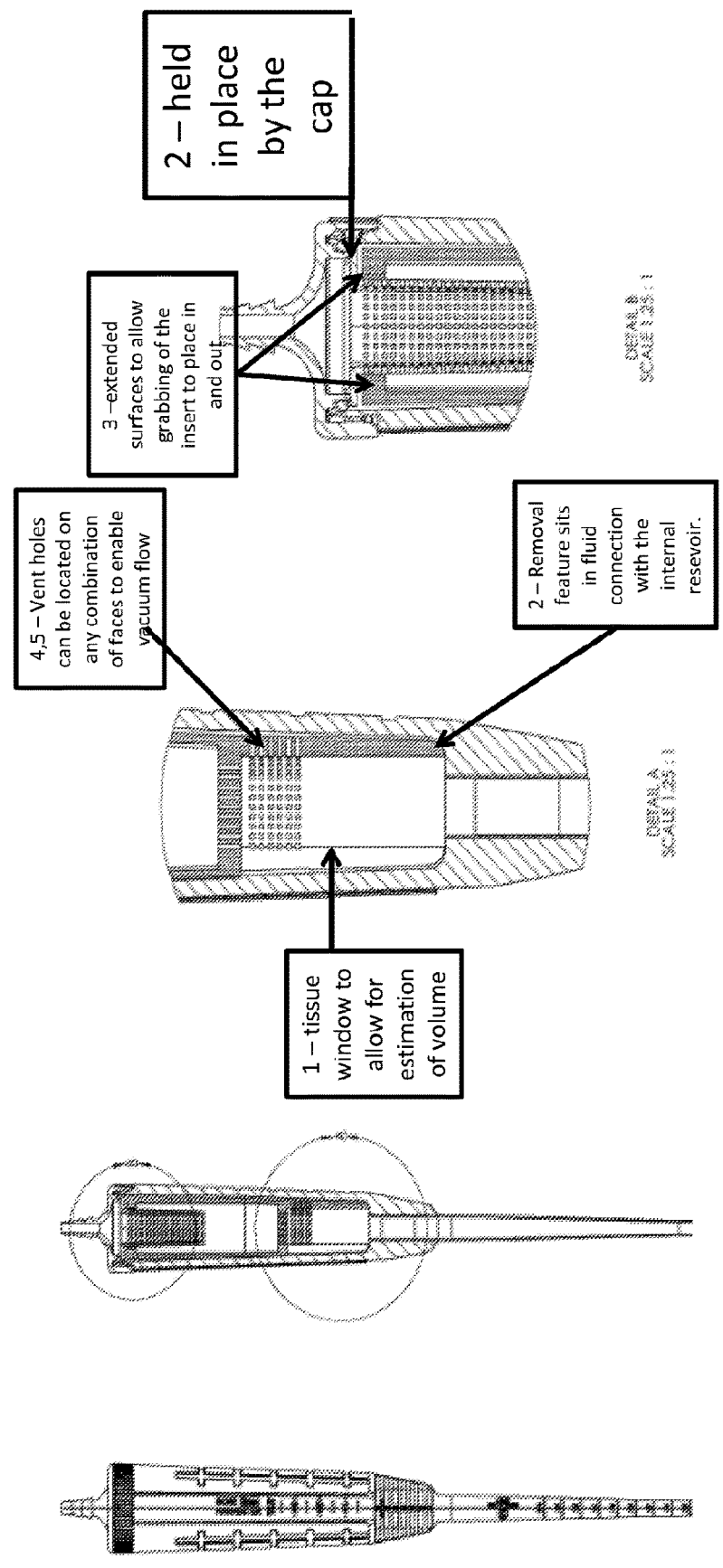

Tissue removal disc

Figure 31a
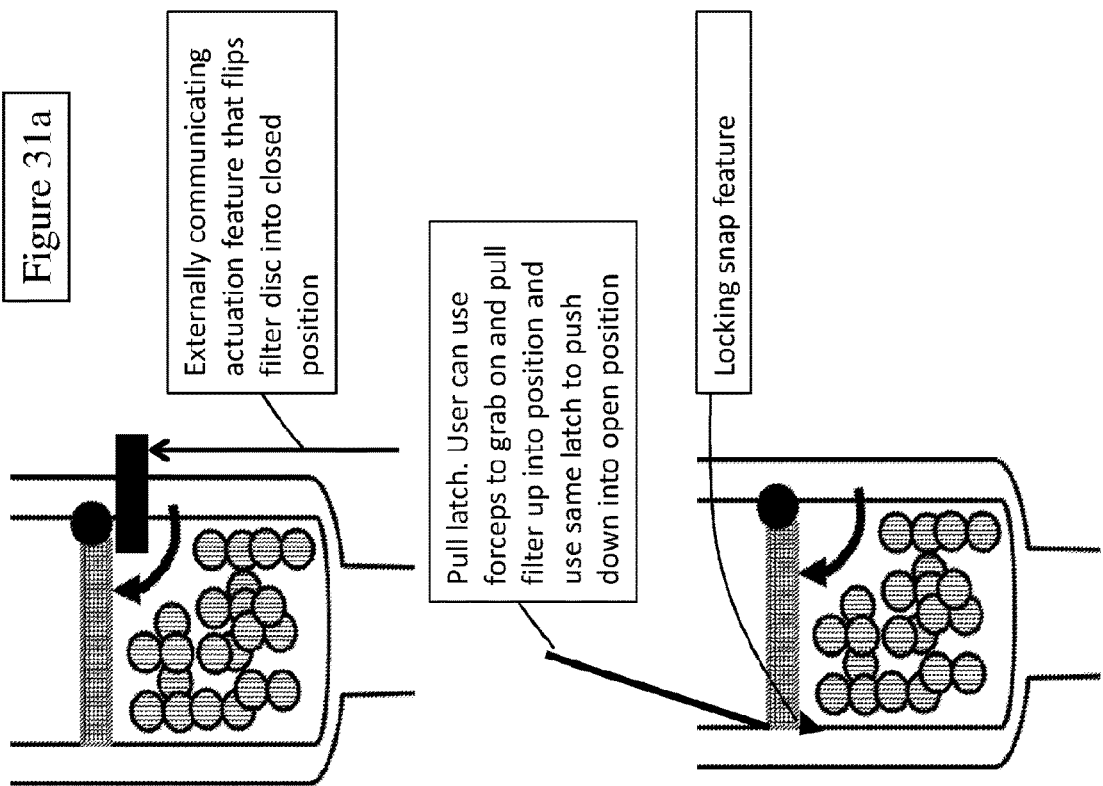
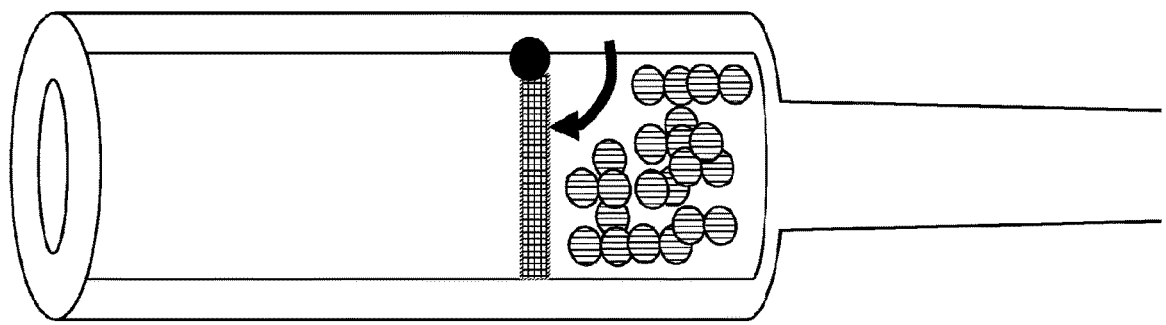
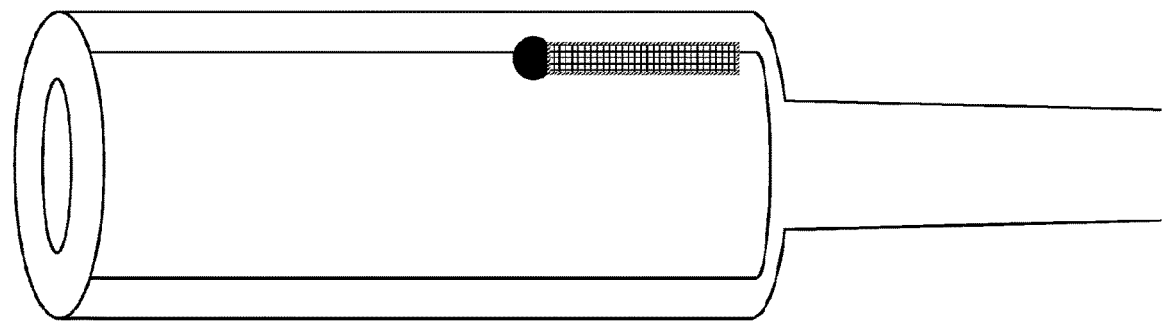

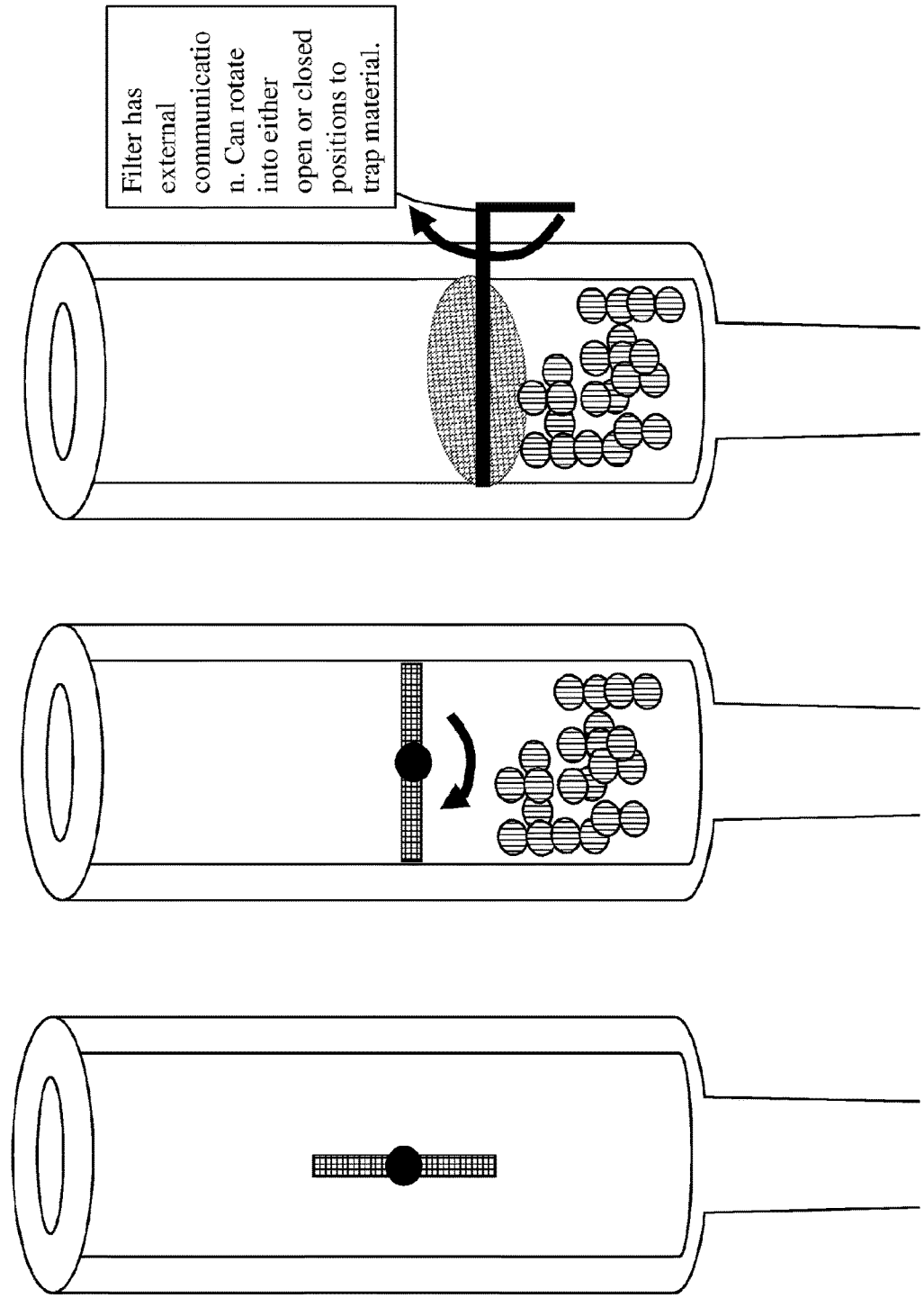

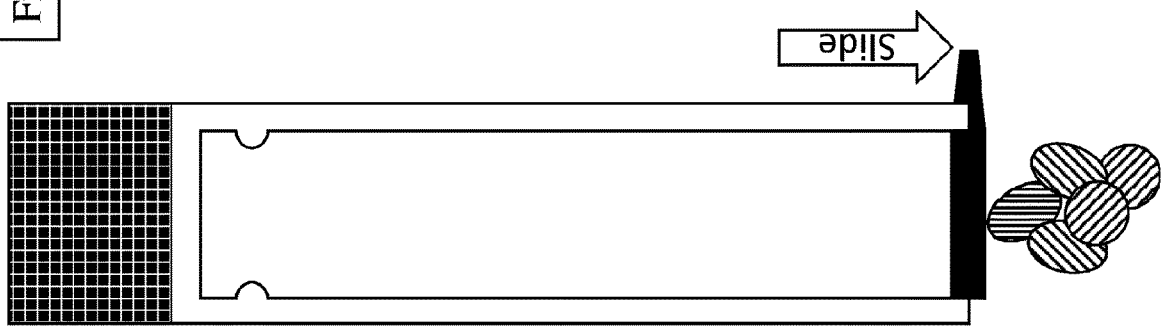
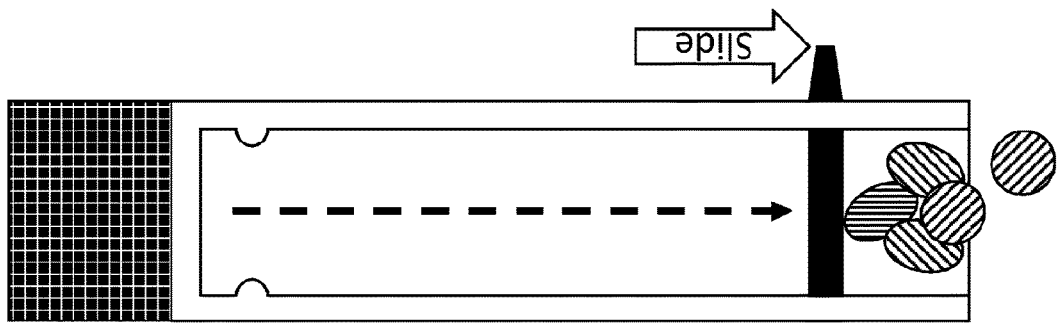
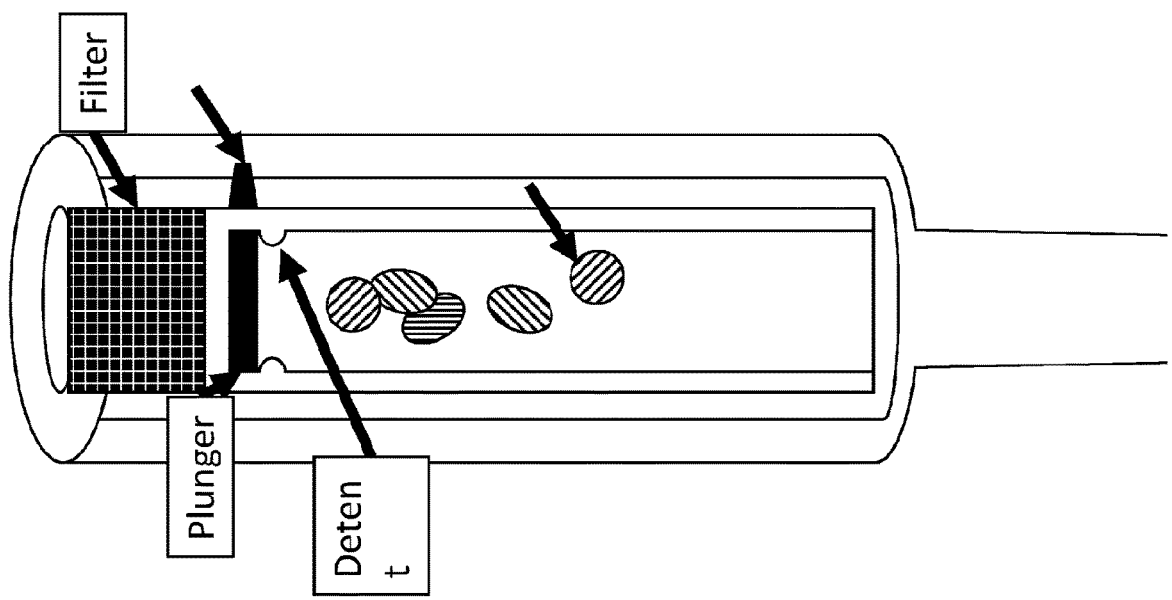
Figure 33a

Tip Geometry

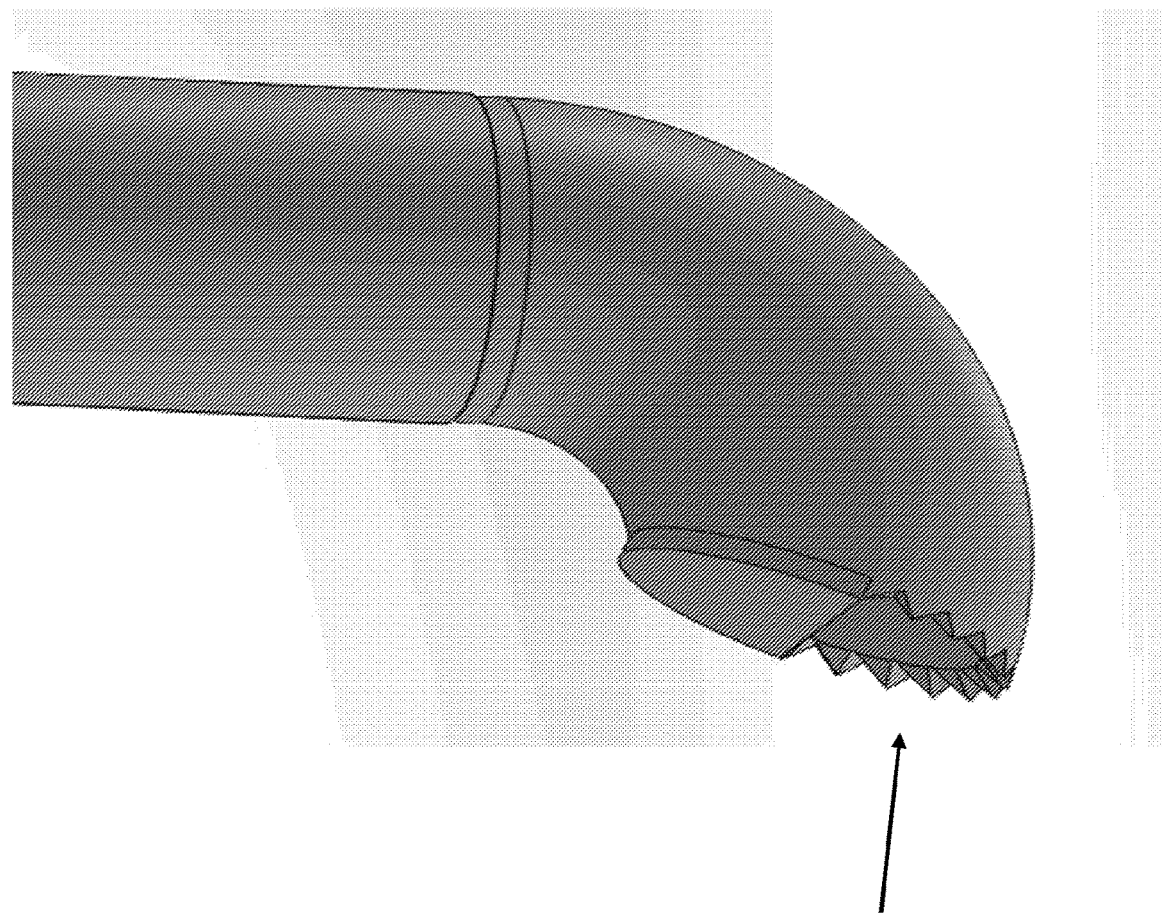
Cutting Edge
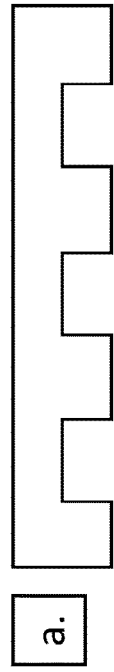 a.
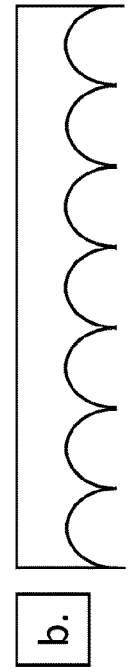 b.
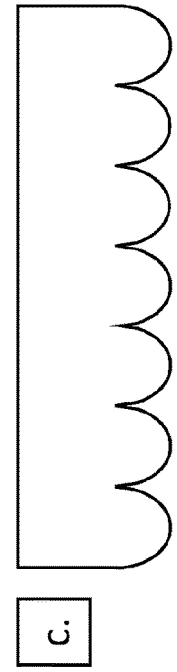 c.
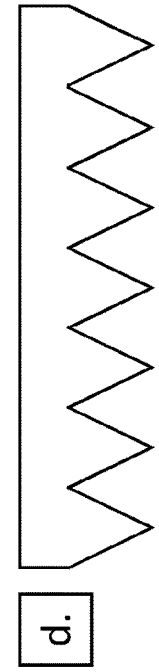 d.
Figure 35

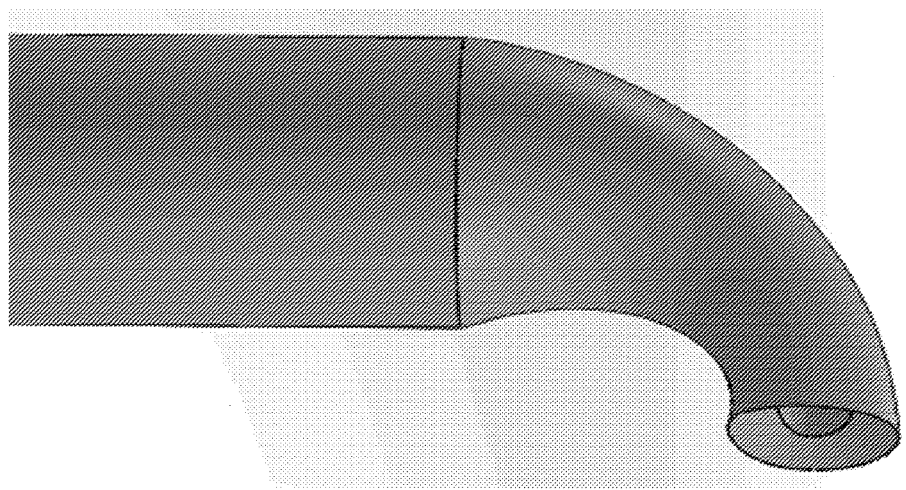
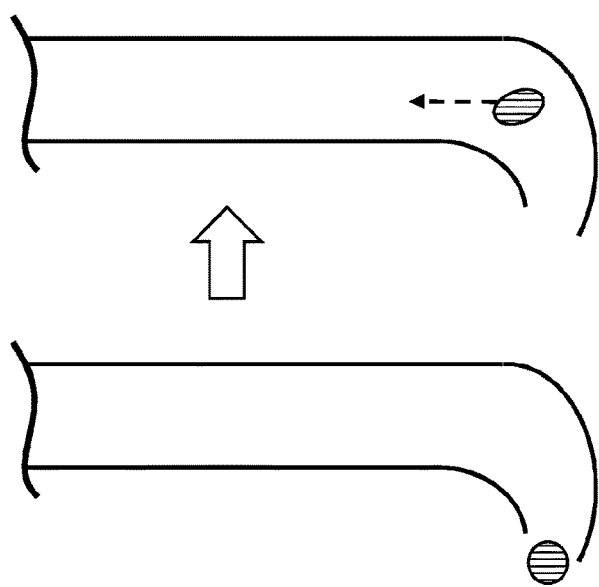
Tapered Tip
Figure 36

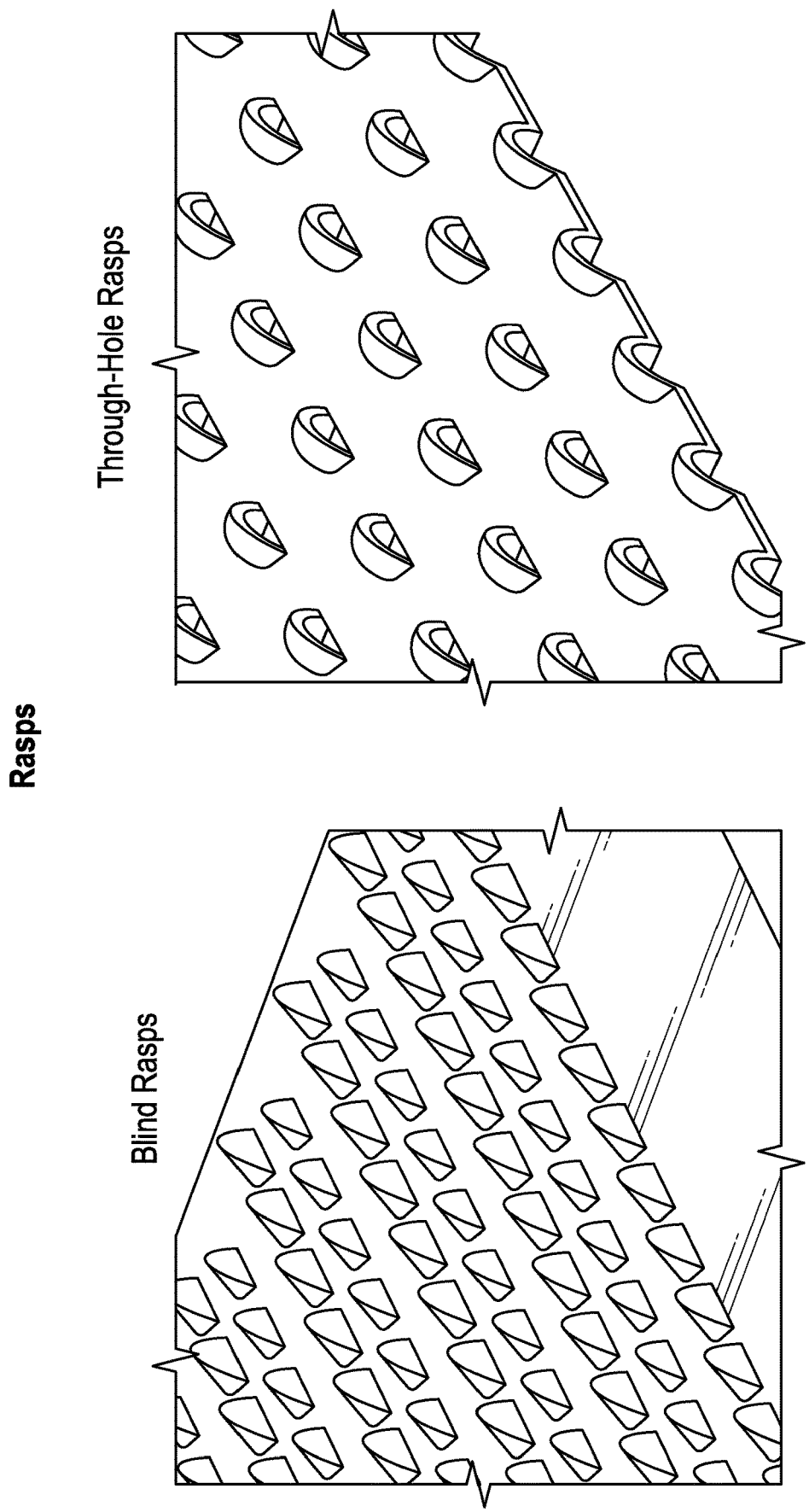

SYSTEMS AND METHODS FOR BONE AND TISSUE HARVESTING

CROSS-REFERENCE TO RELATED APPLICATION(S)

The present application is a 35 U.S.C. § 371 National Stage filing of International Application No. PCT/US2016/031503, filed on May 9, 2016, which PCT application claims priority benefit to a provisional patent application entitled "Bone/Tissue Harvesting Systems and Methods," which was filed on May 7, 2015, and assigned Ser. No. 62/158,226. The entire content of the foregoing PCT and provisional patent applications is incorporated herein by reference. The present application is also generally related to the subject matter of a PCT patent application entitled "Bone Harvesting," which was filed on Mar. 15, 2013 and assigned Serial No. PCT/US2013/032531, and the family of applications related thereto. The entire content of the foregoing PCT patent application is also incorporated herein by reference.

BACKGROUND

Bone grafts are used in surgical procedures that require the fusion, healing or joining of bones. Often bone grafts are harvested from the cancellous bone of a patient's own body, for example from the iliac crest, the fibula, the ribs, the mandible, or any other area where cancellous bone is accessible.

The present applicants filed a PCT patent application entitled "Bone Harvesting" (Serial No. PCT/US2013/032531; filed on Mar. 15, 2013) which described advantageous devices and systems for harvesting bone and tissue. As noted above, the entirety of the foregoing PCT application is incorporated herein by reference. The present application provides improvements, enhancements and/or extensions to the previously disclosed bone/tissue harvesting devices and systems.

SUMMARY

The present disclosure provides advantageous interconnectivity amongst different components of a tool, device or system that includes (a) a generally cylindrical, hollow shaft, and (b) a suction canister. Some benefits of introducing a connection feature and/or functionality as described herein are: to enable ease of manufacturing and lowered manufacturing costs, and to allow for a platform of different shaft embodiments and canister embodiments that may be manufactured in different combinations to form an array of unique instruments.

The disclosed interconnectivity may be irreversible (i.e., once the components are joined, they cannot be separated by the user during the ordinary course of use) or reversible (i.e., the user has the ability to connect and disconnect the components during the ordinary course of use). The connection features must maintain an air tight seal between the components.

For ease of use to the surgeon, the present disclosure further provides tools, devices and systems that include collection functionality that can be employed to manipulate the volume of tissue collected while using a tissue collection feature/function. This may be undertaken, for example, to restrict total volume of the collection chamber in a way that allows for continuous suction flow rate to take place while collecting the desired amount of tissue. Often, tissue can splatter inside a collection chamber, creating situations in which the volume of tissue collected is difficult to read. Containing the tissue to a pre-set volume can enable a user to effectively ascertain the volume of tissue collected.

In additional exemplary embodiments, advantageous cutting element designs are provided according to the present disclosure.

Of note, each of the advantageous features, functions, structures and mechanisms disclosed herein may be used interchangeably with other features, functions, structures and mechanisms disclosed herein. Thus, for example, any of the disclosed interconnectivity features, functions, structures and mechanisms disclosed herein may be used with any of the collection features, functions, structures and mechanisms disclosed herein and/or any of the cutting element designs disclosed herein (and vice versa), so as to realize the combined benefits thereof, as will be apparent to persons skilled in the art from the detailed description which follows.

Additional advantageous features, functions and benefits of the disclosed devices, systems and methods will be apparent from the description which follows, particularly when read in conjunction with the appended figures.

BRIEF DESCRIPTION OF THE FIGURES

To assist those of skill in the art in making and using the devices, systems and methods of the present disclosure, reference is made to the accompanying figures, wherein:

FIG. 3 schematically depicts an exemplary connection feature between a shaft and suction canister according to the present disclosure;

FIG. 6a schematically depicts a further exemplary connection feature according to the present disclosure;

FIG. 6b schematically depicts the exemplary connection feature of FIG. 6a that incorporates a hooked slot according to the present disclosure;

FIG. 7a schematically depicts a further exemplary connection feature according to the present disclosure;

FIG. 7b schematically depicts a further exemplary connection feature according to the present disclosure;

FIG. 7c schematically depicts unlocking movement of the connection feature of FIG. 7b according to the present disclosure;

FIG. 8a schematically depicts a further exemplary connection feature according to the present disclosure;

FIG. 8b schematically depicts a further exemplary connection feature according to the present disclosure;

FIG. 9 schematically depicts three (3) exemplary release mechanisms according to the present disclosure;

FIGS. 11c and 11d schematically depict a further exemplary connection feature utilizing connecting halves according to the present disclosure;

FIGS. 12a and 12b schematically depict exemplary mating features according to the present disclosure;

FIGS. 13a and 13b schematically depict an exemplary handle collet-based assembly according to the present disclosure;

FIGS. 14a and 14b schematically depict a further exemplary connection feature in which the shaft includes peg features according to the present disclosure;

FIGS. 14e and 14f schematically depict a further exemplary connection feature according to the present disclosure;

FIG. 15a schematically depicts a further exemplary connection feature according to the present disclosure;

FIG. 15b schematically depicts a further exemplary connection feature according to the present disclosure;

FIG. 15e schematically depicts an exemplary seal features according to the present disclosure;

FIGS. 16a and 16b schematically depict a further exemplary connection feature according to the present disclosure;

FIG. 18 schematically depicts an embodiment that contains a filter including fine pores that are susceptible to clogging;

FIG. 21 schematically depicts a further volume control system that includes a spring-loaded perforated plunger according to the present disclosure;

FIG. 23a schematically depicts an exemplary embodiment that includes removable tissue containment inserts according to the present disclosure;

FIG. 23b schematically depicts an exemplary embodiment that includes a tissue window according to the present disclosure;

FIG. 31a schematically depicts a further exemplary tissue containment feature according to the present disclosure;

FIG. 31c schematically depicts an exemplary embodiment wherein the filter rotates about a central axis according to the present disclosure;

FIG. 33a schematically depicts an exemplary insert geometry according to the present disclosure;

FIG. 35 schematically depicts various manipulations to the cutting edge of the cutting element according to the present disclosure;

FIG. 36 schematically depicts an exemplary cutting tip that features a gradual reduction in tip diameter according to the present disclosure;

FIG. 38 schematically depicts rasp-like cutting teeth according to the present disclosure;

DESCRIPTION OF EXEMPLARY EMBODIMENTS

As noted above, the present disclosure provides tools, devices and systems that include inter-connective functionality amongst different components. The disclosed tools, devices and systems generally include (a) a generally cylindrical, hollow shaft, and (b) a suction canister. The interconnectivity may be irreversible (i.e., once the components are joined, they cannot be separated by the user during the ordinary course of use) or reversible (i.e., the user has the ability to connect and disconnect the components during the ordinary course of use). The connection features maintain an air tight seal between the components. Benefits of the disclosed connection feature and/or functionality as described herein include ease of manufacture, lowered manufacturing costs, and delivery of a platform of different shaft embodiments and canister embodiments that may be manufactured in different combinations to form an array of unique instruments.

The following figures pertain to exemplary mechanisms for connecting a generally cylindrical, hollow shaft with a suction canister, wherein the hollow shaft has features on the distal end for cutting material and the suction canister has at least one inlet and at least one outlet where suction is applied to the outlet drawing material through the inlet with intent of the material being collected inside the canister.

Figure 1:
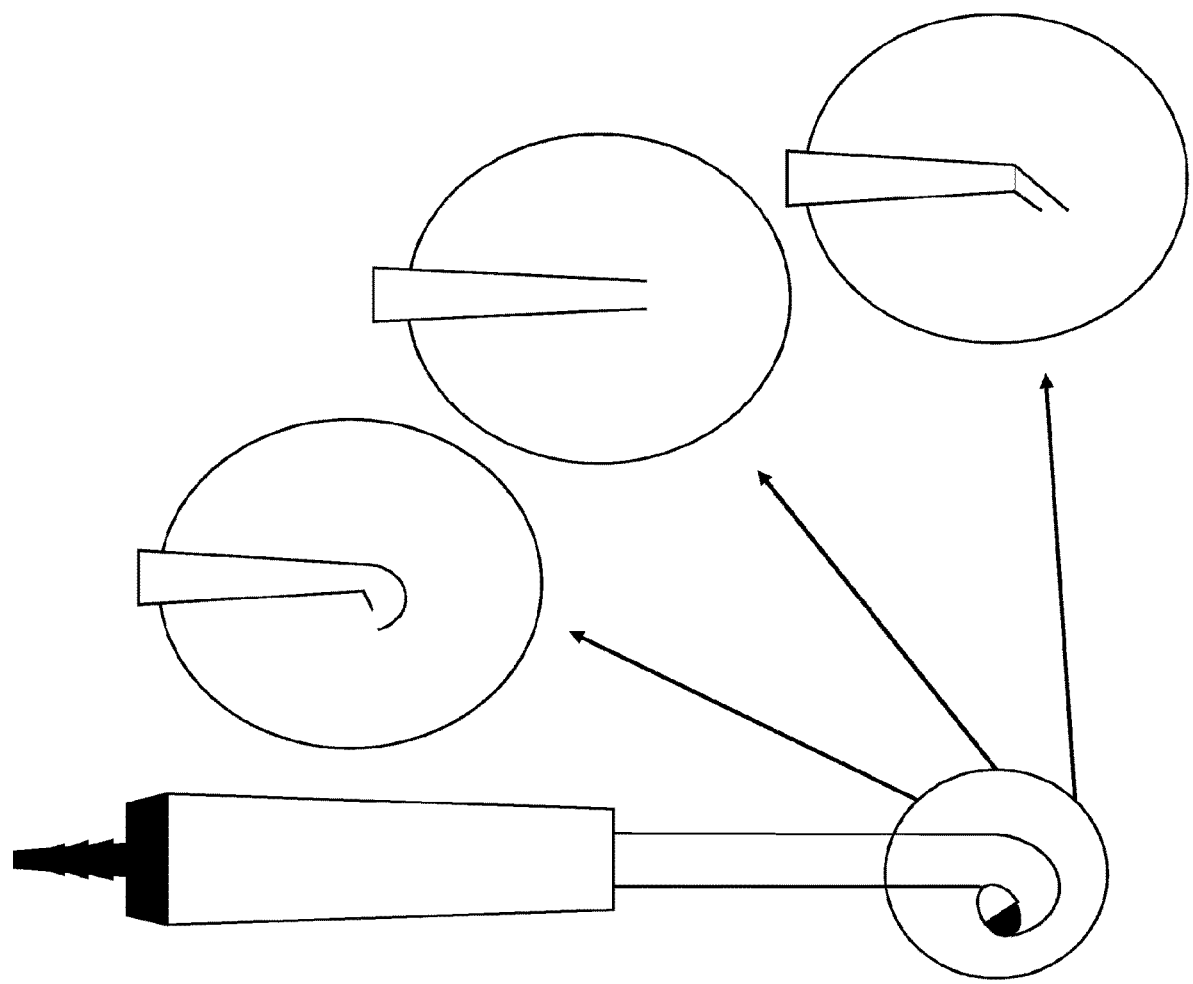
FIG. 1 schematically depicts an exemplary device according to the present disclosure.

More particularly, FIG. 1 depicts a generally cylindrical shaft connected to a suction canister in which the shaft has a distal curved element with a cutting element and an aperture into which cut material can be aspirated. The figure further depicts examples of variations to the distal element geometry that can be made possible by interconnectivity between the shaft and canister. The depicted variations of distal geometries are for example only and do not limit other embodiments of the distal geometry.

Figure 2:
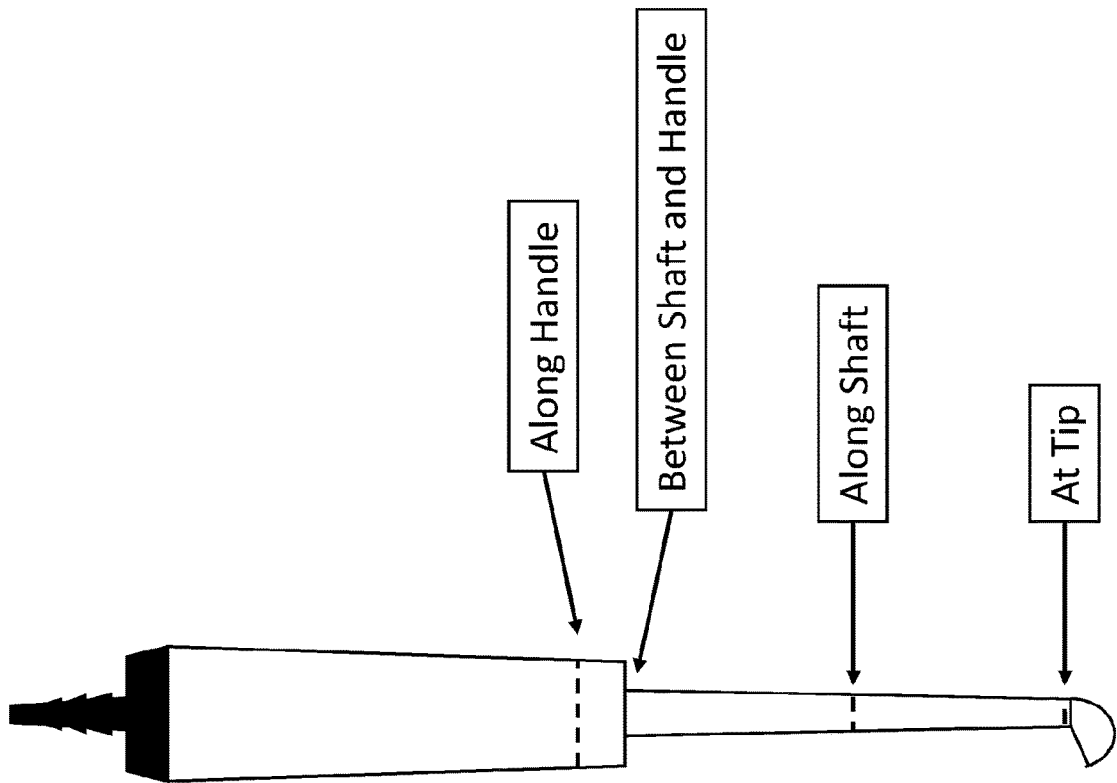
FIG. 2 schematically depicts four (4) exemplary locations at which an air-tight connection feature may be introduced to a device according to the present disclosure.

FIG. 2 displays four different locations at which an air-tight connection feature may be introduced: near the distal cutting feature (if one exists); along the generally cylindrical shaft; between the shaft and the suction canister; or along the suction canister.

FIG. 3 depicts an embodiment of a connection feature between the shaft and the suction canister. In this embodiment, the shaft contains at least one or more winged elements at the proximal end of the shaft. These winged elements are made of a flexible material which resists flexing away from the shaft and, when forced towards the shaft, have a tendency to spring back to their natural shape. The suction canister contains a mating feature at its distal end that communicates with these features. A hole is provided that is smaller than the full span of the winged elements in their natural shape, but larger than the diameter of the shaft near its proximal end. The two components are connected by pushing the shaft through the hole in the suction canister (left), causing the winged elements to flex against the hole and spring back to their natural shape upon clearing the hole. In its connected state (right), the wings of the shaft are in their natural shape within the canister and prevent the distal end of the shaft from being removed from the canister. An air-tight connection may be created through an interference fit or rubber-like material between the hole and shaft interface. The winged elements in the connected state securely enable the transmission of torque, tension, compression and orthogonal loads to the shaft.

Figure 4:
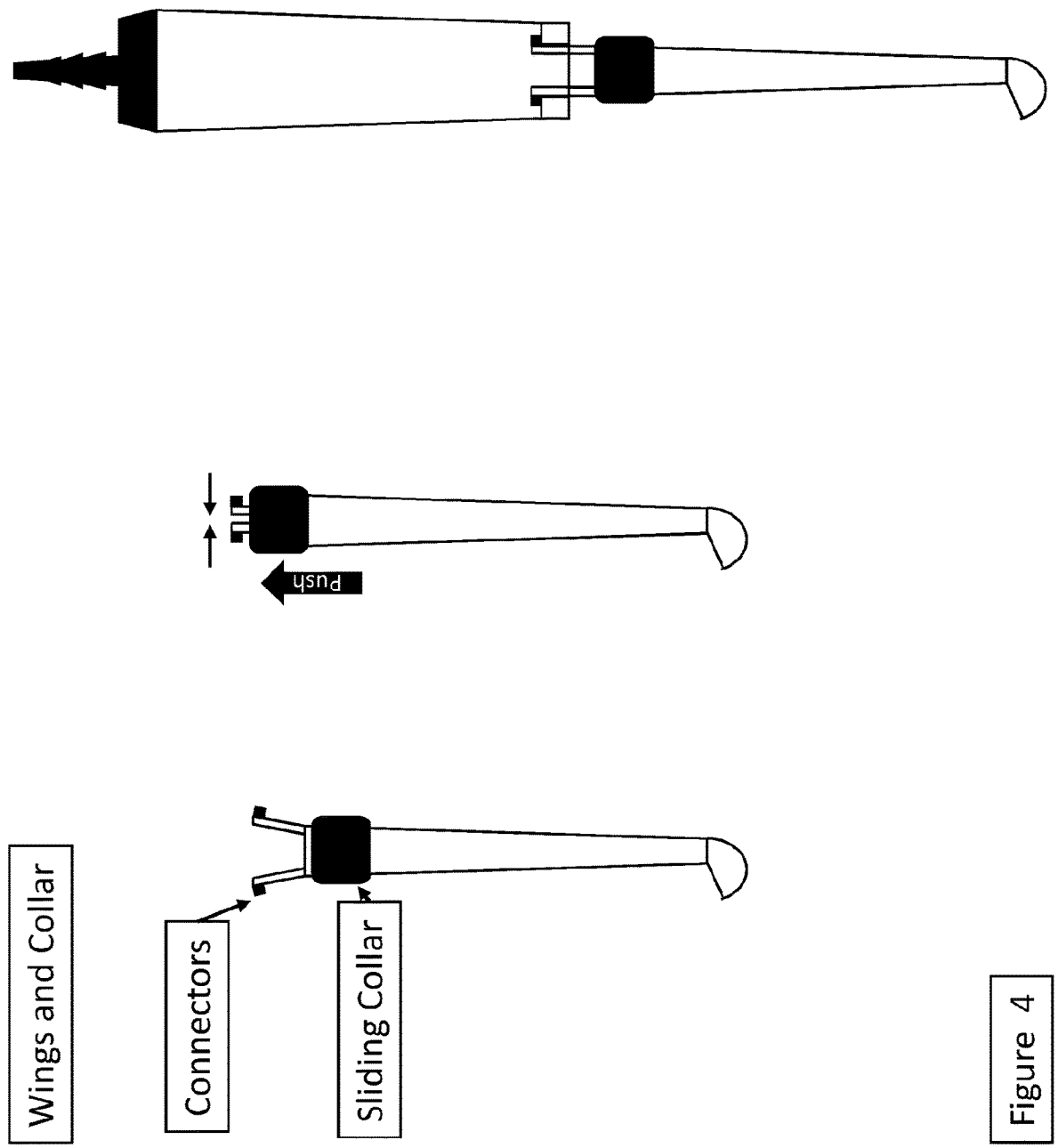
FIG. 4 schematically depicts a further exemplary connection feature according to the present disclosure.

FIG. 4 depicts an embodiment of a connection feature between the shaft and the suction canister. In this embodiment, the shaft contains two or more winged elements at the proximal end of the shaft. These winged elements, when forced inward, have a tendency to spring back to their natural shape. Furthermore, the winged elements have "connector" features at their tips which protrude laterally outward from each wing. This embodiment also contains a collar element that can slide up and down the proximal end of the shaft (left). When the collar is slid proximally, it forces the wings to flex inward toward the central axis of the shaft (middle). The suction canister contains a connection feature at its distal end. The connection element allows the wings to fit in a male-to-female fashion. The two components are connected by sliding the collar proximally (causing the wings to flex inward), passing the wings through the hole in the suction canister, then sliding the collar back down to release the wings and enable them to flex outward (right). The wings are prevented from passing back through the hole by the connectors which protrude laterally into the canister and span wider than the size of the hole. An air-tight connection may be created through an interference fit or rubber-like material between the hole and the wings or the collar.

An alternate configuration to the embodiments described above may feature a connection method where the compressed wing can thread or snap into place. Air tight threads in this configuration can enable an air tight connection.

Figure 5:
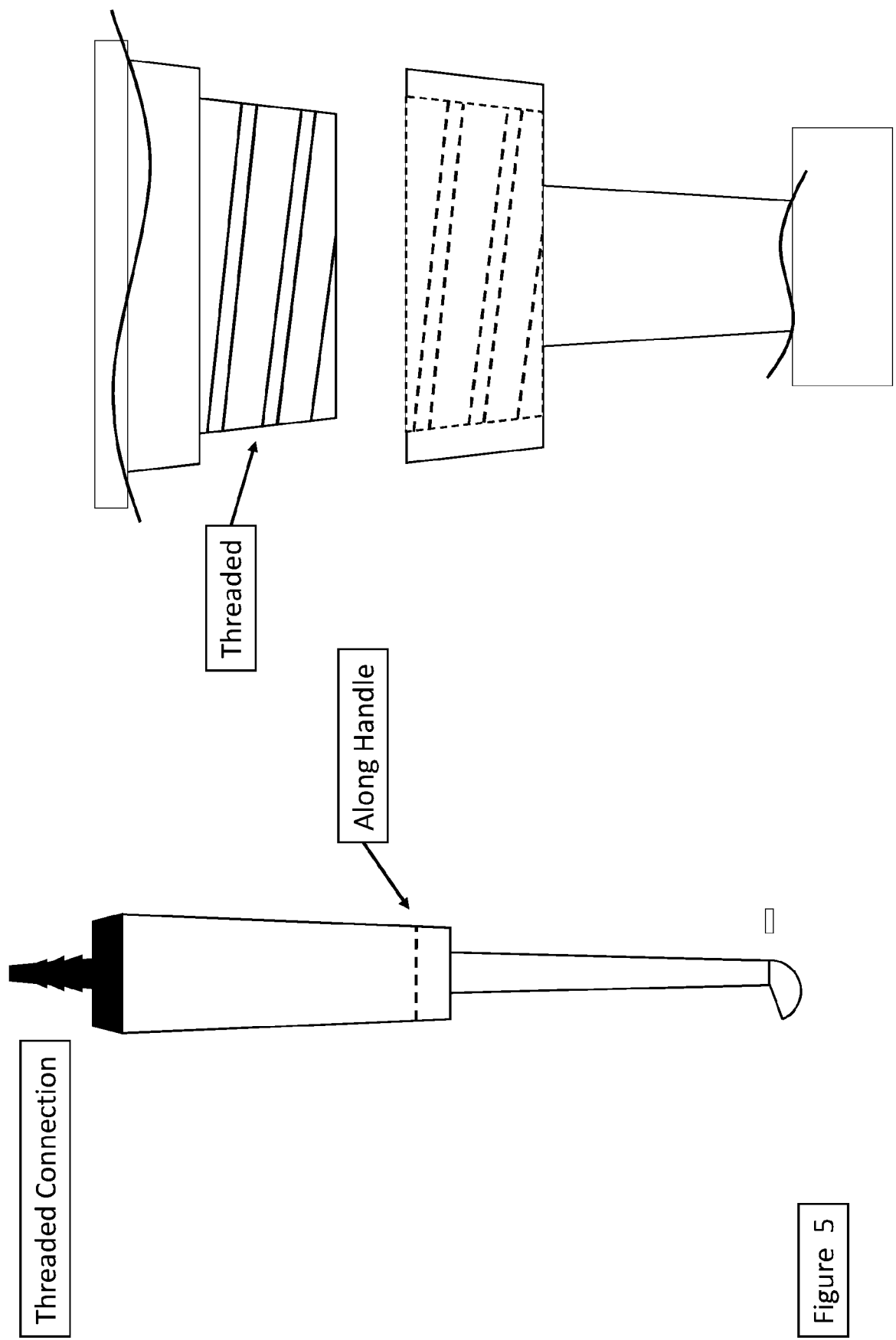
FIG. 5 schematically depicts a further exemplary connection feature according to the present disclosure.

FIG. 5 depicts an embodiment of a connection feature between the shaft and the suction canister. In this embodiment, the shaft contains a proximal feature with threads, and the suction canister contains a distal feature with threads. The components are connected by threading the shaft onto the suction canister, an air-tight connection may be created through a rubber-like material between the two components. Alternatively, the shaft may be permanently joined to the suction canister at some point along the length of the canister through ultrasonic welding, adhesive or other bonding processes.

FIG. 6a depicts an embodiment of a connection feature between the shaft and the suction canister. In this embodiment, the shaft contains a protruding pin feature at the proximal end of the shaft. The suction canister contains a distal slotted-gate which is toleranced to fit the pin feature. The components are connected by aligning the pin feature to the slotted-gate, inserting the shaft into the suction canister, and then twisting the shaft in the direction of the slotted-gate to lock the pin in. This embodiment may employ a reversible or irreversible connection. An air-tight connection may be created through a rubber-like material between the two components.

FIG. 6b further describes the embodiment in FIG. 6a, with the added feature of a hooked slot. In this embodiment, the slotted-gate contains two perpendicular turns. A release button is incorporated to prevent the pin from reversing out of the slotted-gate unless the button is activated to release the pin. This enables the shaft to remain in position without separating from the suction canister during use of the instrument. An alternative configuration of this design would entail a snap feature that allows the pin to lock into place.

FIG. 7a depicts an embodiment of a connection feature between the shaft and the suction canister. In this embodiment, the suction canister contains a magnetic collar whose inner diameter is larger than the diameter of the shaft. The magnet further comprises a sliding feature protruding out of the suction canister wall which enables a user to slide the magnet proximally within the suction canister. The components are connected by inserting the shaft through a hole in the suction canister with the magnetic collar sitting at the distal base of the suction canister. A magnetic force created between the inner wall of the magnetic caller and the outer wall of the shaft holds the shaft in place. To disconnect, a user slides the magnet proximally while pulling the shaft out of the distal hole of the suction canister to disengage the magnetic connection. An air-tight connection may be created through a rubber-like material or mechanical connection between the shaft and suction canister or through interference between the shaft and receiving end of the suction canister.

FIG. 7b depicts an embodiment of a connection feature between the shaft and the suction canister which uses an external magnetic collar. In this embodiment, the collar sits outside of the suction canister and is wholly or partially rotatable. The collar is only magnetized through a portion of the circumference, thereby having a magnetic region and a non-magnetic region. The suction canister further has a pin embedded in the inner wall of the canister which has a protruding state and a recessed state, through a spring mechanism, for example (FIG. 7c). The shaft has a female groove feature on its proximal end which can accept the pin in its protruding state to lock the shaft in place. To remove the shaft from the suction canister, the external collar is rotated to bring the magnetic region closest to the pin, thereby pulling the pin into its recessed state and unlocking the shaft (FIG. 7c). An air-tight connection may be created through a rubber-like material or mechanical connection between the shaft and suction canister or through interference between the shaft and the receiving end of the suction canister.

FIG. 8a depicts an embodiment of a connection feature between the shaft and the suction canister. In this embodiment, the shaft contains female grooves circumferentially at its proximal end. A series of ball bearings embedded within the suction canister protrude into the female grooves of the shaft to hold it in place; a collar around the outer wall of the suction canister compresses the ball bearings into the grooves of the shaft. To release the shaft, the collar slides proximally along the suction canister to decompress the ball bearings, and the shaft is pulled out of the distal end of the suction canister. Air tight connection is achieved through a rubber-like material between the shaft and the receiving end of the suction canister or through a mechanical connection between the two.

FIG. 8b presents a similar concept where a protruding element engages with a receiving end in the shaft. In a connection that is non-removable, one or more protruding elements insert into a receiving feature of the shaft. An alternate configuration features one or more protruding elements (i.e., a pin) that can be disengaged from the male-female joint formed between the element and the shaft through connection to an externally communicating feature that engaged the protruding element to engage or disengage with the shaft.

FIG. 9 displays three different release mechanisms which may be triggered to release the shaft from the suction canister in, for example, any of the aforementioned embodiments. The release mechanism may be triggered, for example, by a push-button (left), a pull-tab (middle), or a twist-knob (right).

Figure 10A:
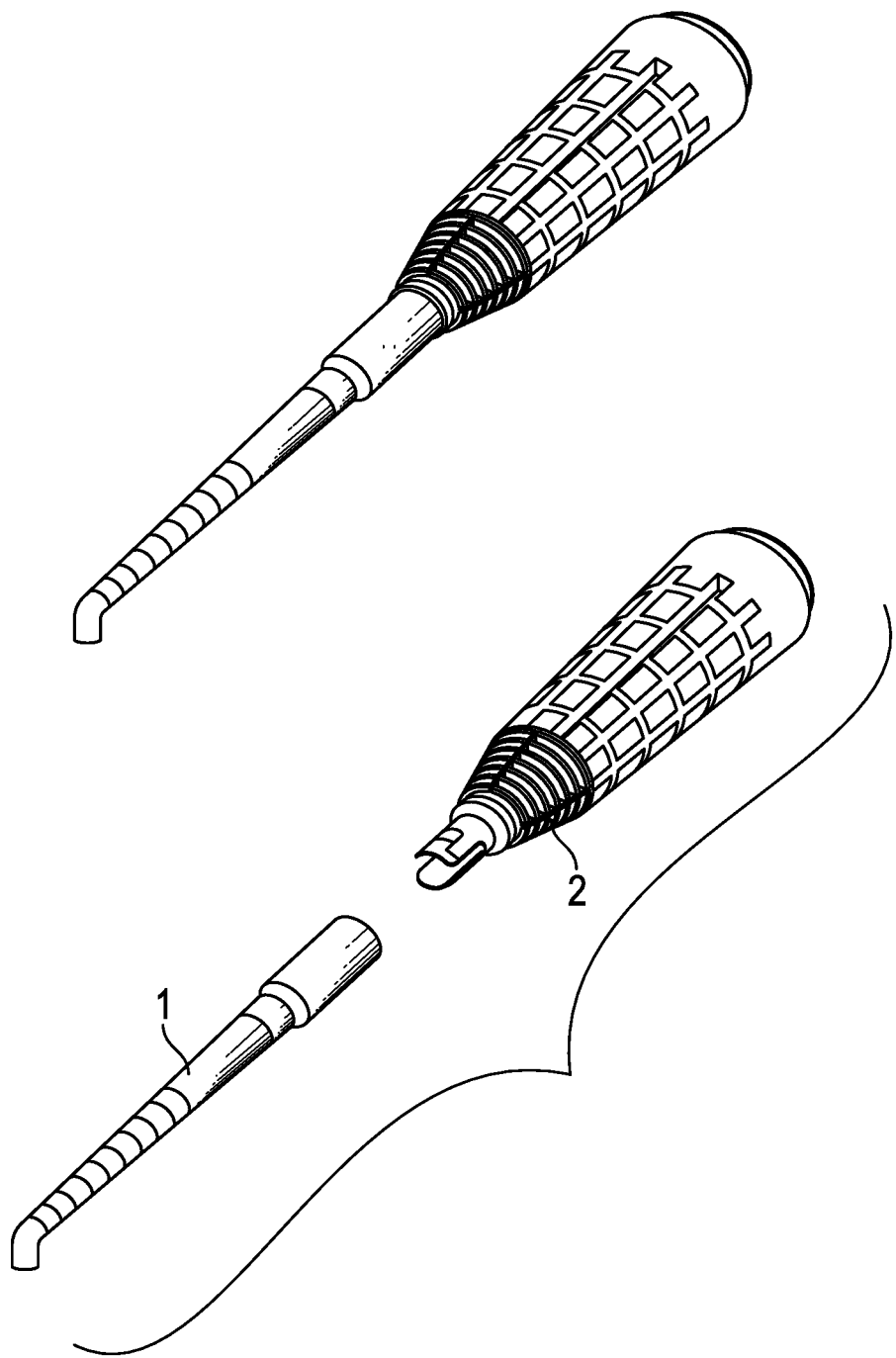
FIGS. 10a and 10b schematically depict a non-removable snap fit connection feature according to the present disclosure.
Figure 10B:
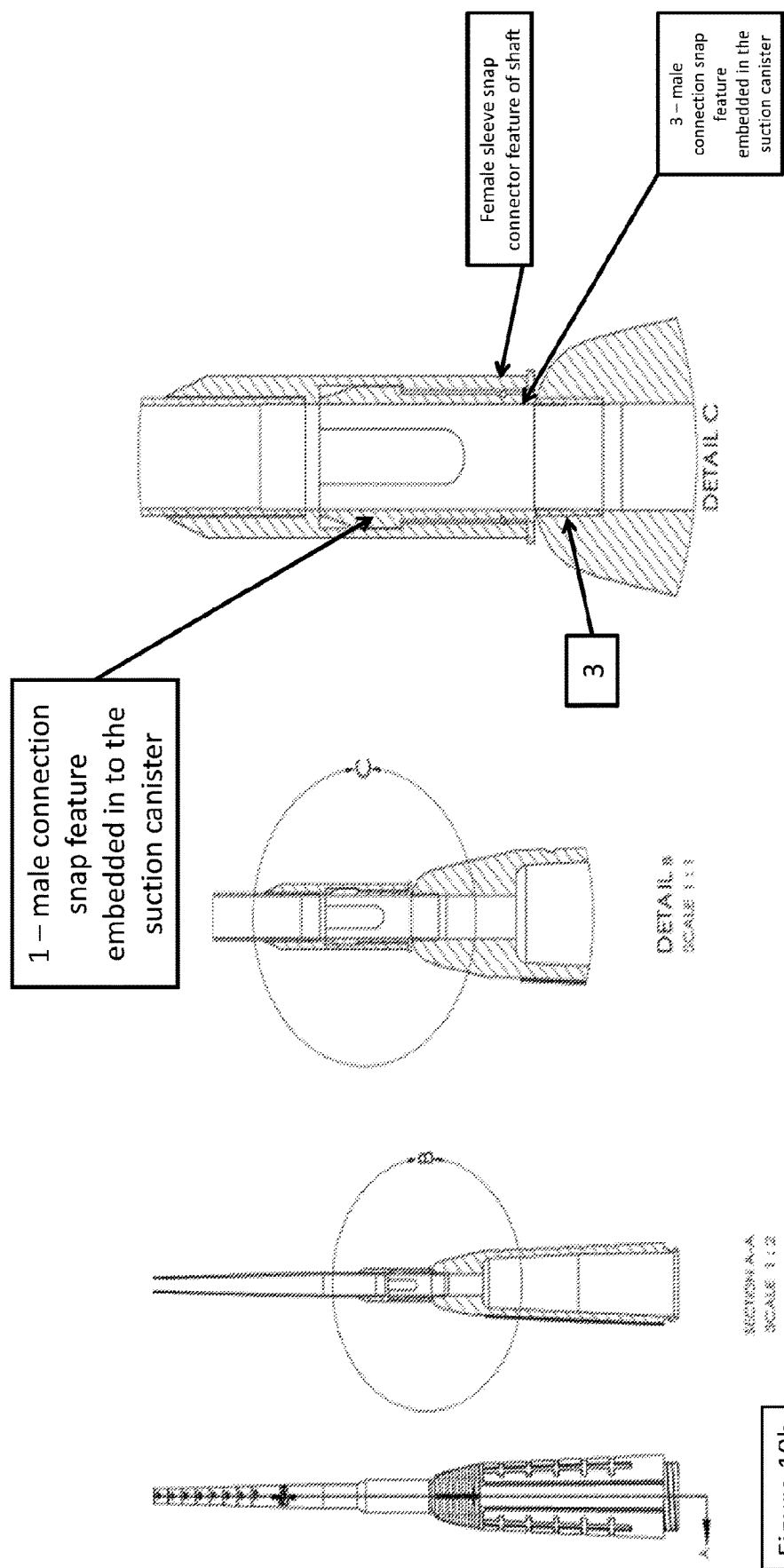

FIG. 10a depicts a permanent non removable snap fit connection. FIG. 10b further details this embodiment. Embedded in the suction canister is an intermediate mating feature. A connection sleeve is attached to the shaft with a female snap feature that connects to the male snap feature that is embedded in the suction canister. The female sleeve locks over the male connector and establishes an air tight seal with a rubber seal between the male and female connectors. This enables the translation of tension and compression and torque to the shaft.

Figure 11A:
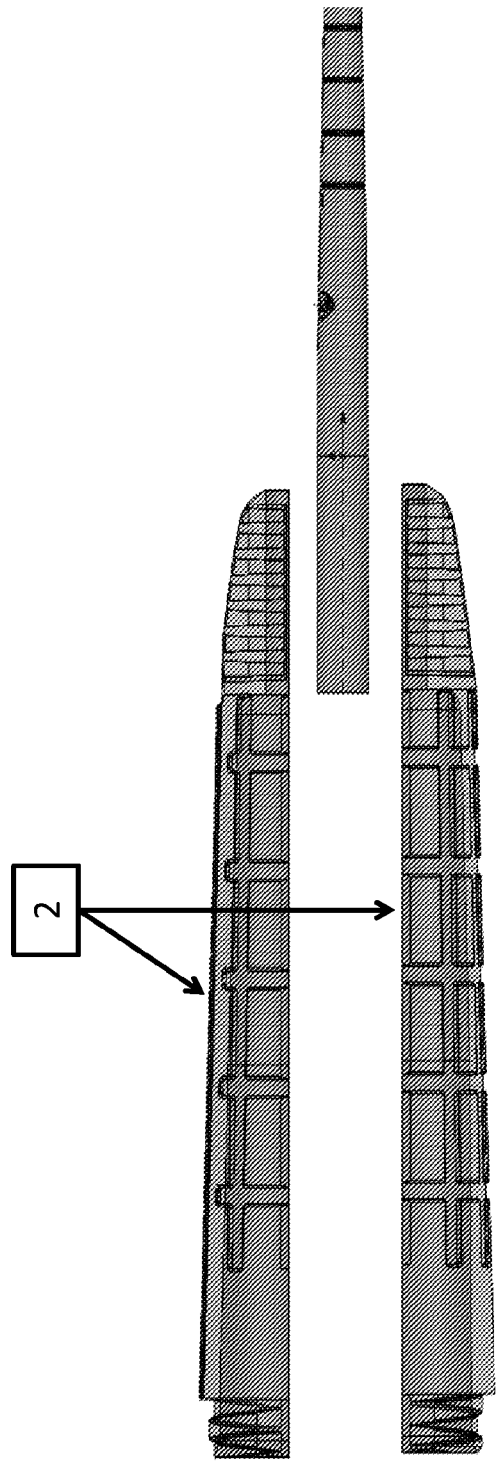
FIGS. 11a and 11b schematically depict an exemplary connection feature that utilizes connecting halves according to the present disclosure.

FIG. 11a establishes an alternate embodiment to connecting the shaft to the suction canister whereby the container is two halves and assembled over the shaft. Several configurations within this are established herein. For example, the halves may be joined over the shaft through the use of an adhesive to bond the surfaces together. This may be done in combination with geometric features that assemble like a puzzle piece over the metal shaft.

Figure 11B:
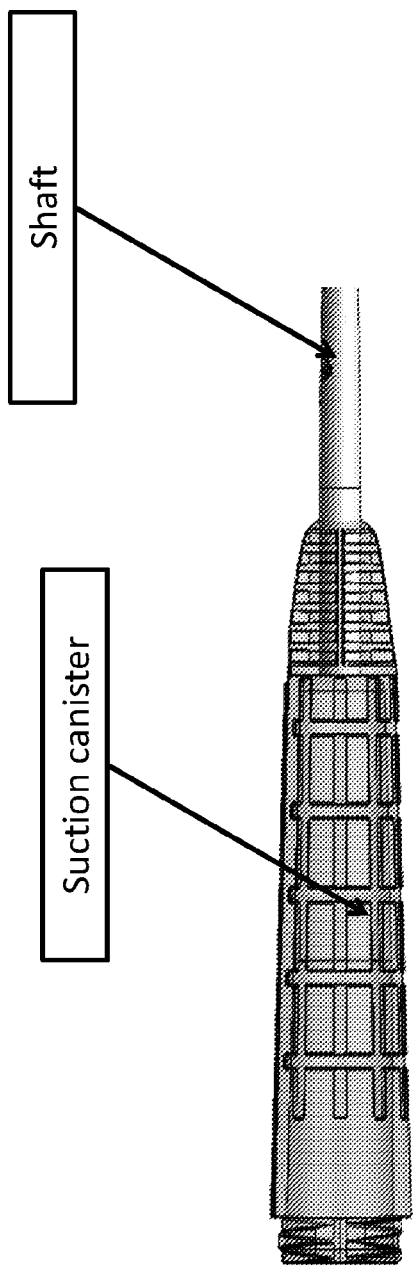

FIG. 11b shows the ending result of two halves of the canister assembled over a shaft. The two halves could be joined and assembled over the shaft via many processes including, but not limited to, an ultrasonic welding process, heat shrinking, adhesive, hot plate weld, or laser weld, where the two halves create a bond between the two surfaces over the shaft.

Alternatively, FIG. 11b can form a junction whereby the shaft is superheated and staked into the suction canister that is composed of a material with a melting point less than that of the shaft. Once the shaft cools, the material solidifies forming an air tight bond against the surface of the shaft. An alternative approach can be implemented whereby the portion of the suction canister that is connecting to the shaft is heated to be malleable to allow expansion to accept the shaft into the joining hole and then either a heat shrink, or a compression process with rapid cooling takes place to solidify the joint between the shaft and the suction canister. An alternative embodiment could feature a stake operation where there is a friction feature on the shaft such as a grip blast or knurl pattern and it is friction fit into the receiving end of the suction canister creating a feature where the shaft cuts into the suction material to create a friction fit between both components. Lastly, a stake operation with an adhesive can form the bond between the two.

Figure 11D:
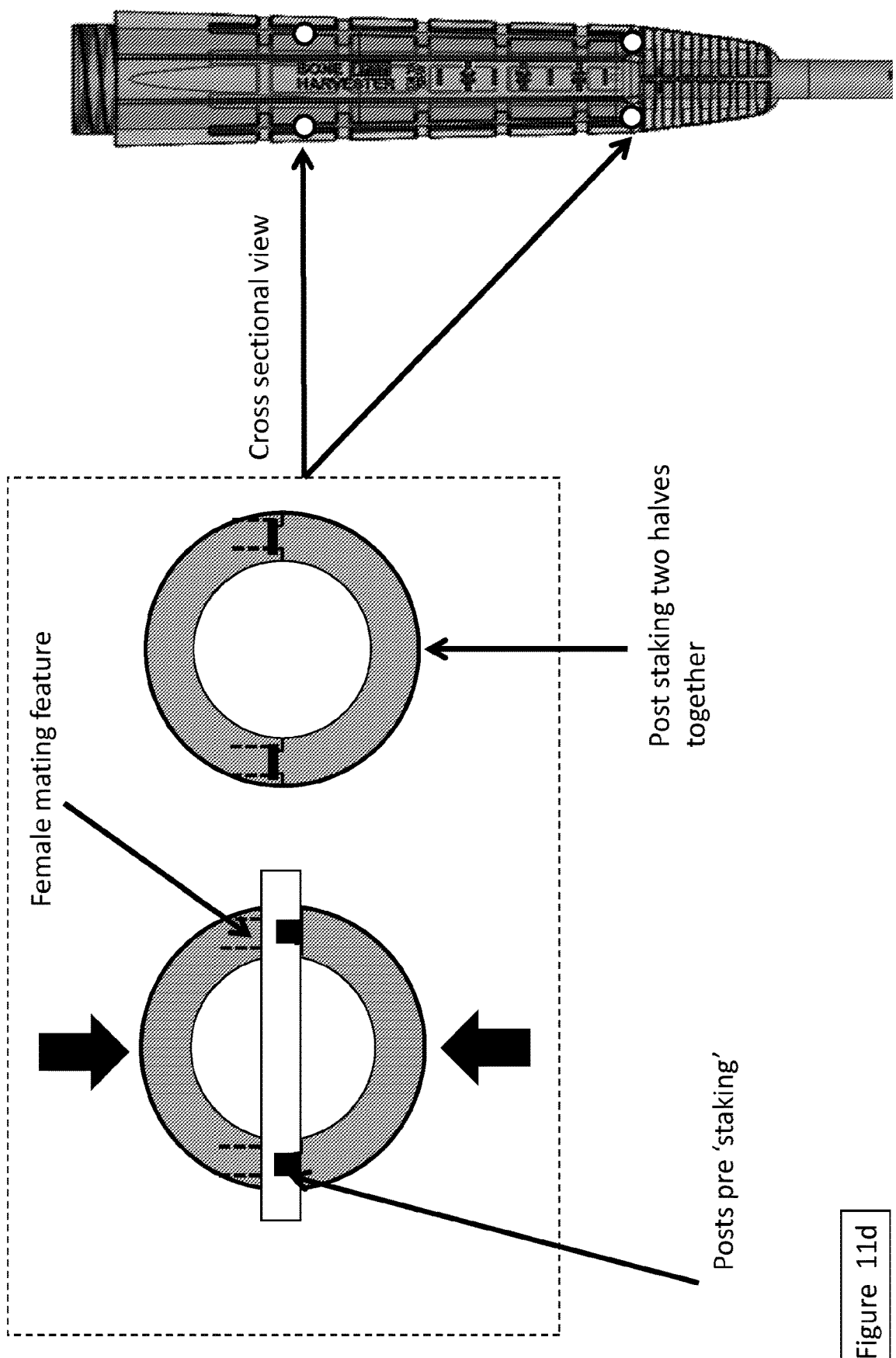

FIG. 11c presents a suction canister constructed of two halves that join together over the shaft. The posts shown in FIGS. 11c and 11d are similar to pegs that protrude as a male connection from one half of the suction canister embodiment. The second half contains female receiving ends to thread the posts through. Once assembled over the shaft the pegs are deformed to expand in one direction and compress in the other. The expansion can be accomplished through the application of energy to the surface to generate a compression effect to the posts to lock the connection together. An air tight seal can be formed around the perimeter of the suction canister through a friction fit between the surfaces between the halves coming together. Alternatively there may be a rubber-like gasket layer placed in between the halves prior to heat staking together the posts to create an air tight seal.

Figure 11E:
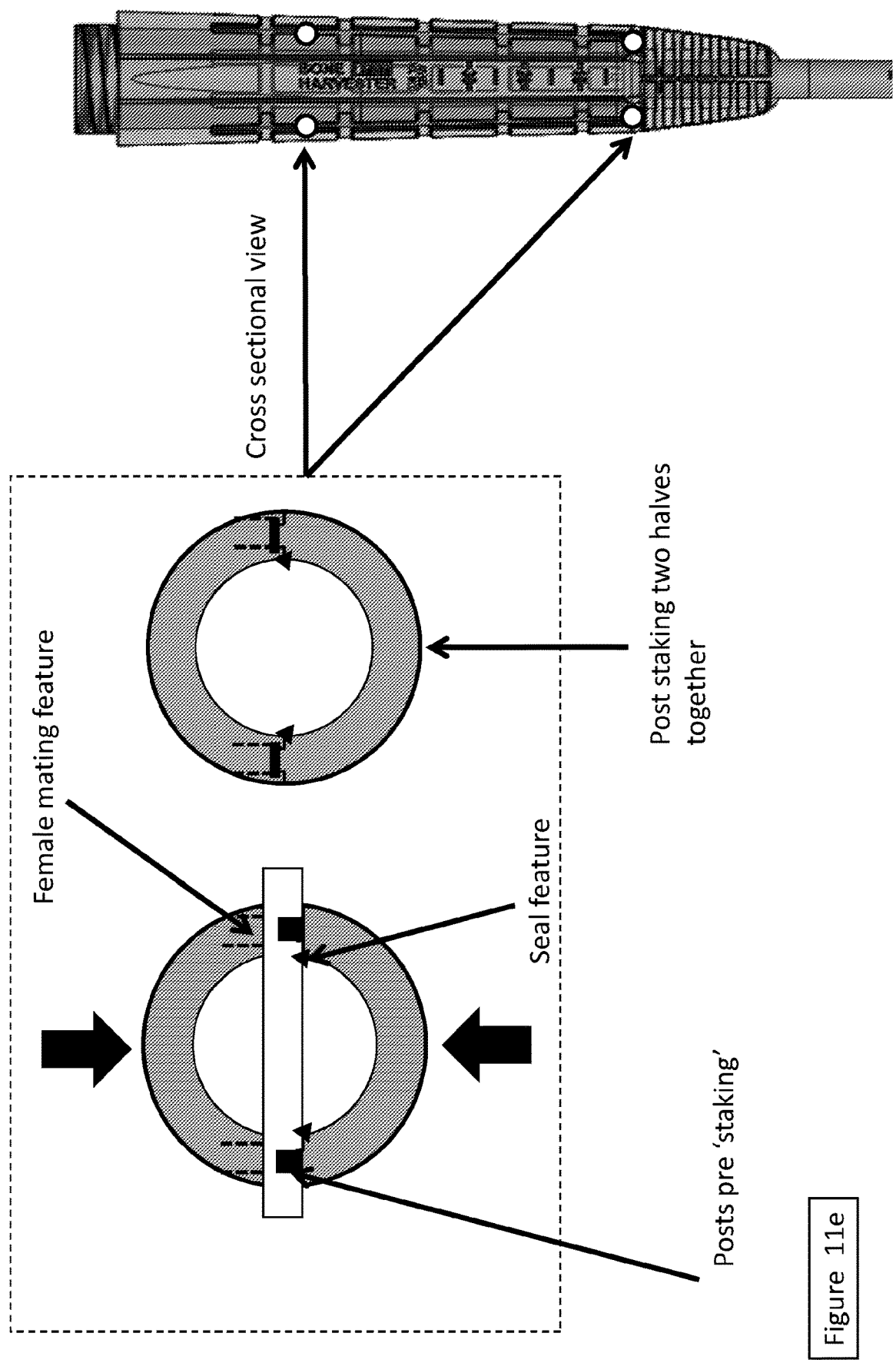
FIGS. 11e and 11f schematically depict an exemplary seal feature according to the present disclosure.
Figure 11F:
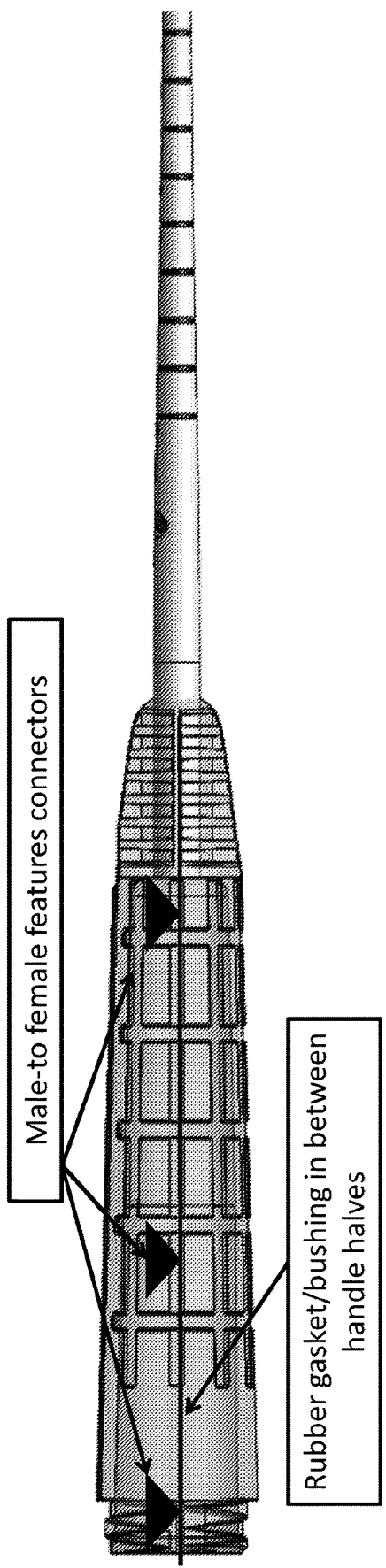

Lastly, FIG. 11e depicts a seal feature that is a geometric feature built into the surface at the joining feature such that when the two halves join together, a seal is formed by pressing the top half to the bottom half through a chamfered lip or rim that extends along the perimeter of the part line. Another alternative embodiment is joining the two halves over the shaft through male-to-female snap fit connection features between the halves (FIG. 11f). In this embodiment, an air tight seal can be applied through friction fit between the halves, through a rubber gasket/bushing that sits between the two halves or through a friction fit between a lip feature that is pressed against to form the air tight seal. This can also be achieved with screw pins at the same locations shown in FIG. 11f.

Figure 12B:
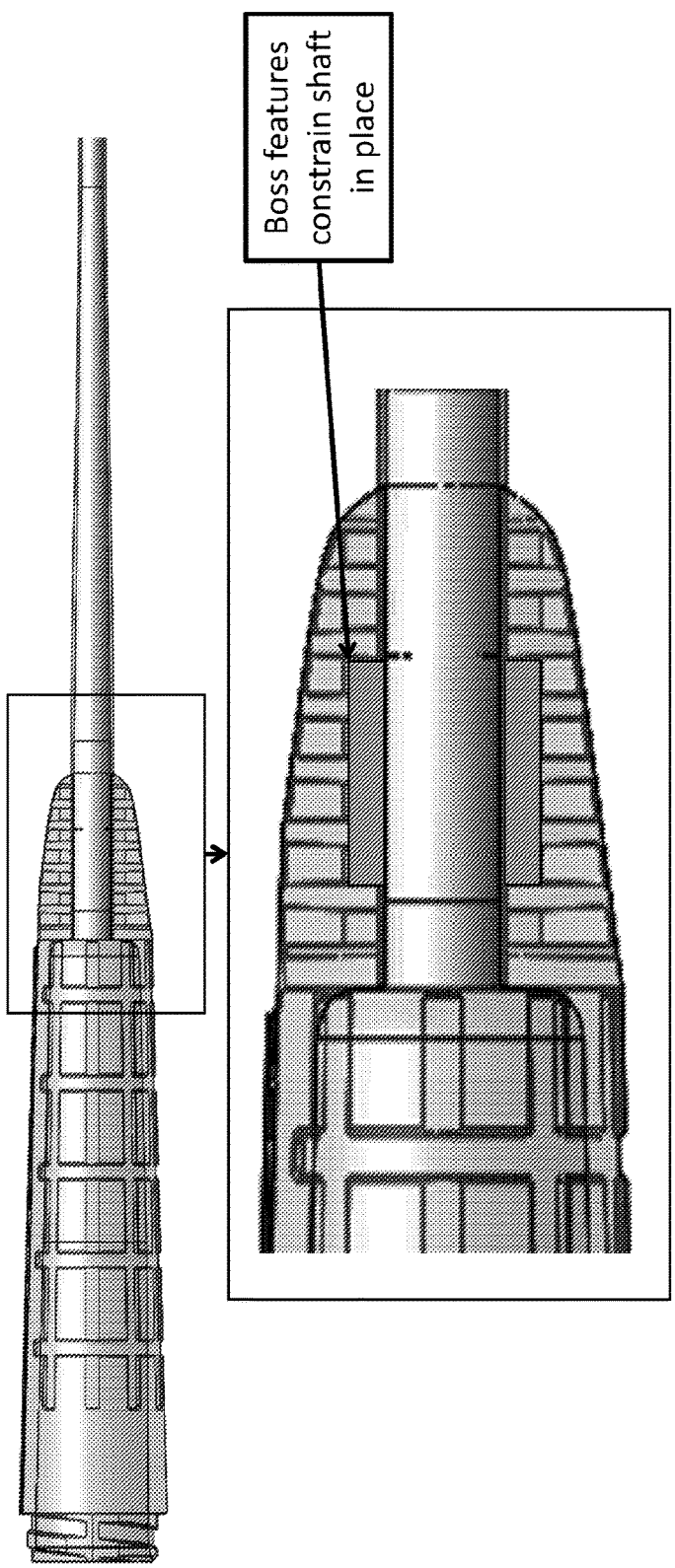
Figure 12C:
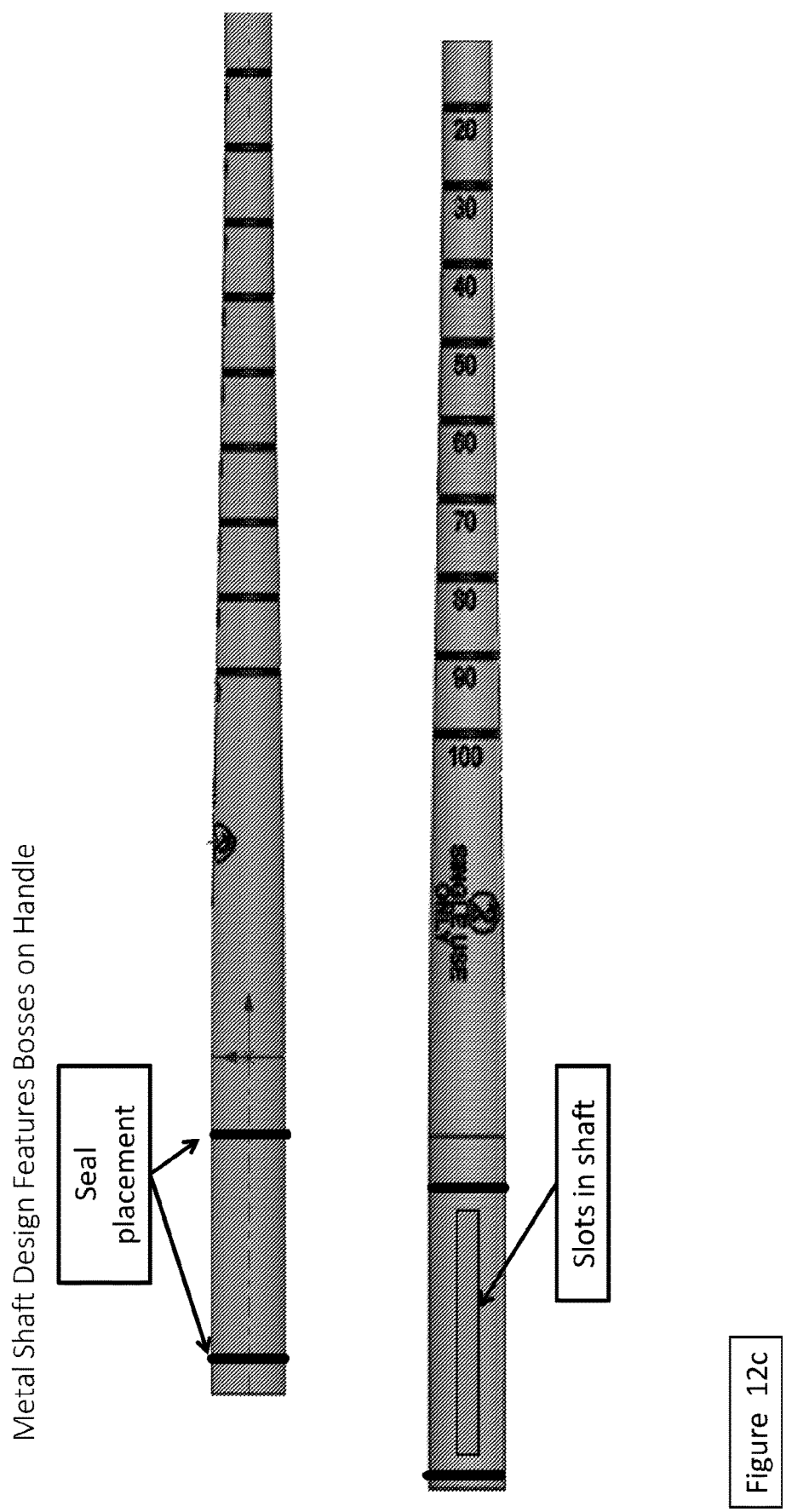
FIGS. 12c and 12d schematically depict a further exemplary connection feature according to the present disclosure.
Figure 12D:
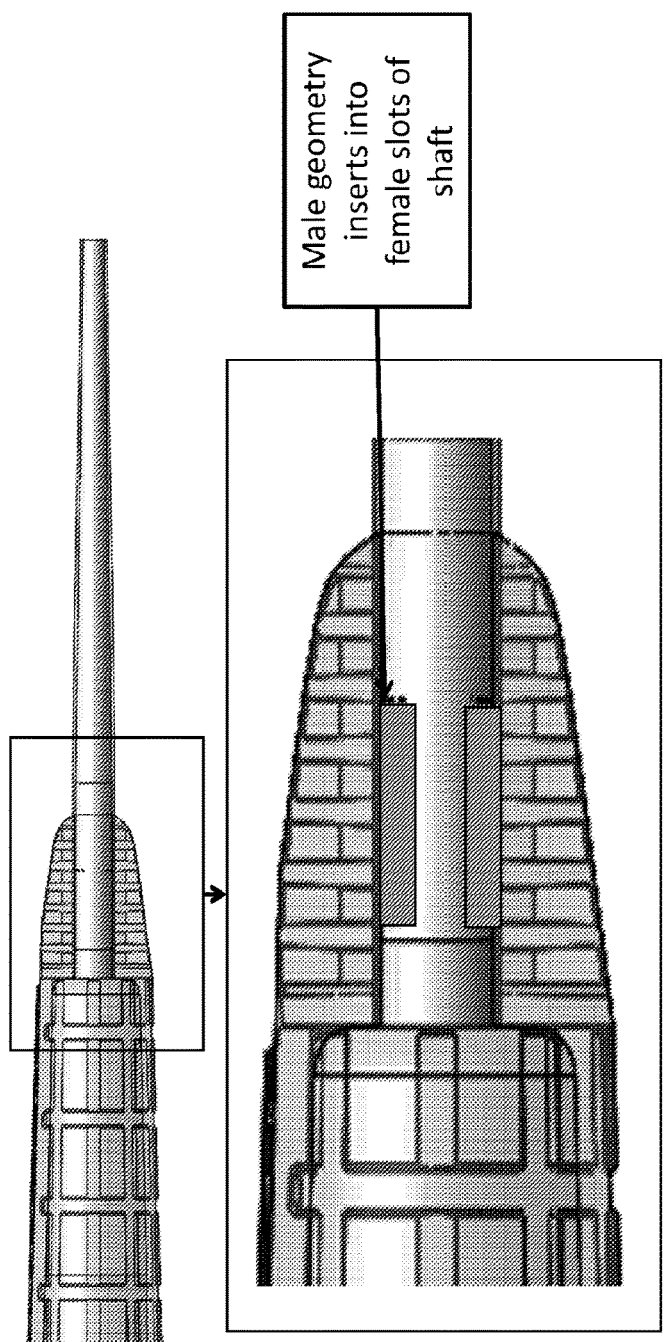
Figure 12E:
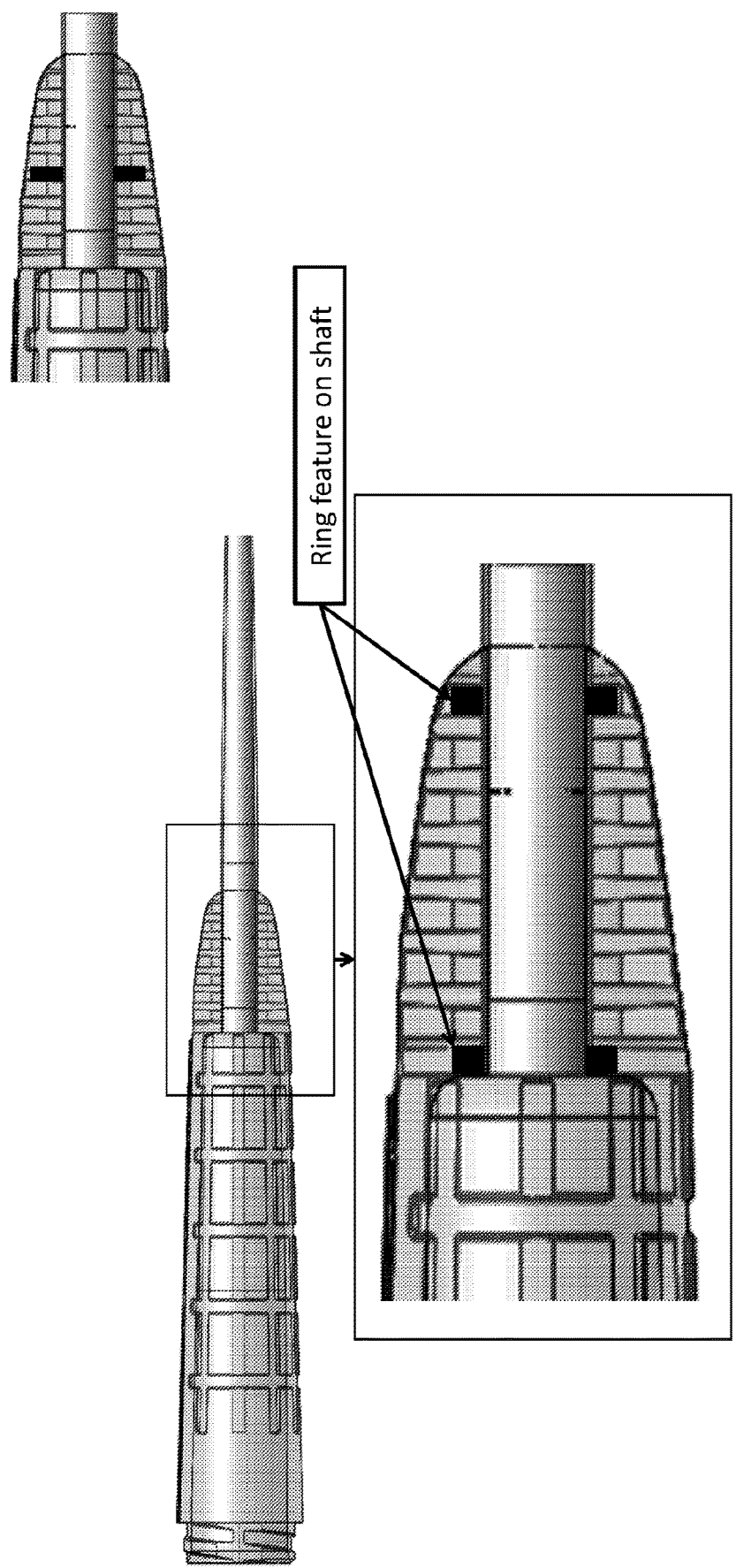
FIG. 12e schematically depicts a further exemplary connection feature according to the present disclosure.

Along with any of the aforementioned assembly configurations of the suction canister over the shaft, this can be done in conjunction with different mating features for the shaft. FIG. 12a displays a shaft with a boss feature that is the male fitting to the female connection end of the suction canister. Once assembled, FIG. 12b displays the boss feature inserted in the handle. Seals could be formed proximal or distal or at both locations to the boss feature shown. An alternative configuration is described in FIGS. 12c and 12d where the reverse is achieved with the suction canister housing the male feature to the female connection feature on the shaft. The mating slots can be any shape and enable the translation of torque, tension, compression and bending to the shaft while maintaining an airtight connection. An alternative male geometry on the shaft is shown in FIG. 12e. One or more ring features can protrude radially from the surface. The rings can be interrupted or continuous around the circumference of the shaft. The protruding rings can have a cross section shape of a circle or any polygon housing more than one flat side. There can be at least one ring feature along the connection portion of the shaft.

Figure 13B:
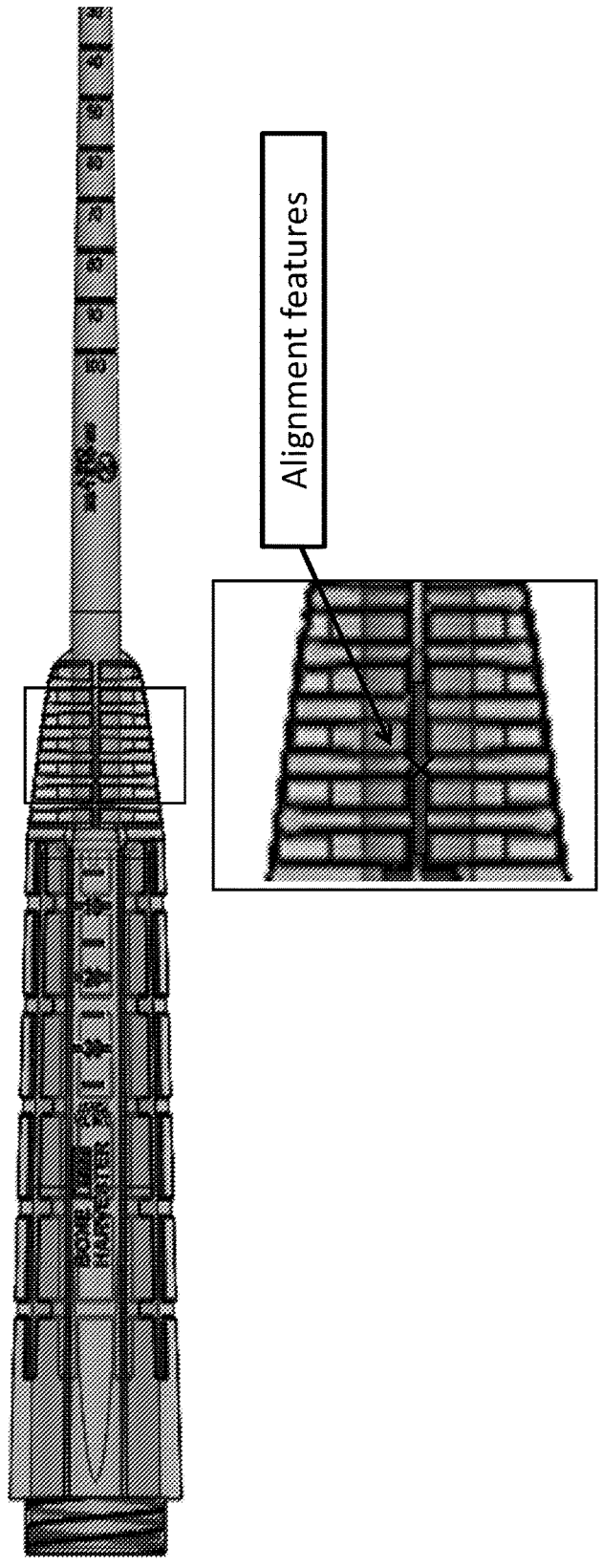

FIG. 13a is an embodiment with a handle collet based assembly. The canister has a male/female connection feature that fluidly connects to a collet feature to securely attach a shaft. The shaft would be placed into the receiving end of the suction canister and a collet feature threads over the shaft and fluidly secures to the suction canister to assemble to a secure single assembly. Between the collet and the suction canister a seal feature is implemented. This may be in the form of a rubber O-ring, or through geometric interference or adhesive. A second seal feature is found between the shaft and either the suction canister or the collet feature which can be configured with any of the aforementioned seal features. The collet can fluidly connect to the suction canister through any of the aforementioned methods of creating a permanent joint or temporary joint that can be disassembled between the components (e.g., adhesive, snap fits, screws, vibration, welding, etc.). FIG. 13b displays the assembled embodiment. Additional configurations feature alignment features or visual indicators indicating a complete assembly between components. For example, superficial arrows can be implemented which align once threads are completely secured. The metal shaft may contain any combination of the aforementioned boss features that can be used to securely attach the metal shaft to enable translation of torque, compression, tension and bend forces to the shaft.

Figure 14C:
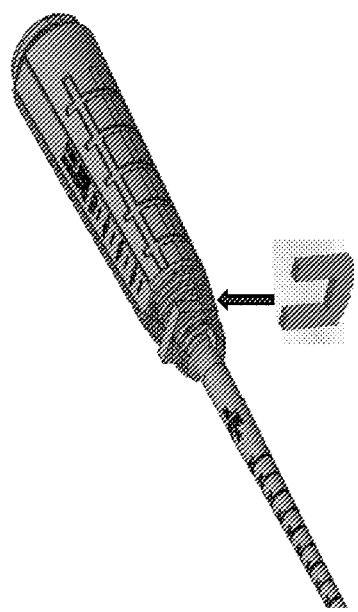
FIG. 14c schematically depicts a further exemplary assembly in which disengagement may be effectuated using an accessory according to the present disclosure.
Figure 14D:
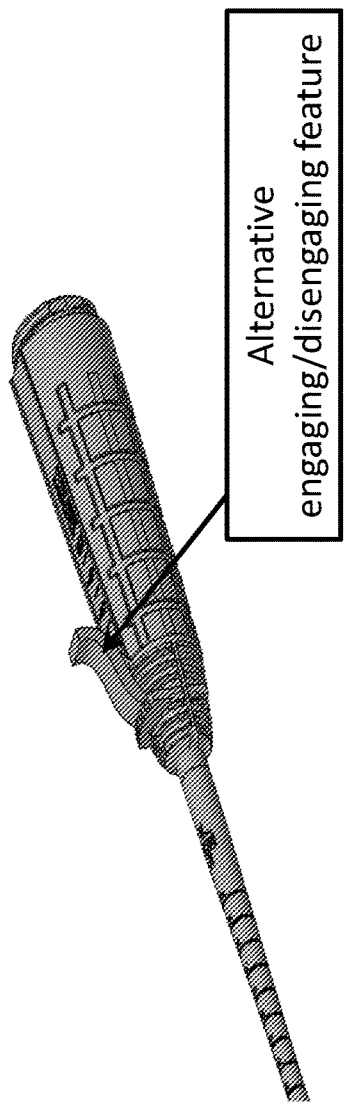
FIG. 14d schematically depicts a further exemplary embodiment wherein a finger-grasp geometry is assembled to a lateral attachment according to the present disclosure.

FIG. 14a presents an embodiment where the shaft has peg features that radially protrude from the shaft surface and can be used to key into the female slot feature of the suction canister. Once the shaft is threaded through, a C-clip component or lateral attachment is inserted orthogonal to the central longitudinal axis of the shaft to secure the shaft in place. The C-clip attachment may snap onto the peg features of the shaft, or securely attach to receiving features via a snap fit or other mechanical connection on the receiving end of the suction canister. This connection may be temporary or permanent. This embodiment can be assembled permanently with the use of any of the aforementioned connection methods for joining two surfaces together. FIG. 14b displays the lateral attachment assembled into place to secure the shaft to the suction canister receiving end. FIG. 14c depicts an alternate configuration in which the assembly can be disengaged with the use of an auxiliary accessory that engages with the lateral attachment to break the connection and release the shaft from the suction canister. FIG. 14d present an alternative embodiment in which a finger-grasp geometry is assembled to the lateral attachment, which may improve usability of engaging and disengaging the shaft from the suction canister.

Figure 14E:
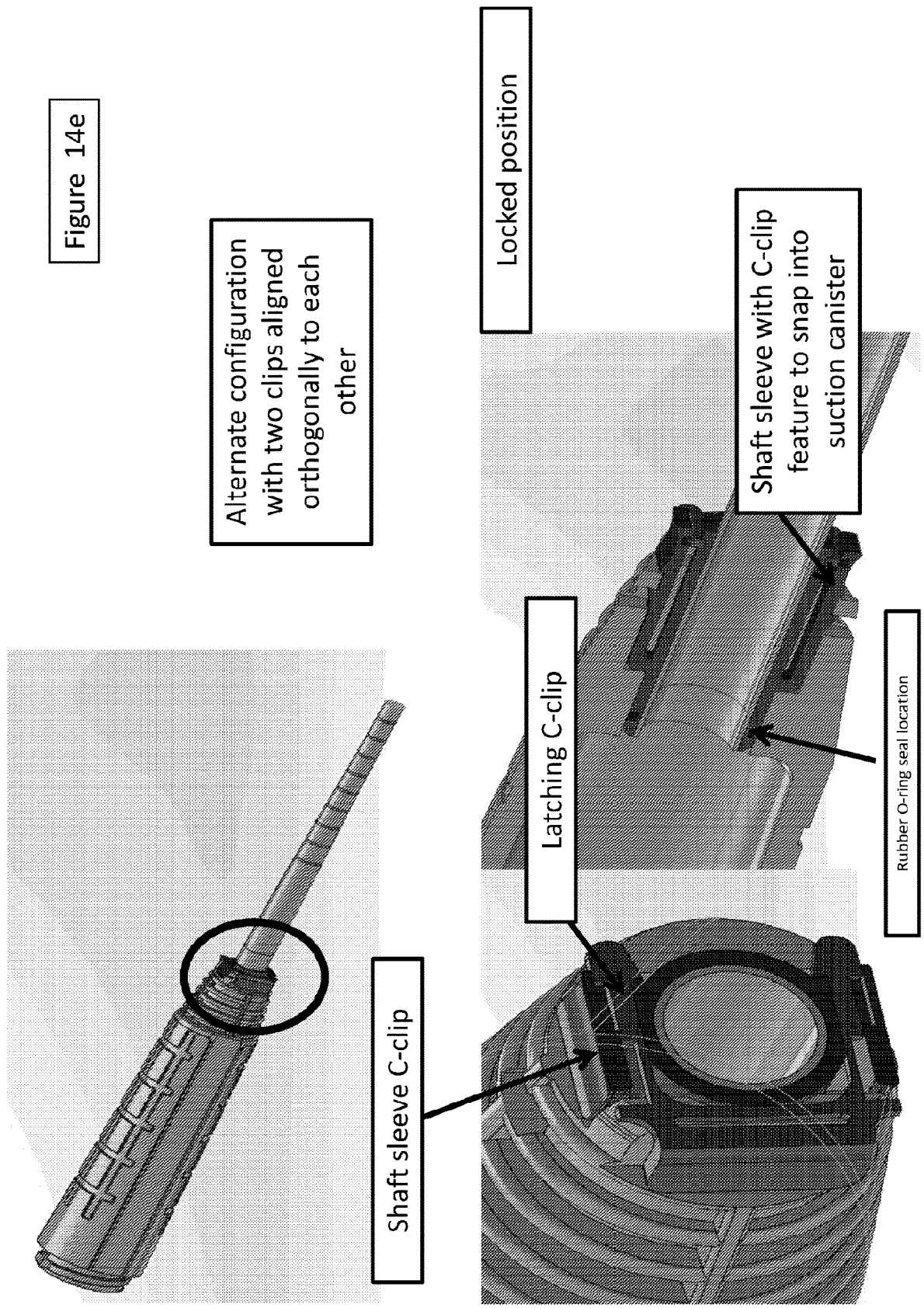

An alternative configuration is shown in FIG. 14e, which features two clips that are oriented orthogonally to each other. The first C-Clip is permanently attached as a sleeve onto the shaft and has sealing features either in the form of a rubber O-ring or through interference geometry fits that force compressible material to form an air-tight seal such as a chamfer at the proximal most end of the shaft assembling with a feature on the suction canister entry hole. The shaft sleeve C-clip snaps into place with a female geometry receiving end in the handle. Once secured in the suction canister, a latching C-clip is inserted orthogonally to the shaft sleeve C-clip. This latching C-clip can be made removable or permanent. In a removable configuration, pressure is applied to the latching C-clip to disengage as shown in FIG. 14f. Once disengaged, the shaft can be removed from the suction canister enabling the attachment of a different shaft or repurposing of the suction canister for other uses. The latching C-clip secures the shaft sleeve C-clip to prevent accidental disengagement during the use of the device. Lastly, in the permanent configuration, the second C-clip can be mechanically permanent or adhered to the assembly.

Figure 15C:
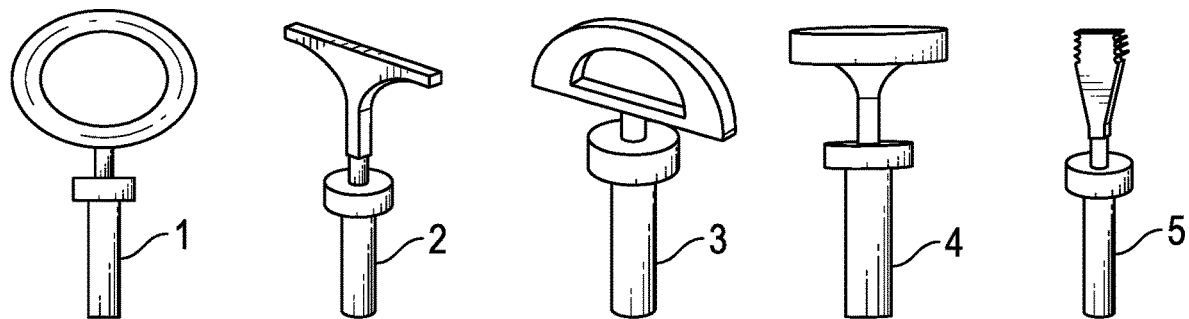
FIG. 15c schematically depicts different geometries that may be associated with a crosspin feature according to the present disclosure.
Figure 15D:
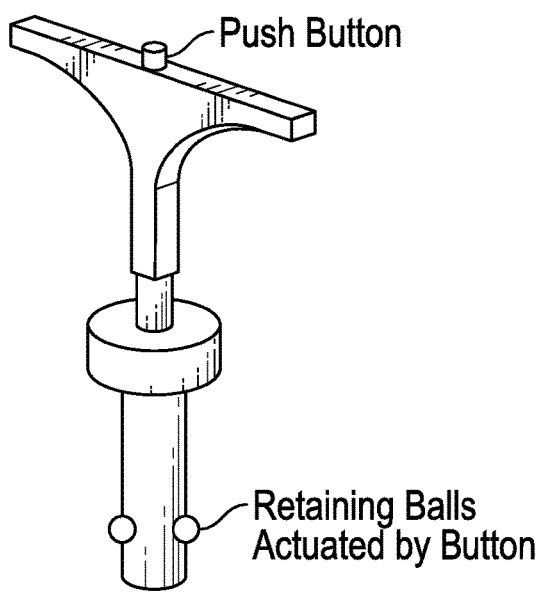
FIG. 15d schematically depicts an exemplary release mechanism according to the present disclosure.

FIG. 15a presents an embodiment featuring a connection between the shaft and the suction canister through the use of one or more cross pins that thread through the walls of the shaft and surrounding wall of the suction canister. Seals can be achieved through friction fit between the pin and surrounding material or through rubber seals. Alternatively, adhesive or other bonding agent can be placed in the resulting dimples to seal both openings that allow visual access to the cross pin. There can be a seal between the shaft and the suction canister through the use of an intermediary rubber material, or through friction/interference fit. This connection can either be permanent or temporary. Any of the aforementioned permanent attachment methods can be adapted to the cross pin. FIG. 15b establishes the same concept with a different pin embodiment that enables removal of the pin in order to allow the user to disengage the shaft. FIG. 15c further elaborates on different geometries that the cross pin may feature. A release mechanism as shown in FIG. 15d can be used on the cross pin for ease of removal of the cross pin. Seals can be made with the cross pin through an O-ring on the shaft, or through friction fit of material or through a permanent means of sealing the space between the components as shown in FIG. 15e.

Figure 16B:
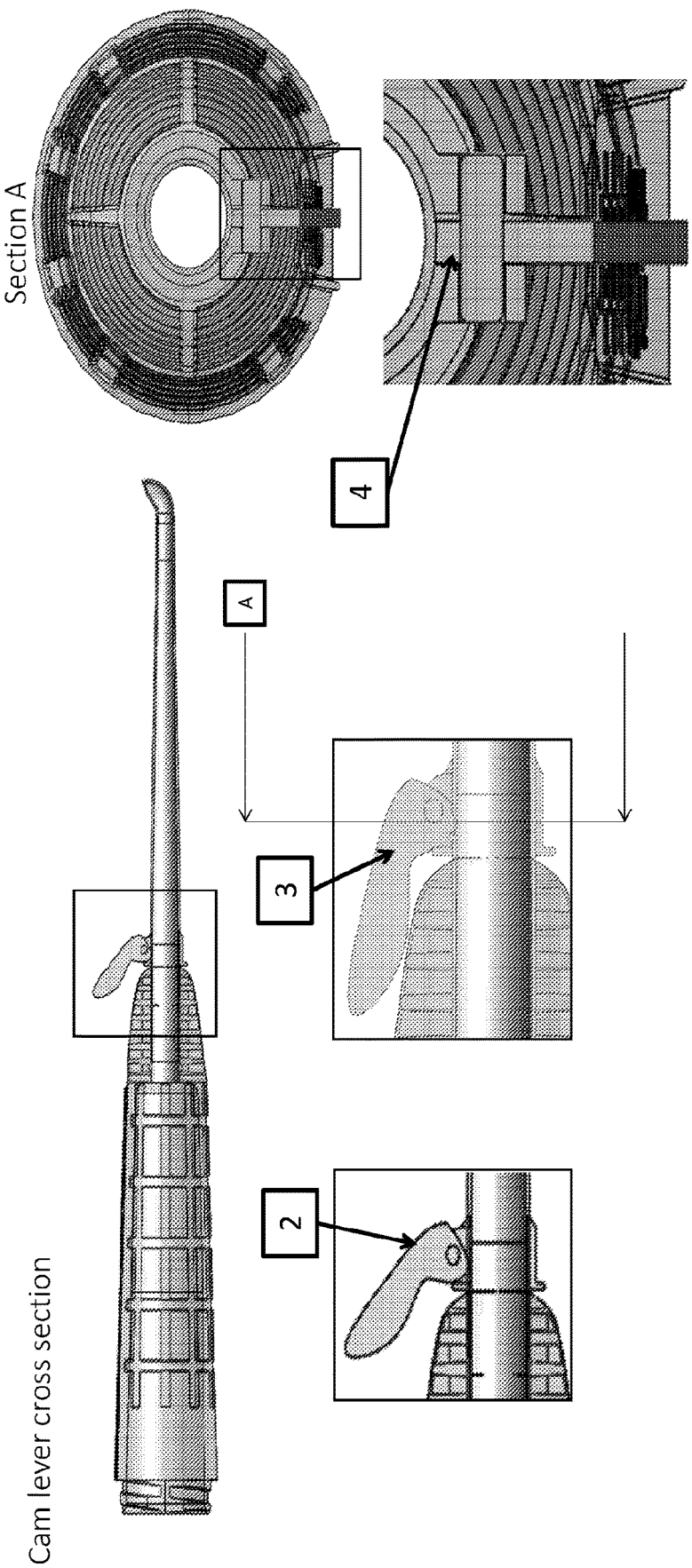

FIG. 16a presents an embodiment that features a cam slot joining feature between the shaft and suction canister. This enables a temporary joint to be formed to engage and disengage with the shaft, allowing the user to attach and reattach different shafts to the same canister unit. The cam slot features a lever mechanism that slides into a female feature located on the metal shaft. The cam slot enters the female feature on the metal shaft orthogonally to the longitudinal central axis. FIG. 16b further elaborates on this connection mechanism. The cam lever compresses to secure the tube into location. The slot feature between the cam lever and shaft will constrain the shaft. Air tight seals can be formed between any combinations of the components using aforementioned features.

Figure 17:
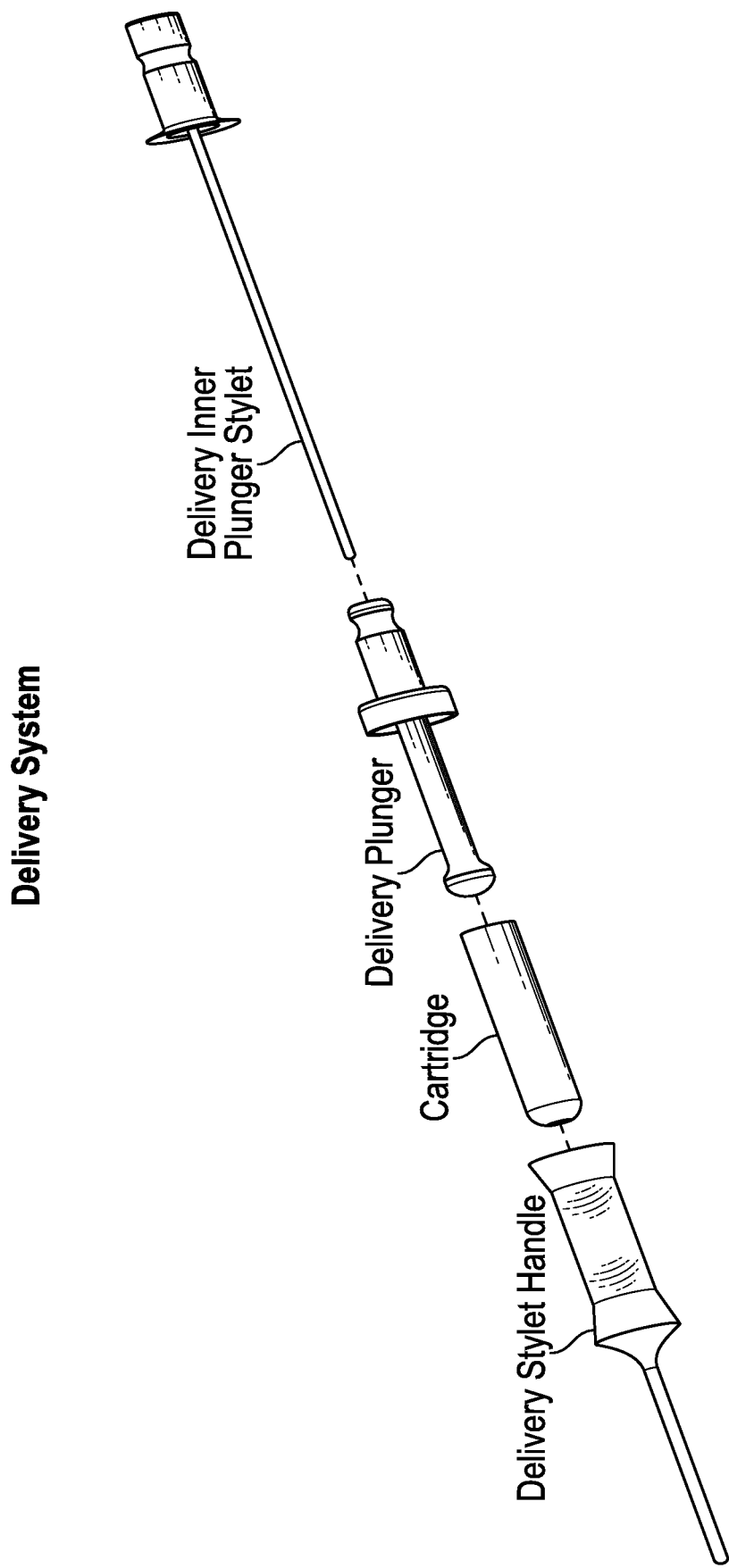
FIG. 17a schematically depicts an exemplary tissue delivery system according to the present disclosure.

FIG. 17a depicts a tissue delivery system. Any of the aforementioned connection methods can be implemented in this embodiment. In the depicted embodiment, a delivery cannula is assembled to the suction canister reservoir where the tissue is collected. A separate plunger can attach to the system and enable the delivery of the collected tissue. This plunging mechanism would linearly translate along the central axis, pushing the collected material down the cannula and into the delivery location.

In addition to the advantageous and exemplary connection features and mechanisms described above, for ease of use to the surgeon, it may be advantageous to provide a collection tool that can manipulate the volume of tissue collected while using a tissue collection instrument. This may be done to restrict total volume of the collection chamber in a way that allows for continuous suction flow rate to take place while collecting the desired amount of tissue. Often, tissue can splatter inside a collection chamber, creating situations in which the volume of tissue collected is difficult to read. Containing the tissue to a pre-set volume can enable a user to effectively ascertain the volume of tissue collected.

The following figures pertain to mechanism(s) internal to a suction canister that has at least one inlet and at least one outlet where suction is applied to the outlet drawing tissue material through the inlet with intent of the tissue material being collected inside the canister.

Figure 18:
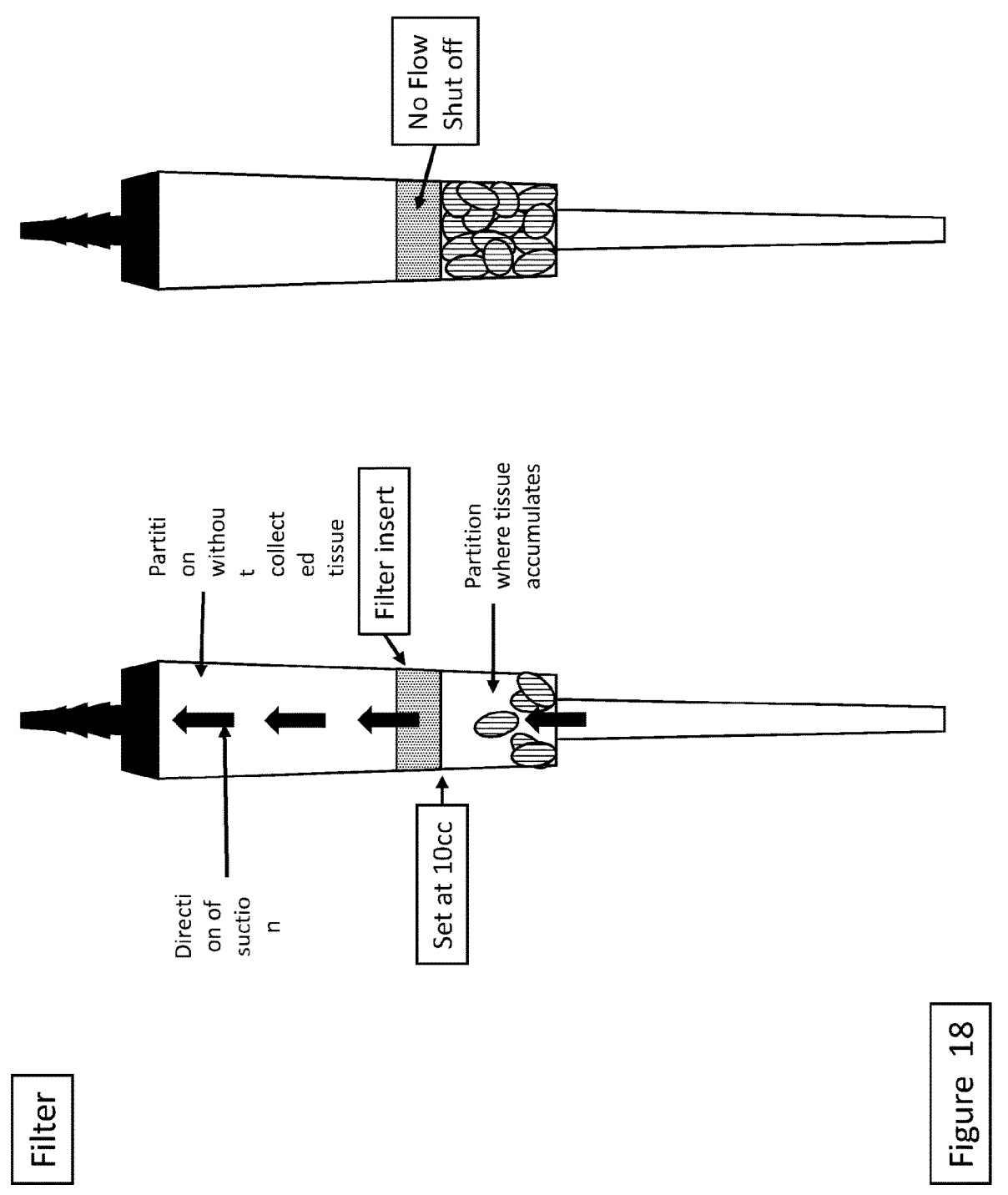

FIG. 18 displays an embodiment that contains a filter that includes fine pores that clog and restrict flow when the receptacle reaches capacity. The pores are calibrated to enable the collection of cancellous bone and bone marrow within a confined space within a larger canister. The canister is partitioned into two regions by the filter. The filter pores can be sized such that once the collection partition reaches capacity, the suction is no longer applied to the inlet where the tissue enters in from. The filter can be an insert that is either modular or set in place. A modular filter insert would allow the user to place the filter at a set volumetric capacity prior to collecting tissue, setting the maximum allowable tissue volume. Once the desired volume is collected, the user can remove the collected graft.

Figure 19:
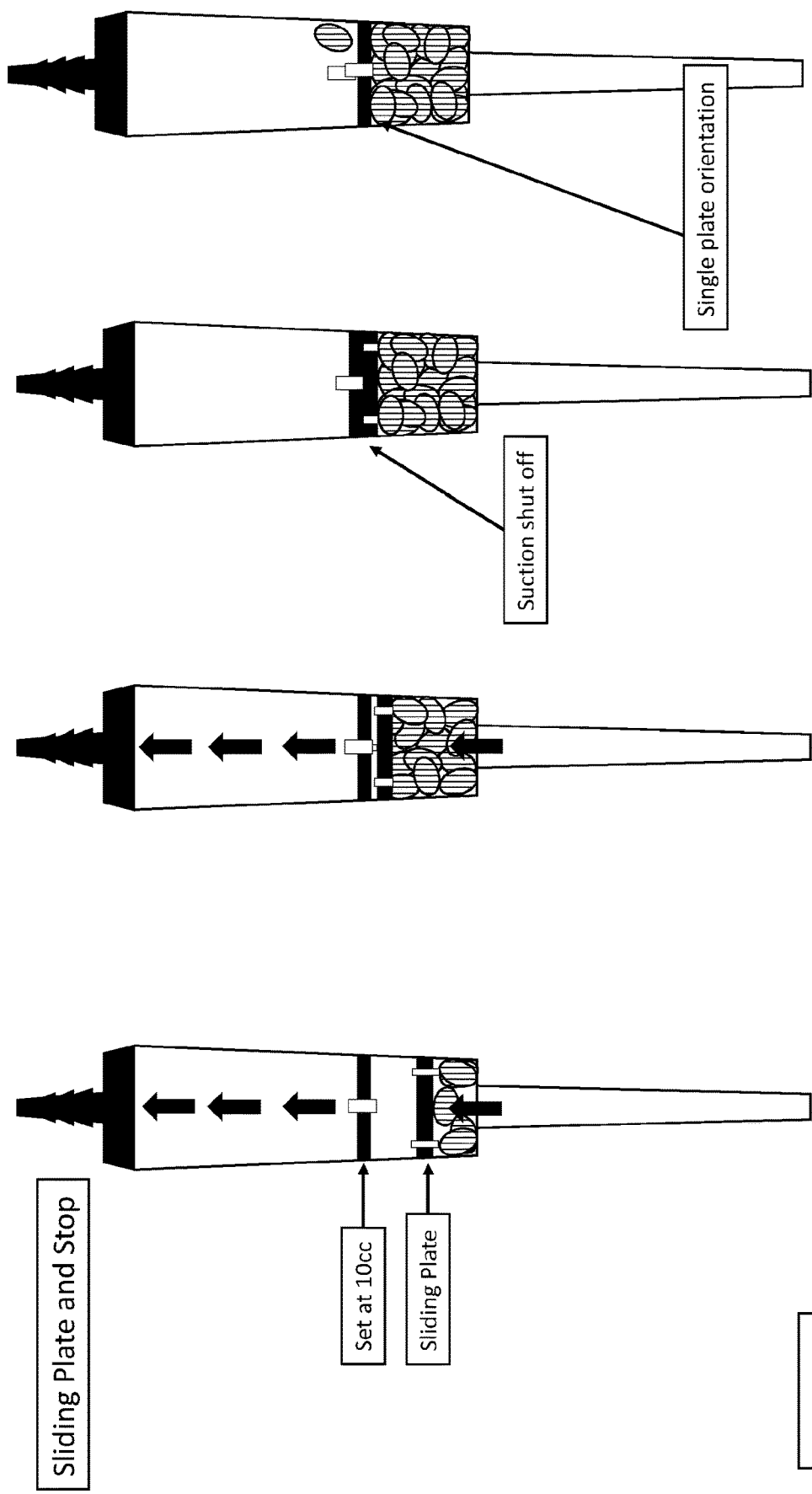
FIG. 19 schematically depicts an exemplary volume control system that utilizes two or more perforated discs according to the present disclosure.

FIG. 19 depicts a volume control method of utilizing two or more perforated discs. One disc is stationary, and the second can linearly translate. The starting position of the second disc is at the inlet location of the canister. The perforations of the discs are such that when they are not together, they each allow suction flow to pass through, but when stacked on top of each other they occlude suction. As tissue flows into the canister through the inlet, the second disc is pushed and linearly translated towards the first (i.e., stationary). Tissue can be collected until the maximum capacity is achieved, which occurs when the second disc contacts the first disc to prevent more tissue from entering the canister.

A second embodiment, containing only one perforated disc, does not block suction when capacity is reached and instead allows for spill-over of collected tissue. This embodiment creates a physical barrier in which tissue is forced to collect mostly beneath the perforated disc.

Figure 20:
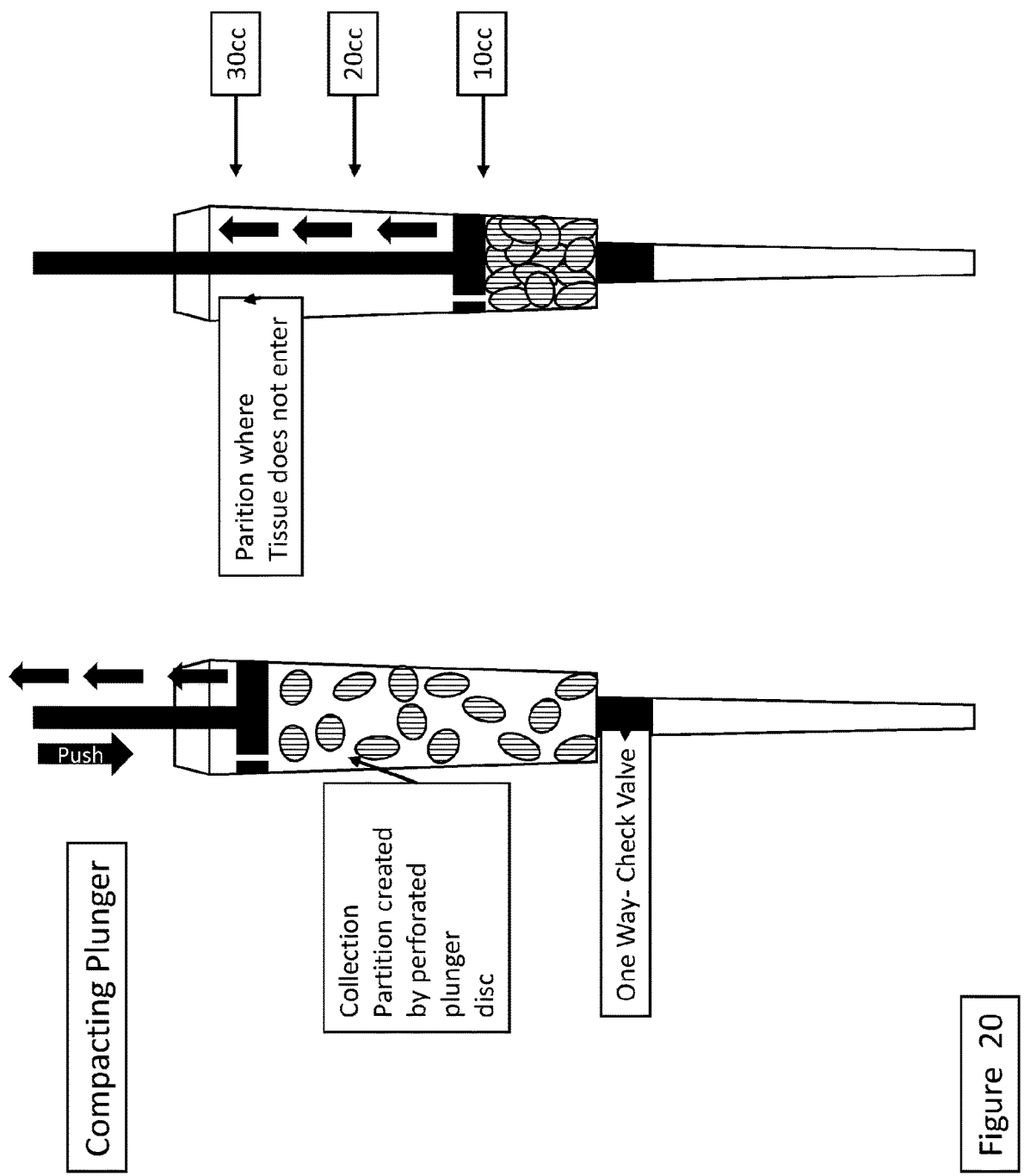
FIG. 20 schematically depicts an alternative exemplary volume control system wherein a plunger is provided according to the present disclosure.

FIG. 20 displays an embodiment in which the user can actuate a plunger in order to intermittently compact tissue within the canister for an accurate volume reading. The plunger has a head that is perforated, which acts as a filter to contain the collected material while enabling suction to the inlet. During use, the user can linearly translate the plunger to compress the collected tissue at the bottom of the canister. This can also be done in the orthogonal direction by compressing the bone to one side of the canister. The edge of the plunger head is flush with the internal surface of the canister to act as a squeegee. A one way check valve is located at the inlet to keep the tissue inside the collection and measurement region of the canister.

FIG. 21 depicts a spring-loaded perforated plunger. The starting position of the plunger head is at the 0 cc mark. As tissue is collected inside the suction canister, the spring allows the plunger head to translate as more volume is collected. The spring constant is selected to create resistance at a set volume or allow continuous compacting of bone throughout the collection process. Selecting a spring constant that creates an overpowering resistance at 10 cc or 20 cc (or other preset volume) may be desirable to capture a specific amount of volume. However, the spring constant can also be selected to allow continuous compression of the collected tissue in order to enable optimal reading of the tissue volume. A one way check valve is located at the inlet to keep the tissue inside the collection and measurement region of the canister.

Figure 22A:
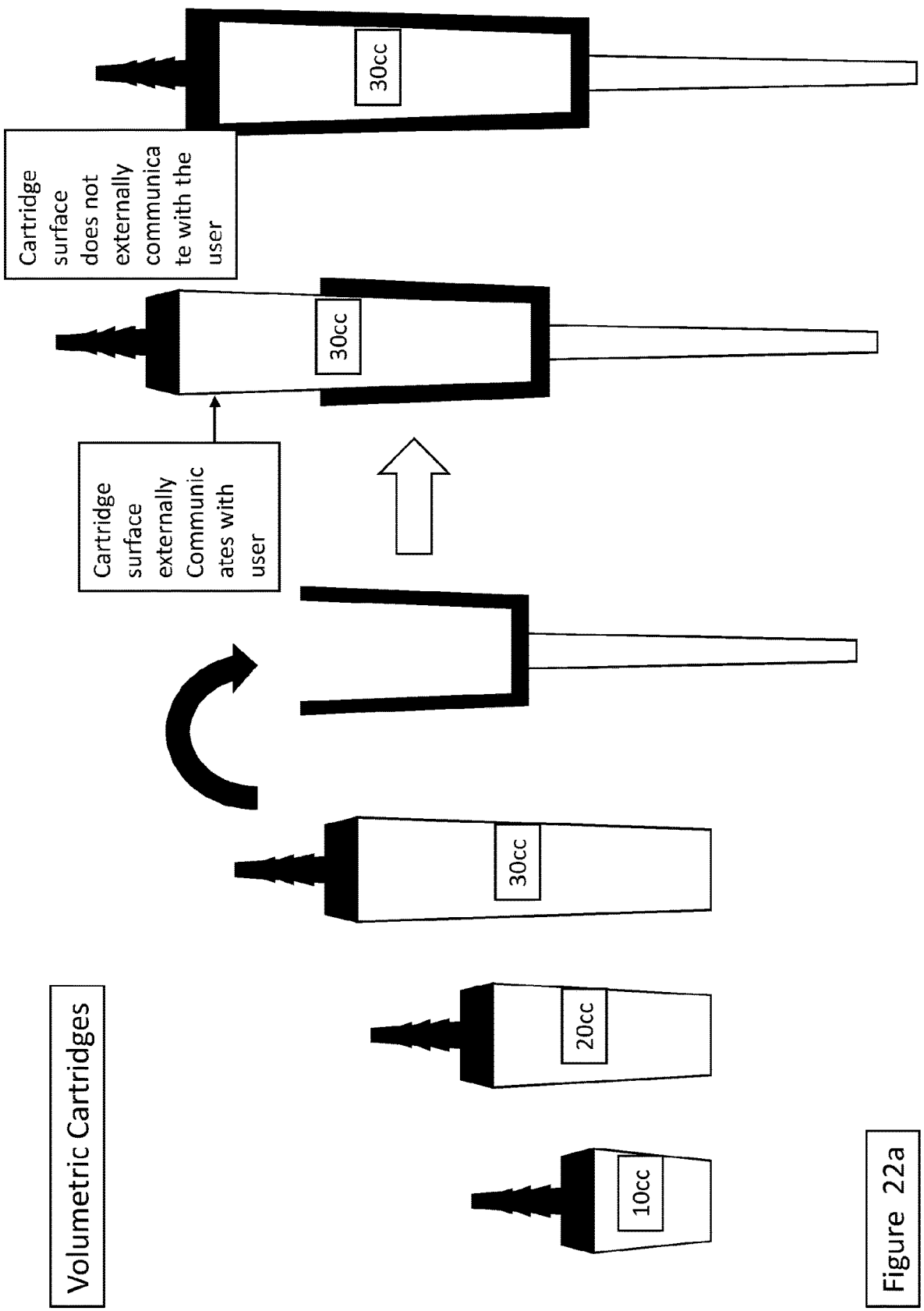
FIG. 22a schematically depicts an exemplary interchangeable cartridge system according to the present disclosure.

FIG. 22a depicts an interchangeable cartridge system which enables the user to utilize cartridges of different volumes. The cartridge could be screwed, clipped, pinned, or snapped into the suction canister, creating an air-tight connection. The cartridge could serve as the external surface of the suction canister, or the cartridge could be inserted into a preset suction canister.

Figure 22B:
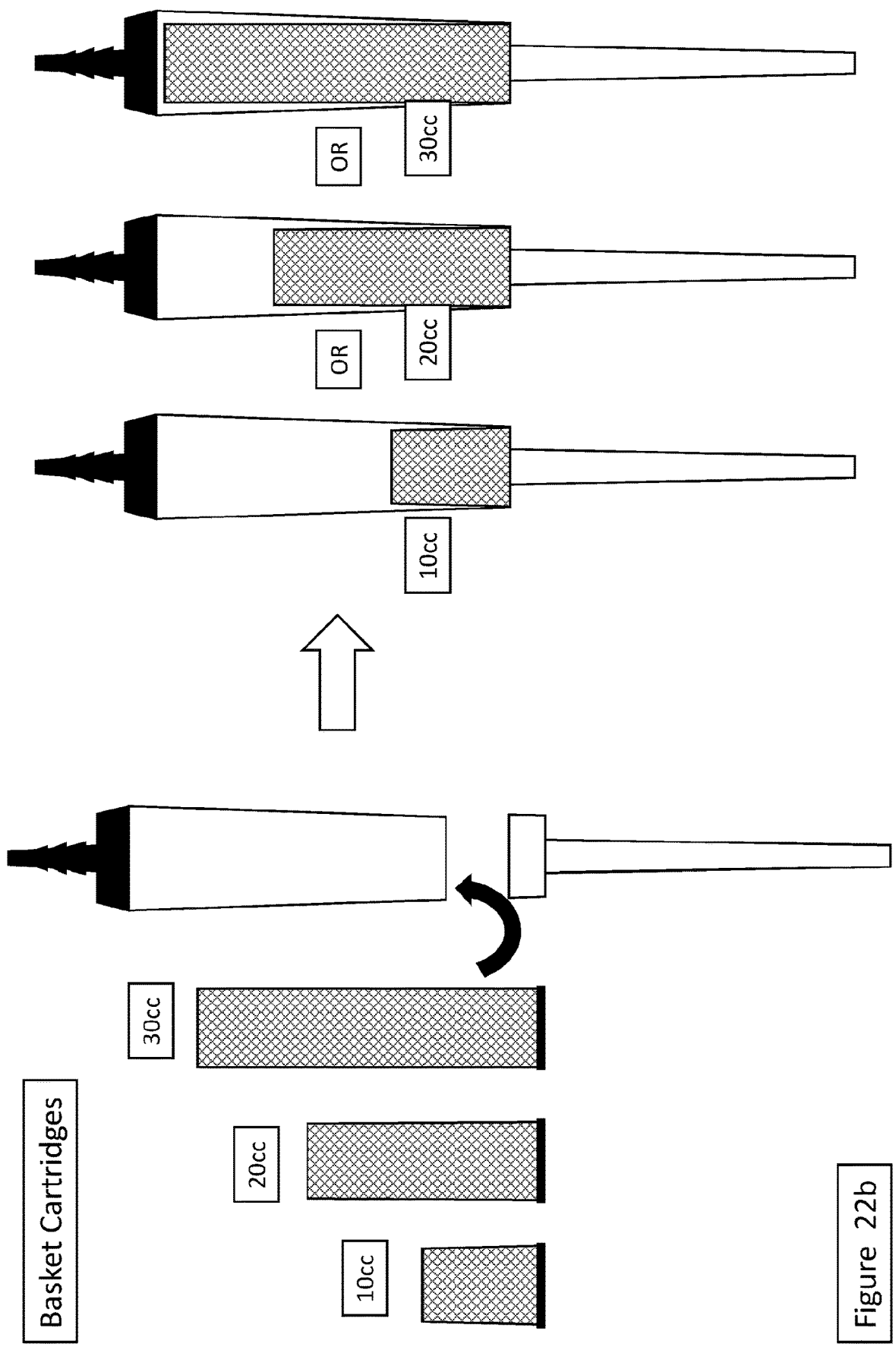
FIG. 22b schematically depicts an exemplary basket cartridge for use with a collection receptacle according to the present disclosure.

FIG. 22b depicts a basket cartridge that can be inserted and connected to a collection receptacle. The rigid basket contains one or more perforations and acts as a catcher's mitt, blocking tissue from advancing beyond its boundary and allowing the flow of suction to continue as material accumulates inside the basket. Once the desired amount of tissue is collected, the basket can be removed, and the tissue can be retrieved.

Figure 22C:
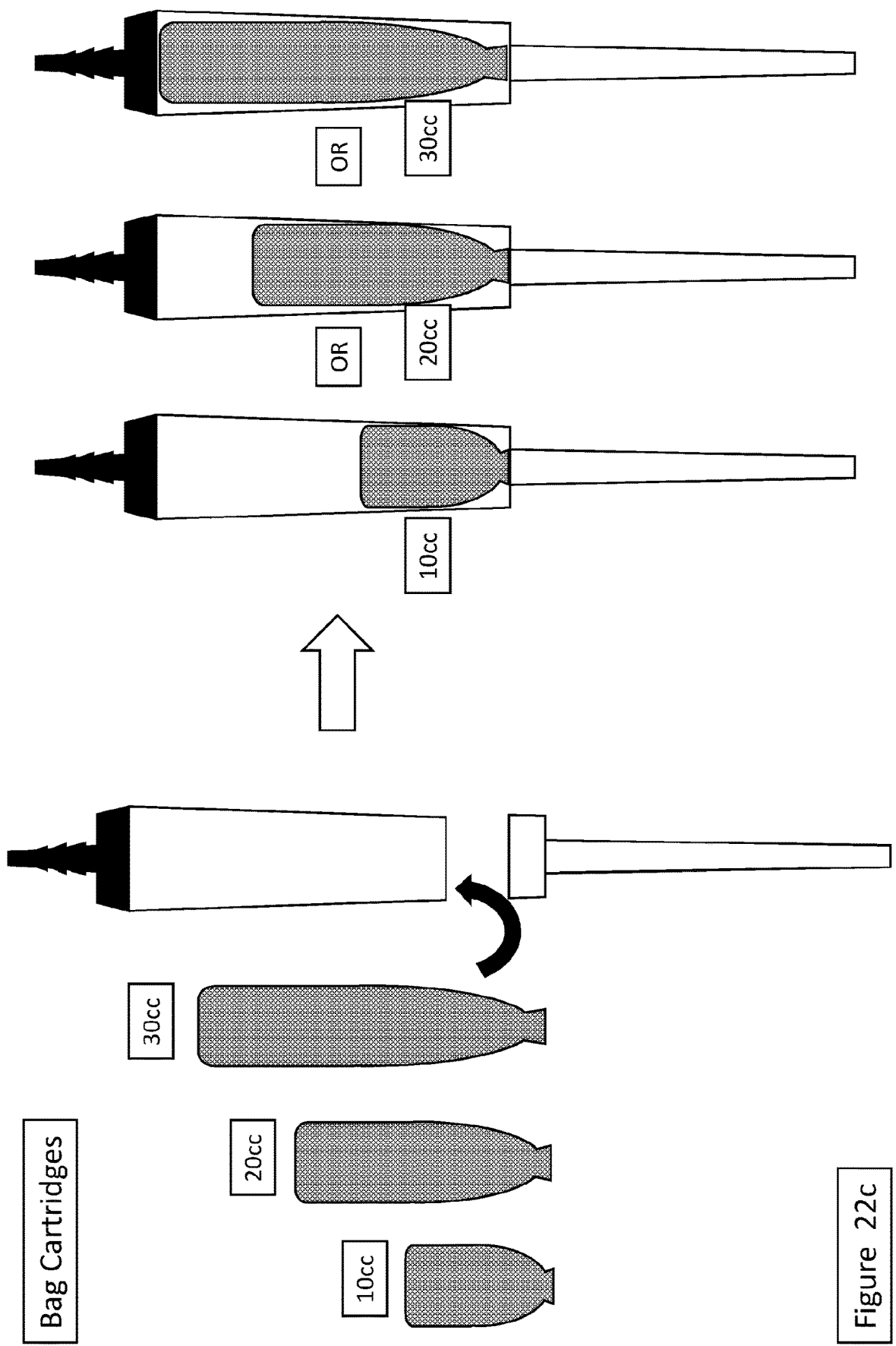
FIG. 22c schematically depicts an exemplary bag cartridge for use with a collection receptacle according to the present disclosure.

FIG. 22c depicts a bag cartridge that can be inserted and connected to a collection receptacle. The non-rigid basket contains one or more perforations, blocks tissue from advancing beyond its boundary and allows the flow of suction to continue as material accumulates inside the bag. Once the desired amount of tissue is collected, the bag can be removed, and the tissue can be retrieved.

Figure 22D:
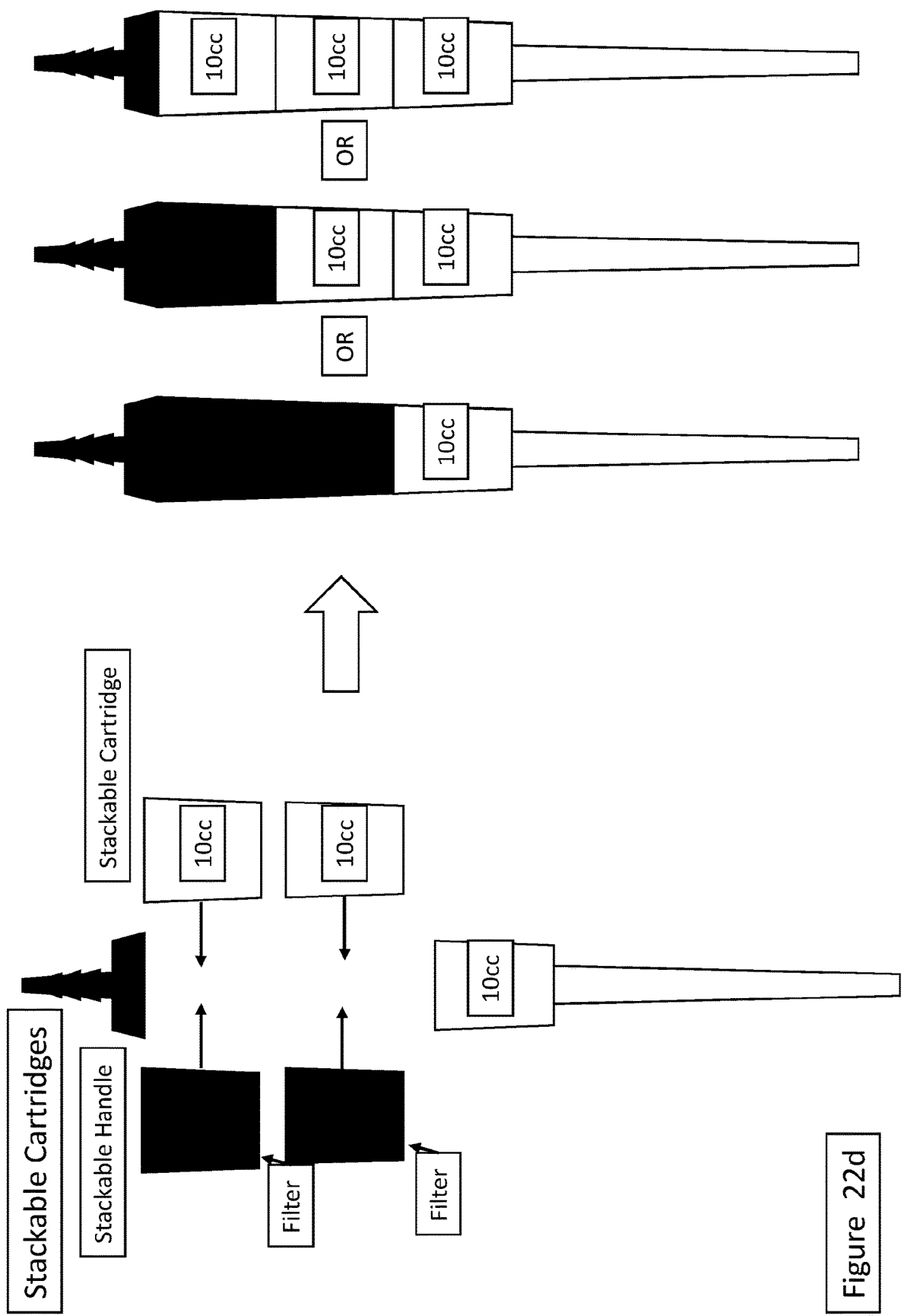
FIG. 22d schematically depicts an exemplary collection receptacle with modularly stackable cartridges and filters according to the present disclosure.

FIG. 22d is an embodiment in which the volume of the collection receptacle is modular through the implementation of stackable cartridges and filters. These are self-sealing casings that stack on each other to alter the volumetric capacity of the collection receptacle. These can be incremental volumes (e.g., 10 cc increments) that are compatible with the particular tissue collection needs.

FIG. 23a presents an embodiment where a removable tissue containment insert 102 can be placed into the tissue collection container 100 to act as a catcher's mitt. This design features fingers 104, 106 that extend proximally to allow for the securement of the filter and to grab onto in order to remove the tissue containment insert 102 from the collection container 100. Tissue containment insert 102 includes a discontinuous wall 110 that partially encloses a tissue containment region 112 and from which the extension fingers 104, 106 extend. Gap or opening 120 is defined by the discontinuous wall 110 that opens to the tissue containment region 112.

Figure 23C:
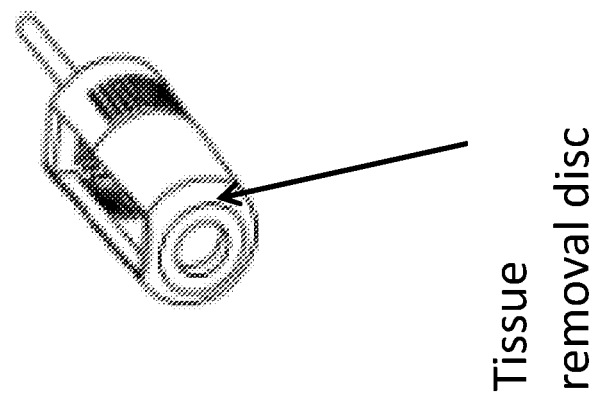
FIG. 23c schematically depicts a further exemplary embodiment that includes removable tissue containment insert(s) according to the present disclosure.
Figure 23D:
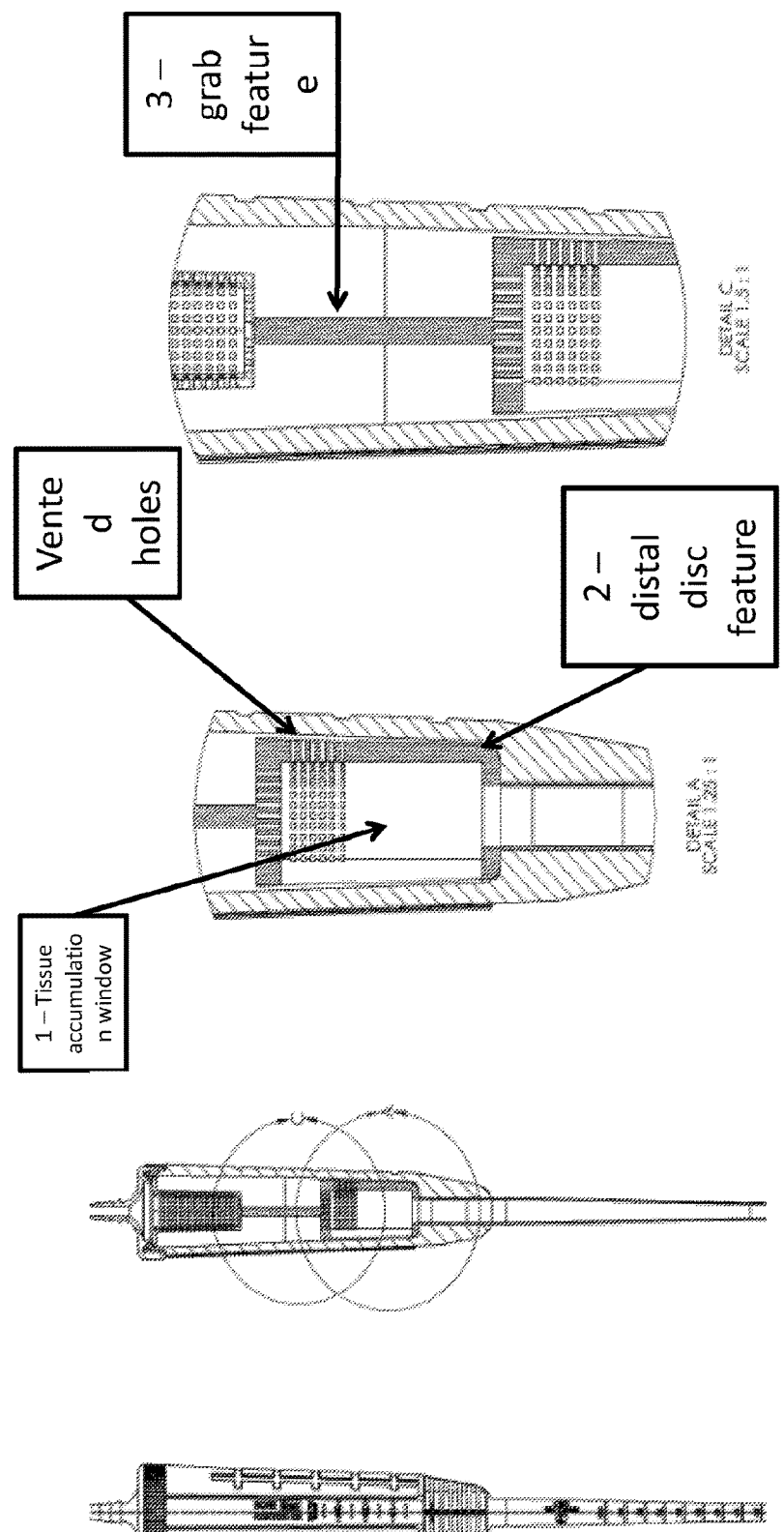
FIG. 23d schematically depicts the removable tissue containment insert of FIG. 23c inside a tissue collection container according to the present disclosure.
Figure 24:
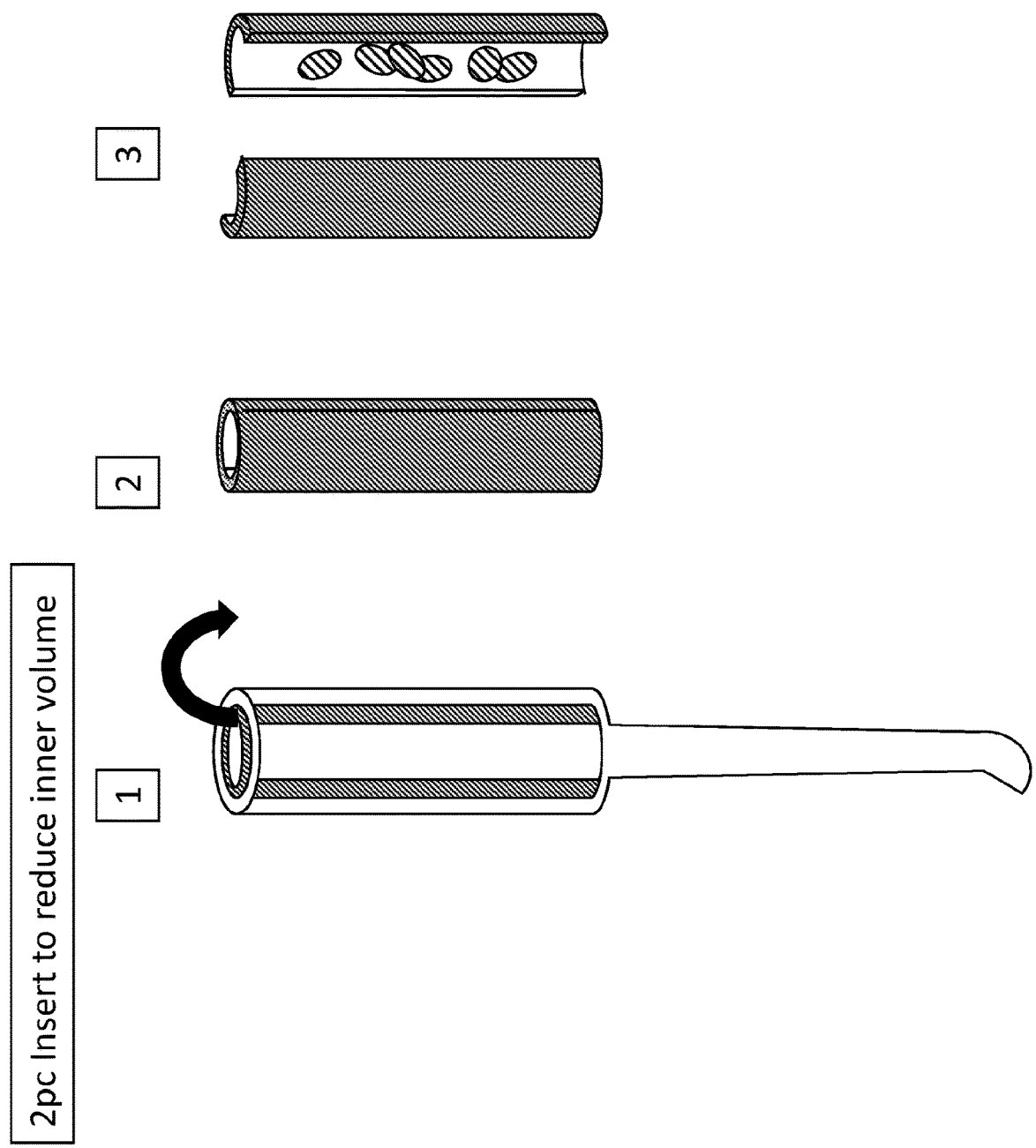
FIG. 24 schematically depicts an exemplary embodiment that includes two piece insert according to the present disclosure.

FIG. 23b further details a tissue window to allow for estimation of volume collected by the user. This window may also be replaced with optically clear material that allows visibility of the tissue. The tissue containment insert further has vent holes to enable vacuum to flow through the insert. These vent holes may be located on any one or more faces of the tissue containment insert. The tissue containment insert can be held in place by the lid or cap to the tissue container, preventing the tissue containment insert from having play within the tissue container. An alternative embodiment of this tissue containment insert can be seen in FIG. 23c. This embodiment features a distal disc that enables for easy removal of the collected tissue. FIG. 23d displays this alternate embodiment inside a tissue collection container. This cross sectional view shows the distal disc, the tissue window where tissue accumulates and the vented features that enable the passing of fluids. Lastly, there is a grab feature that allows a user to open the cap or lid to the tissue container and grab onto the tissue containment insert. The vented holes can be placed on any face of the tissue containment insert FIG. 24 features a two (2) piece insert that can reduce the internal capacity of the collection container.

Figure 25:
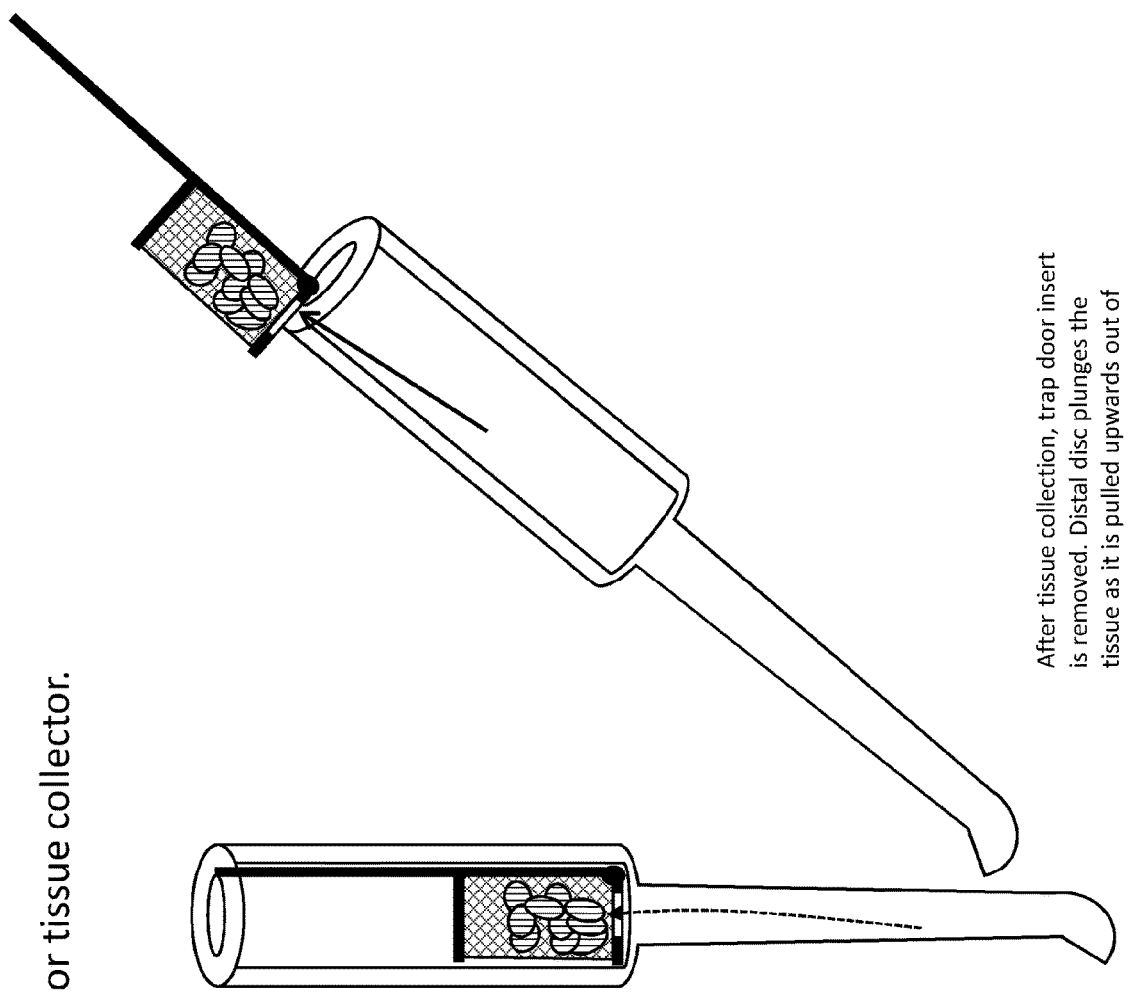
FIG. 25 schematically depicts a further exemplary tissue collection insert according to the present disclosure.

FIG. 25 displays an embodiment for a tissue collection insert that reduces the collection volume for the tissue, while providing airways for the vacuum to draw tissue into the collection window. The trap door insert features a distal disc with an entry hole for material to transport through. After tissue collection is completed, the trap door filter insert can be pulled out of the internal lumen of the suction canister. The distal disc pulls the collected tissue securing it inside the cartridge-like reservoir. Once removed, pressure is applied to the distal disc trap door to either unhinge or secure the trap door into the open position to gain access to the collected tissue. The mesh walls could either be rigid or flexible or enable the collection of solid tissue material and some passing of fluid and air. Vents can be on the top or lateral faces of the geometry or a combination of both.

Figure 26:
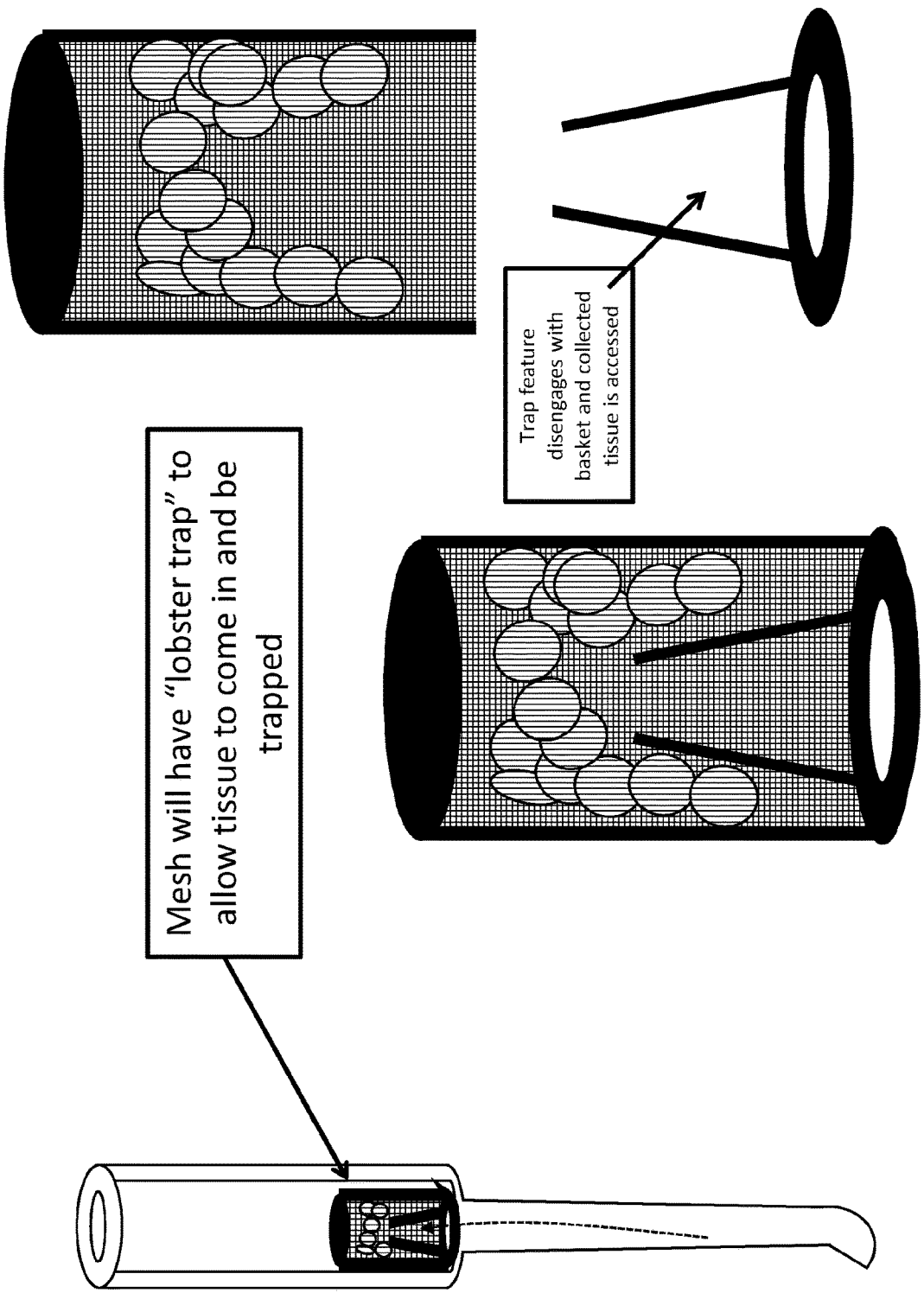
FIG. 26 schematically depicts an exemplary tissue manipulation embodiment according to the present disclosure.

FIG. 26 displays a tissue manipulation embodiment that features a basket with an entry and a lobster trap feature that directs tissue to the side walls. These lobster trap inner walls further prevent backflow of tissue material into the cannulation where material is being transported from. Once tissue collection is completed, the embodiment can be removed from the suction canister lumen and the trap feature can disengage allowing the user to access the collected tissue.

Figure 27:
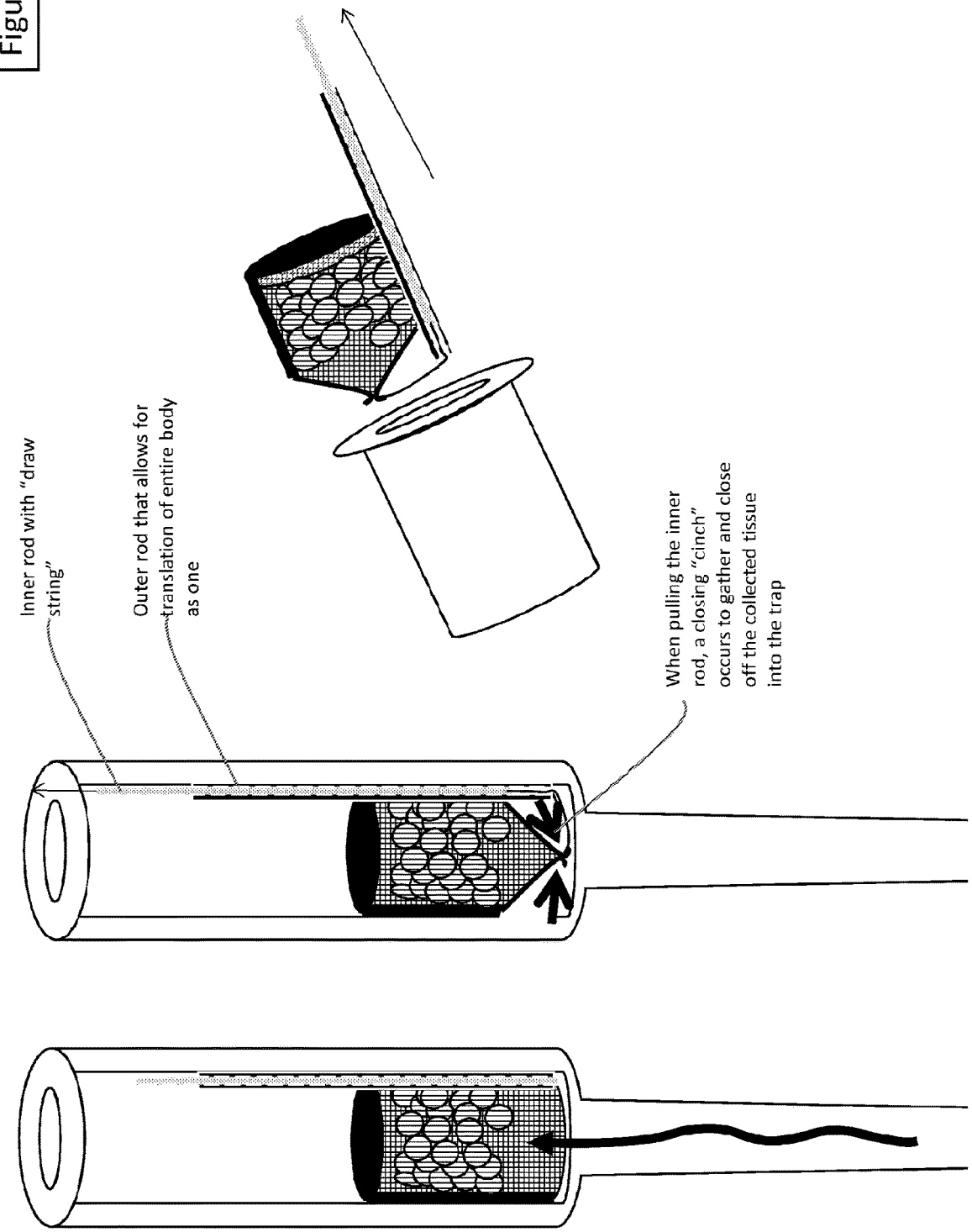
FIG. 27 schematically depicts an exemplary drawstring filter trap insert embodiment according to the present disclosure.

FIG. 27 displays a drawstring filter trap insert. This embodiment features a trap assembly with a meshed chamber for tissue to collect. The meshed chamber is attached to an outer rod. An inner rod freely slides inside the outer rod. The inner rod is connected to the distal end feature of the meshed chamber such that when the inner rod is retracted or pulled proximally out of the outer rod, the distal end of the meshed chamber is cinched or closed off. In the closed position, the collected tissue is forced inwards and up into the chamber. While maintaining this upwards pressure to keep the chamber in the closed state, the assembly is removed from the suction canister by proximally pulling the outer rod out of the lumen of the suction canister. The inner rod can then be translated to reopen the mesh chamber to access the collected tissue.

Figure 28:
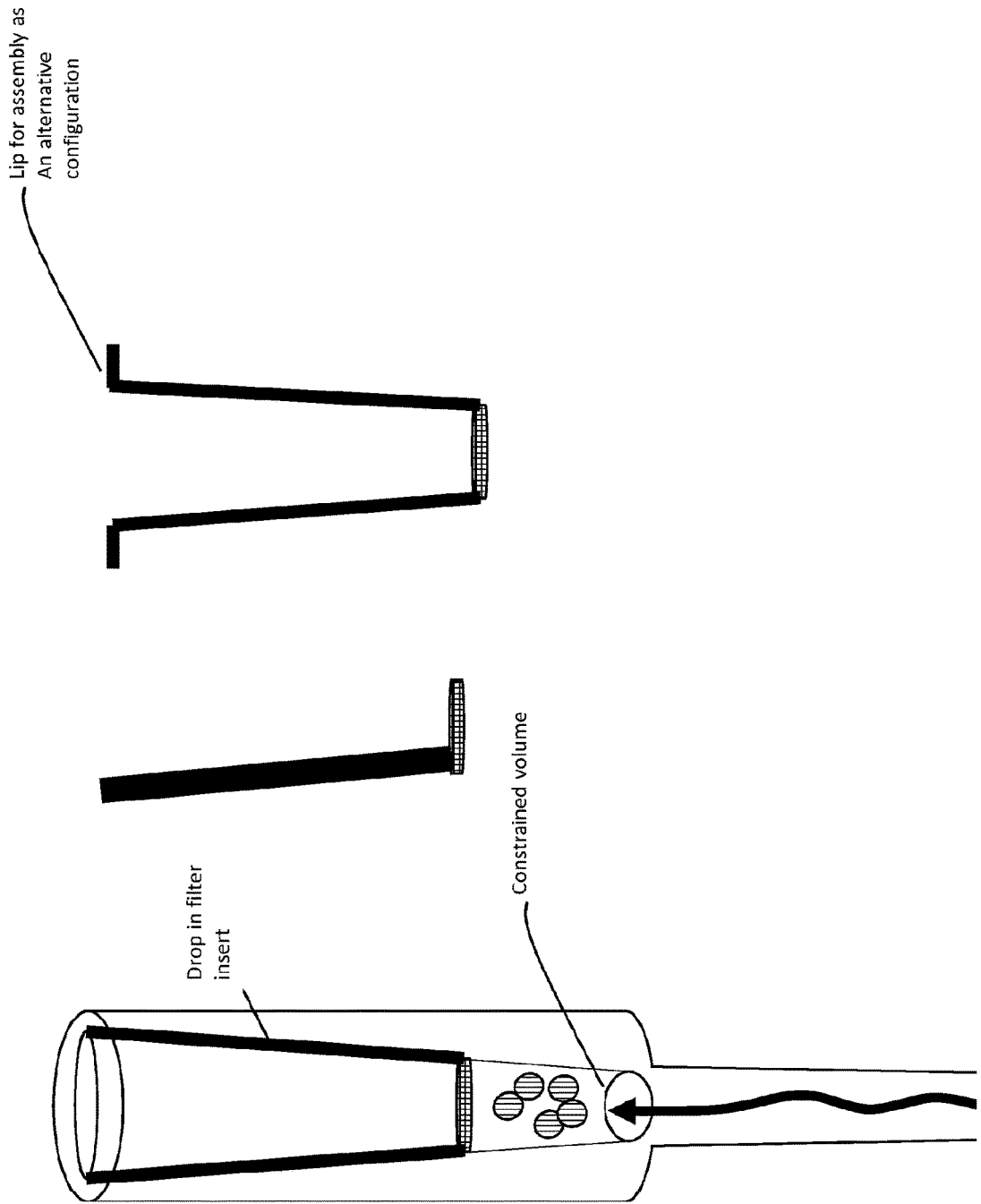
FIG. 28 schematically depicts an exemplary tissue manipulation insert according to the present disclosure.

FIG. 28 is a tissue manipulation insert that features vents on one or more faces of the construction. The insert may have a fully conical wall (left) or a partial wall (middle) wall or conical base that at least partially revolves around the circumference of the distal filter. The insert falls into place via interference fit of the distal filter with a tapered suction canister lumen. Alternatively, a lip can be implemented to have the insert rest on top of the lip of the suction canister lumen (right).

Figure 29:
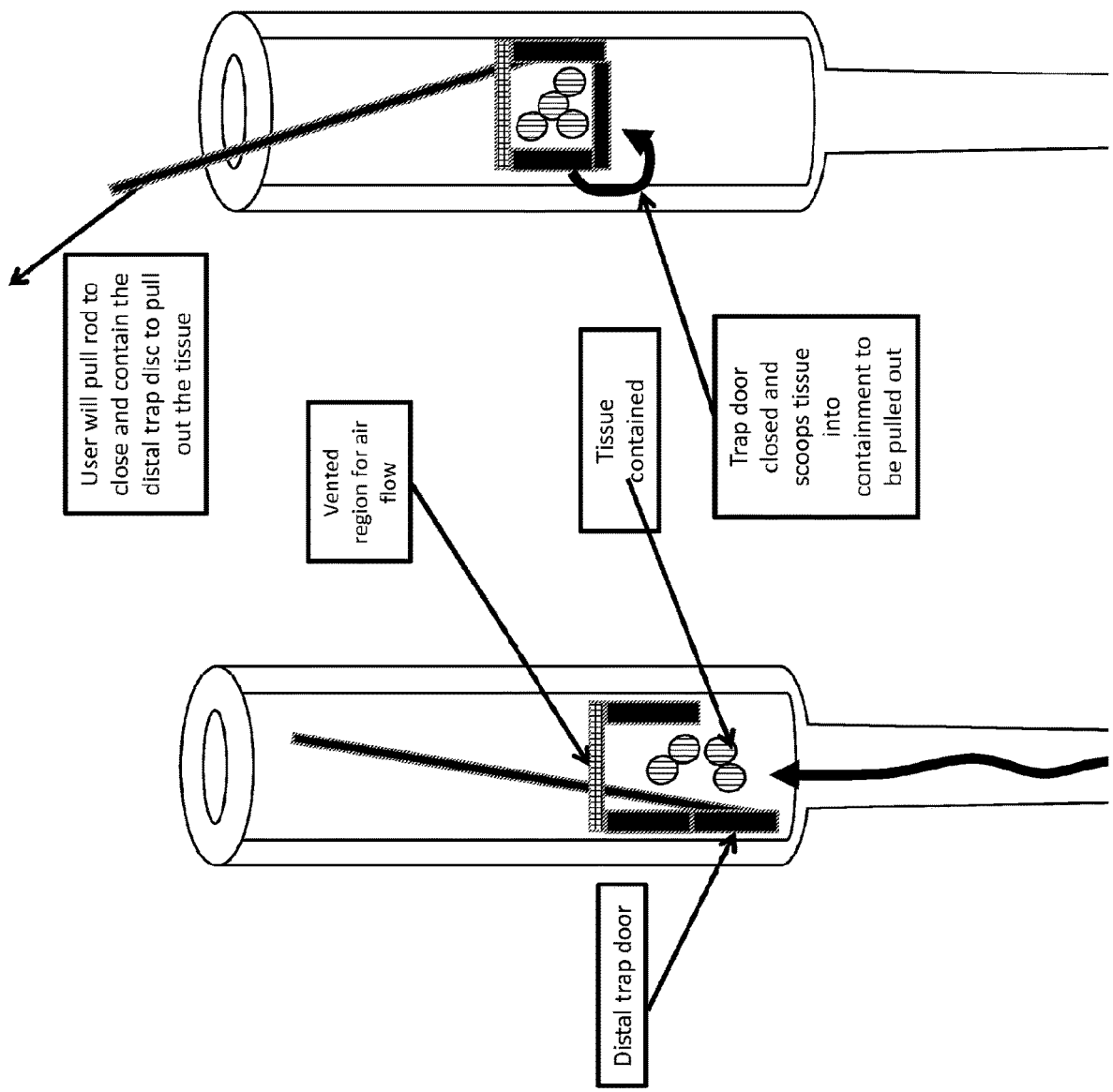
FIG. 29 schematically depicts an exemplary tissue containment mesh chamber embodiment according to the present disclosure.

FIG. 29 is an embodiment which includes a tissue containment mesh chamber that can open and close. A rod is attached to a distal trap door of the mesh chamber. Any face may contain vents to allow the passing of fluids and air. In the open state, tissue is able to enter into the chamber. Once tissue collection is complete, the rod is pulled to close the trap door and scoop the tissue into the chamber. This rod can be externally communicating such that the closing of the trap door is performed under suction. If the rod is contained within the suction canister, then the closing process can be performed with the canister upside down to use gravity to keep the tissue contained within the chamber. Once the closed mesh chamber is removed from the suction canister, the rod is actuated again to enable the open state to obtain access to the collected tissue.

Figure 30:
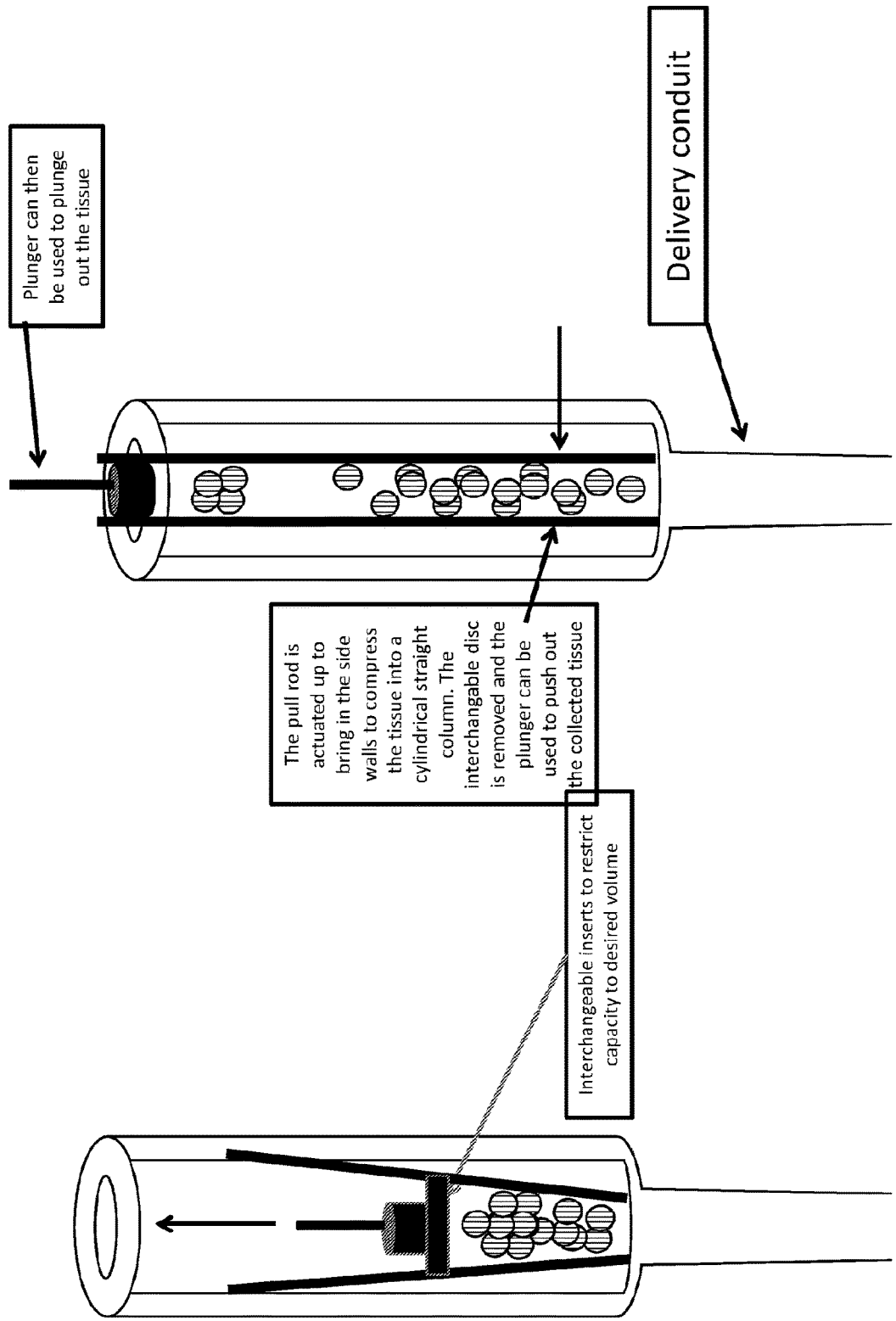
FIG. 30 schematically depicts an exemplary embodiment that includes a conical insert having an adjustable shape according to the present disclosure.

FIG. 30 is an embodiment which includes a conical insert that has adjustable shape. The collection state configures the side walls into a conical shape. A disc is used to constrain the volume of tissue. Once tissue is collected, the suction canister is opened and the central disc feature is pulled upwards to bring the tapered walls into a straight cylinder. In doing so, the collected tissue compresses into a central column of tissue. The restriction disc is disengaged and a plunger can be used to plunge out the collected tissue into a delivery conduit.

FIG. 31a is an embodiment for a tissue containment feature for a suction tissue collection receptacle that has an open and closed position. In the open state, no volume restriction occurs. In the close state the filter disc is placed into position to contain graft. The receptacle can contain one or more of these filters to enable switching on different levels of volumetric containment. This feature can have an externally communicating feature such as a lever or knob that toggles the filter between the open and closed state. Alternatively, the filter has a pull tab or feature that enables a user to snap the filter into place. This can be a pull tab that gets pulled with graspers or forceps. Once in place, the tissue is collected in the chamber formed distally from the filter. Once collection is complete, the filter can be opened to enable access to the collected tissue.

Figure 31B:
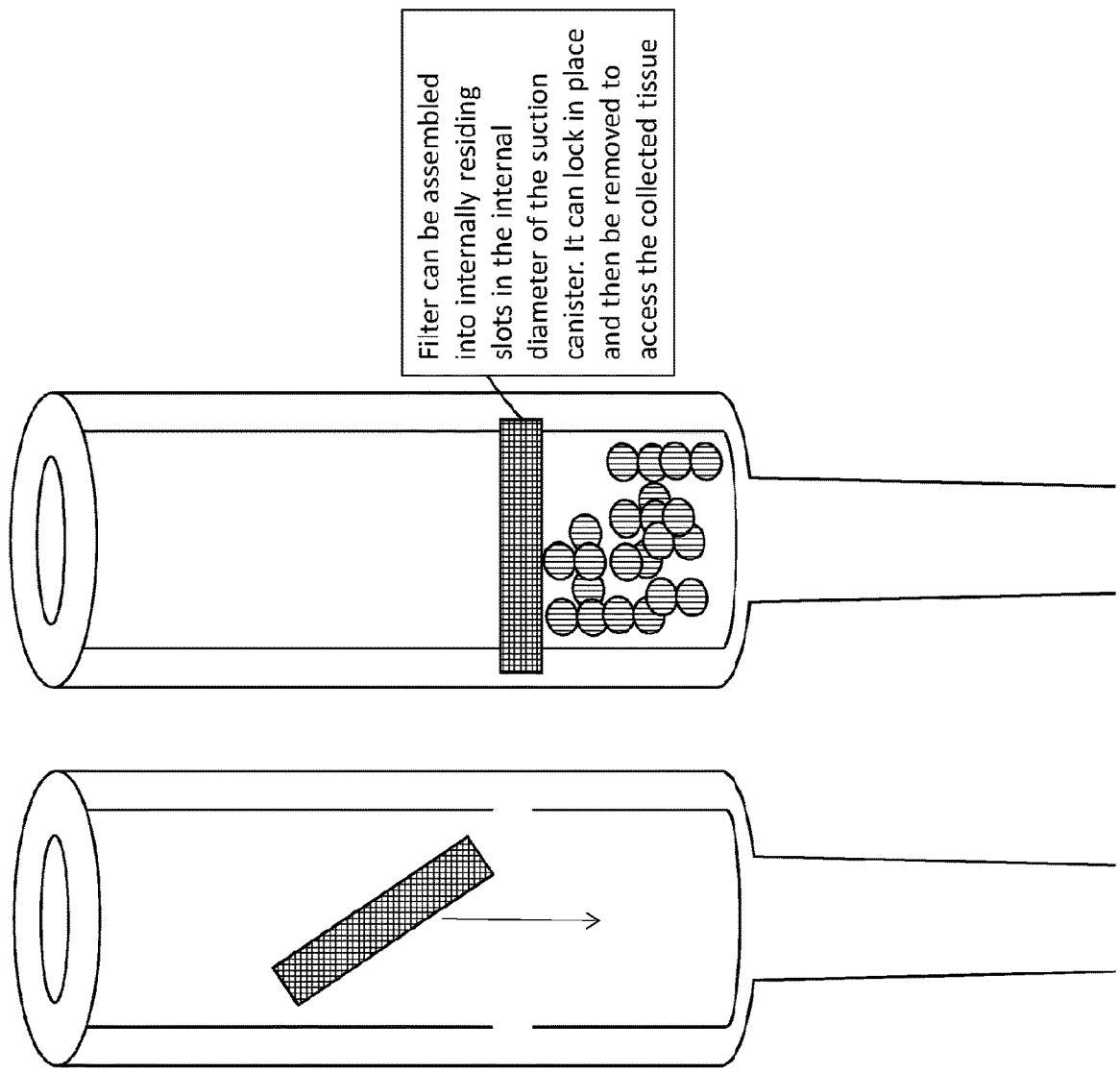
FIG. 31b schematically depicts an exemplary configuration where the internal diameter includes mating features according to the present disclosure.

FIG. 31b is a configuration of this design where the internal diameter has indents for mating features for the filter disc. There can be one or more locations of these indents to snap the filter in place at different volume levels. The filter can snap into place prior to tissue collection and then removed once the collection process is completed.

FIG. 31c is a configuration where there is a central axis about which the filter rotates with an externally communicating actuation feature. The feature can open or close the filter gate. There can be one or more filter gates along the length of the suction receptacle to turn on and off different collection volumes.

Figure 32:
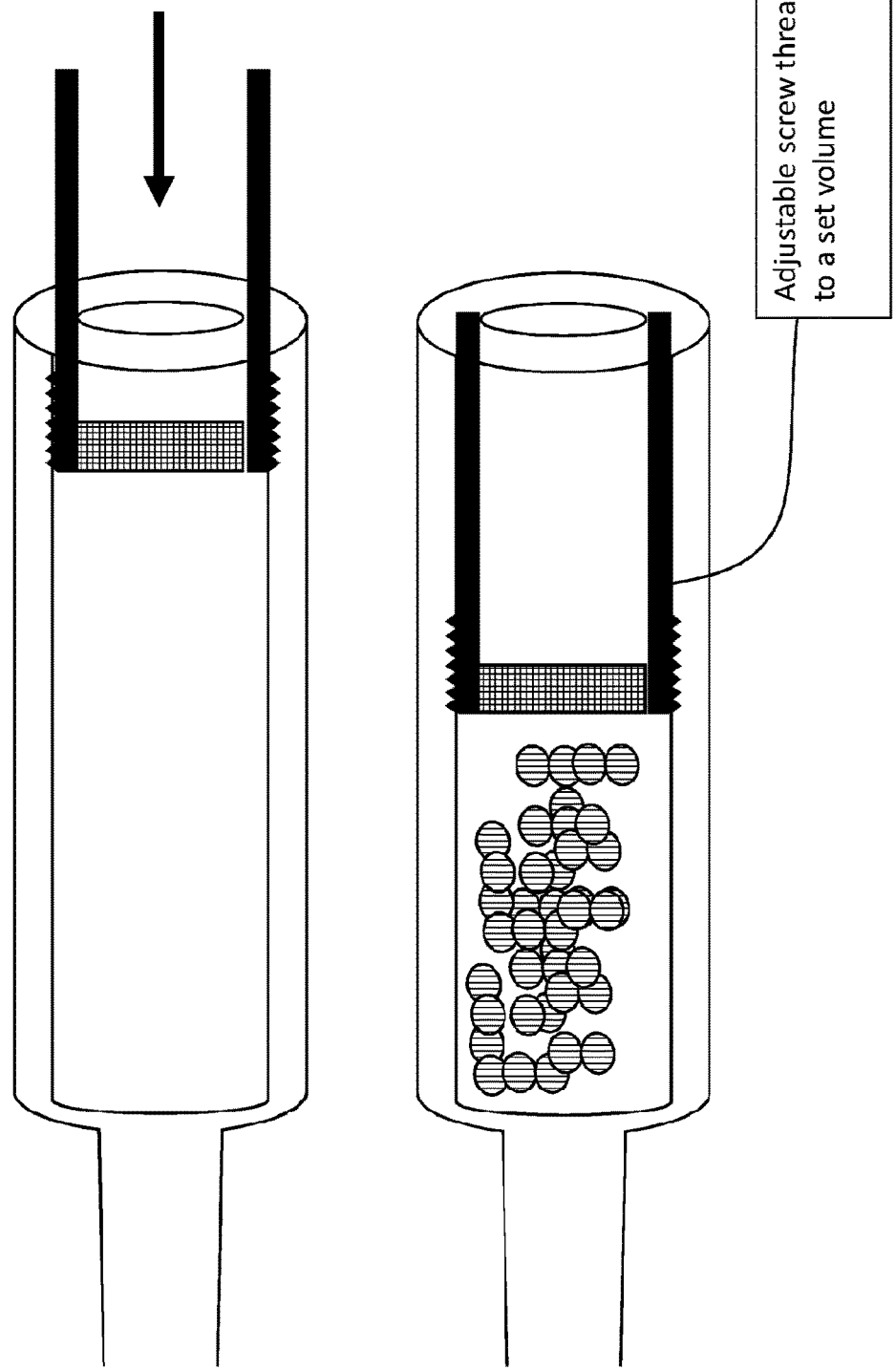
FIG. 32 schematically depicts an exemplary adjustable insert with a filter disc according to the present disclosure.

FIG. 32 features an adjustable insert with a filter disc with side walls or surfaces that interface with threads or ribbed mating surfaces along the internal surface of a suction canister. This enables flexibility of the filter to trap any iteration of volume. It would be threaded or snapped into place prior to tissue collection and then removed once tissue collection is completed.

FIG. 33a features an insert that is a geometry containing a lumen with a filter located proximal to the opening where tissue enters the embodiment. A plunger is pre-assembled such that the plunge is proximally at rest while tissue enters through the distal opening of the tissue containment insert. The plunger is disc-like and has an externally communicating feature to the tissue containment insert that enables linear translation of the plunger disc. Once tissue harvesting is completed, the insert is removed from the suction canister and the plunger is linearly translated to plunge out the collected tissue.

Figure 33B:
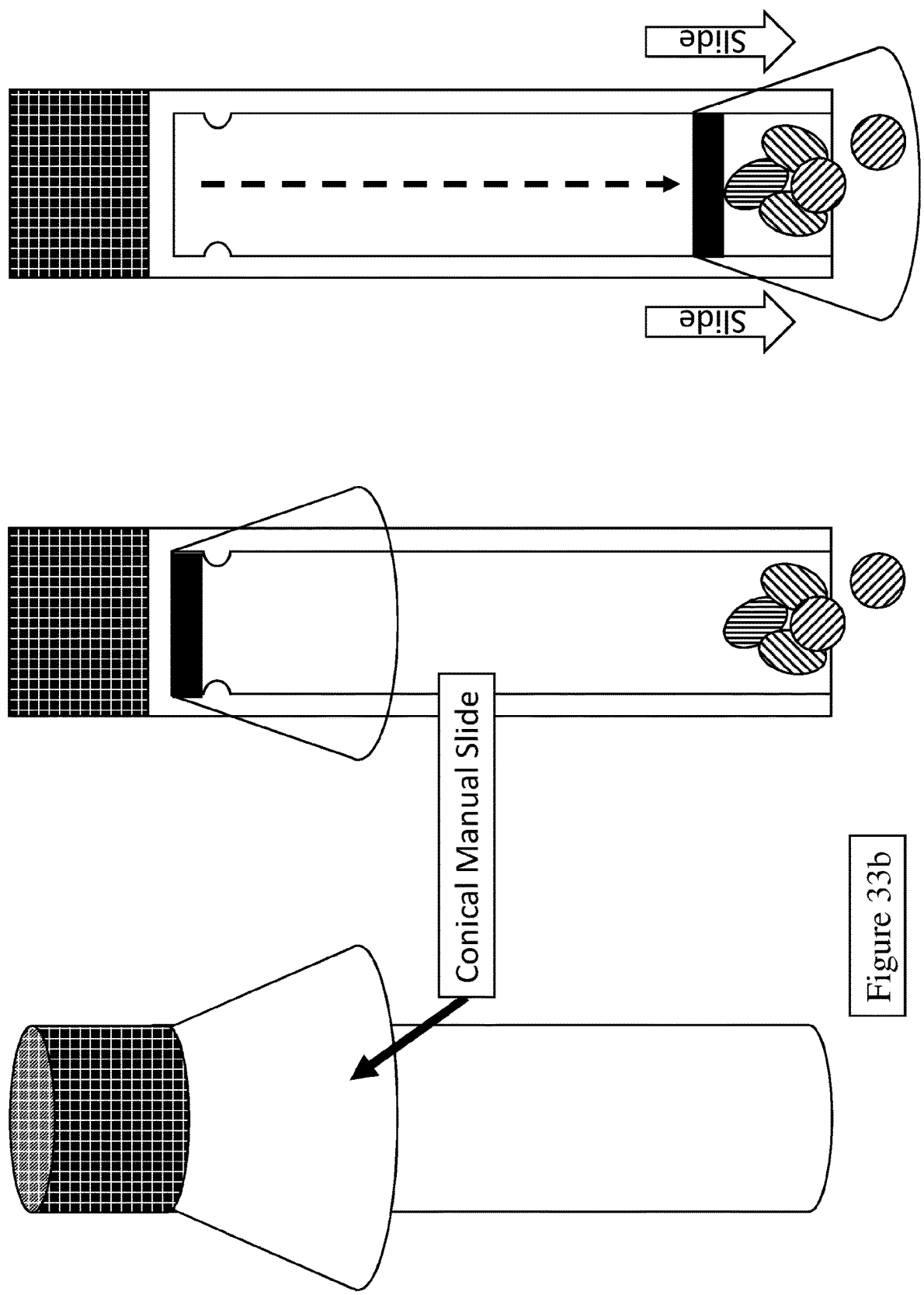
FIG. 33b schematically depicts an exemplary configuration with an alternative externally communicating feature according to the present disclosure.

FIG. 33b presents a different externally communicating feature, such as a conical disc or a partially revolved feature, to increase surface area for finger grip in order to slide the disc to plunge out the tissue.

In further advantageous devices, systems and methods of the present disclosure, tissue harvesting collection devices with clinically beneficial cutting tips are provided.

Figure 34A:
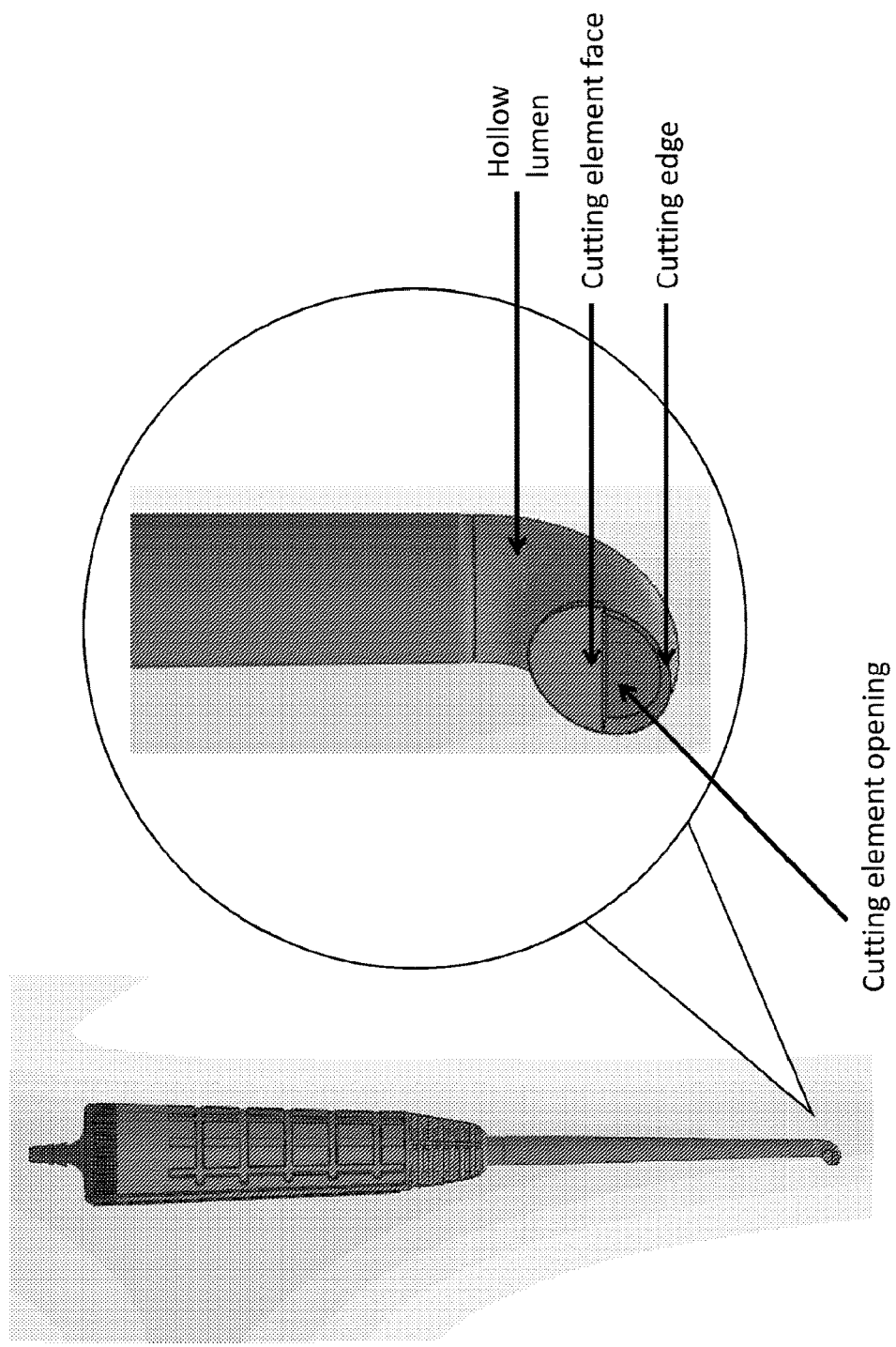
FIG. 34a schematically depicts an exemplary tissue harvesting collection device according to the present disclosure.

FIG. 34a displays a tissue harvesting collection device that cuts and collects tissue. There are various advantages and uses with different cutting tip elements. Modifications to the cutting tip element shown can have several potential advantageous. Some of these benefits are as follows:
  Enable harvesting of different types of tissue
  Enable different cutting strokes to reduce user effort Improve the speed of cutting and ease of use of the instrument
Minimize or prevent clogging of the instrument
Control the consistency of the cut tissue material
Offer flexibility to the user in cutting mechanisms The following are various embodiments of the cutting element that manipulate the cutting edge, opening channel for tissue material entry, and overall geometry.

Figure 34B:
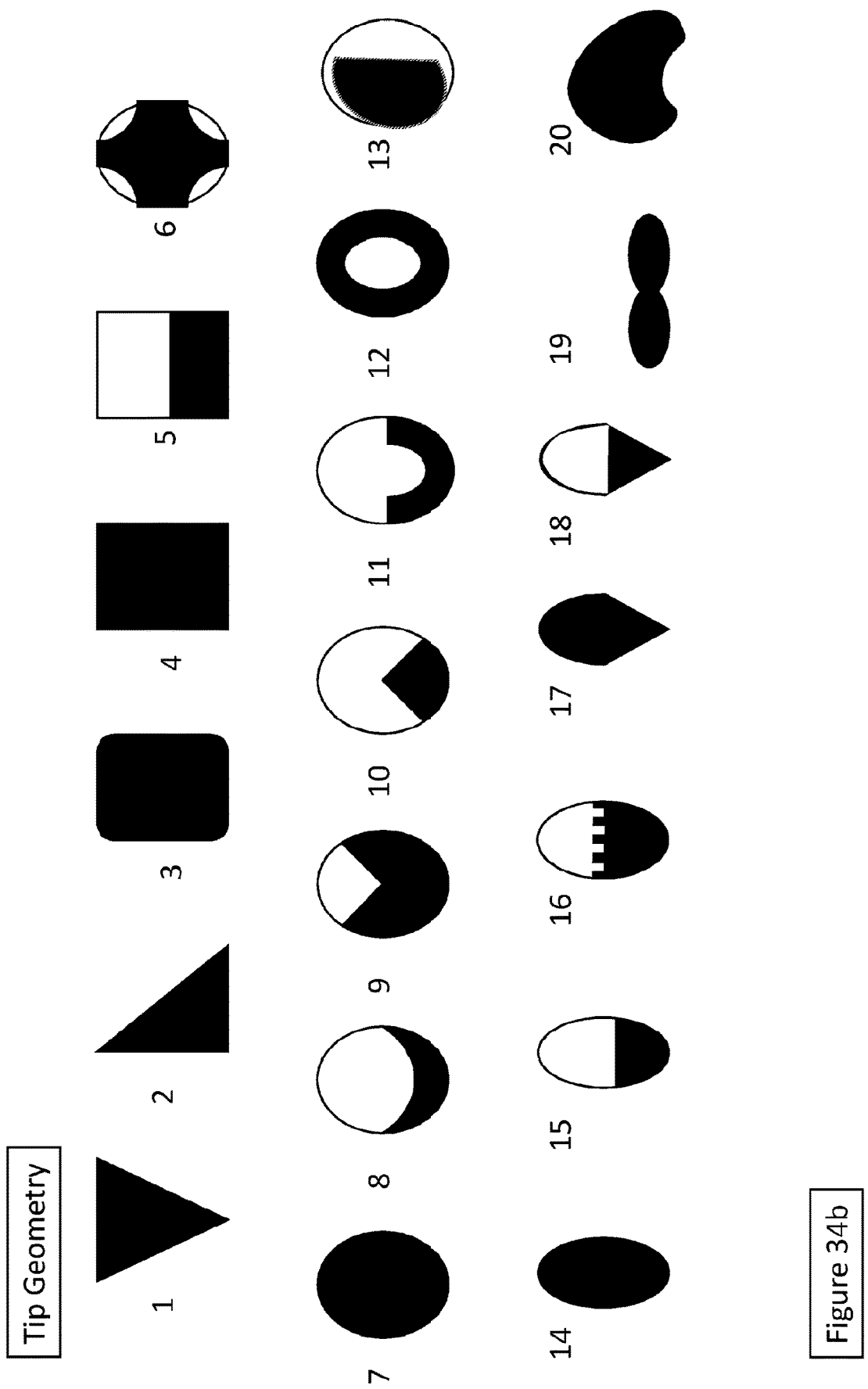
FIG. 34b schematically depicts an exemplary and advantageous array of cutting head geometries according to the present disclosure.

FIG. 34b displays an array of cutting head geometries. In the various schematic illustrations provided herein, the darkened area represents the opening to the internal lumen of the shaft shown in FIG. 34a. All of these embodiments feature an opening that is smaller in cross sectional area than the lumen.

Configurations 1 and 2 feature a triangular tip to offer a sharp aggressive cutting point to advance the tool with less force. Configuration 2 has more aggressive side cutting as opposed to the central cutting of Configuration 1. Configuration 3, 4 and 5 are square cutting tips that allow the user to cut flat surface profiles. Configuration 6 has a plus sign variation of the cutting edges, reducing the active cutting surface to enable small chunks of tissue. The beveling shown creates a blockade to force the size of the cut tissue to be smaller than the opening of cutting element.

Configurations 7-13 display circular cutting faces with manipulations of the active cutting surface vs. the occluding surface. Configurations 14, 15 and 16 offer a balance between the triangular cutting tip and circular cutting with an oval cutting face. The narrow cutting tip is more aggressive than the circular configurations and offers a narrower cutting element. Configurations 17 and 18 are combinations of a triangular surface and a circular one. 18 is an occluded version of 17. Configuration 19 depicts a crimped cutting face which may improve clogging characteristics and ease of manufacturability. Configuration 20 is an oblong cutting surface with dominant side cutting faces to control the feed of the cut.

Figure 34C:
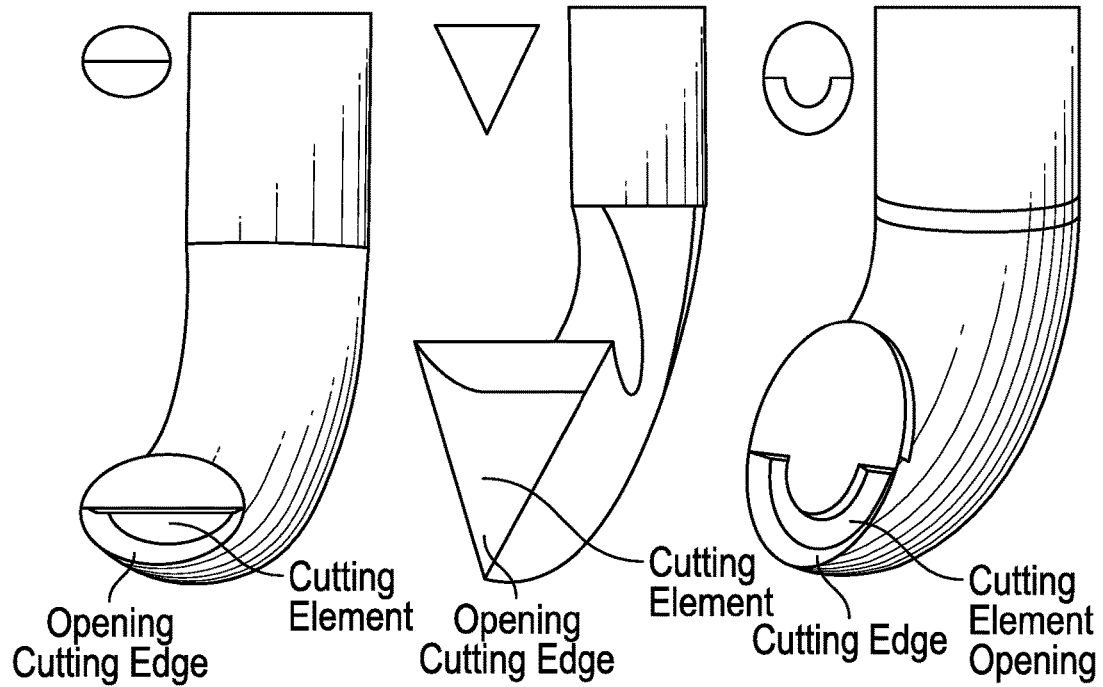
FIG. 34c schematically depicts three dimensional representations of three (3) of the cutting head geometries of FIG. 34b according to the present disclosure.
Figure 34D:
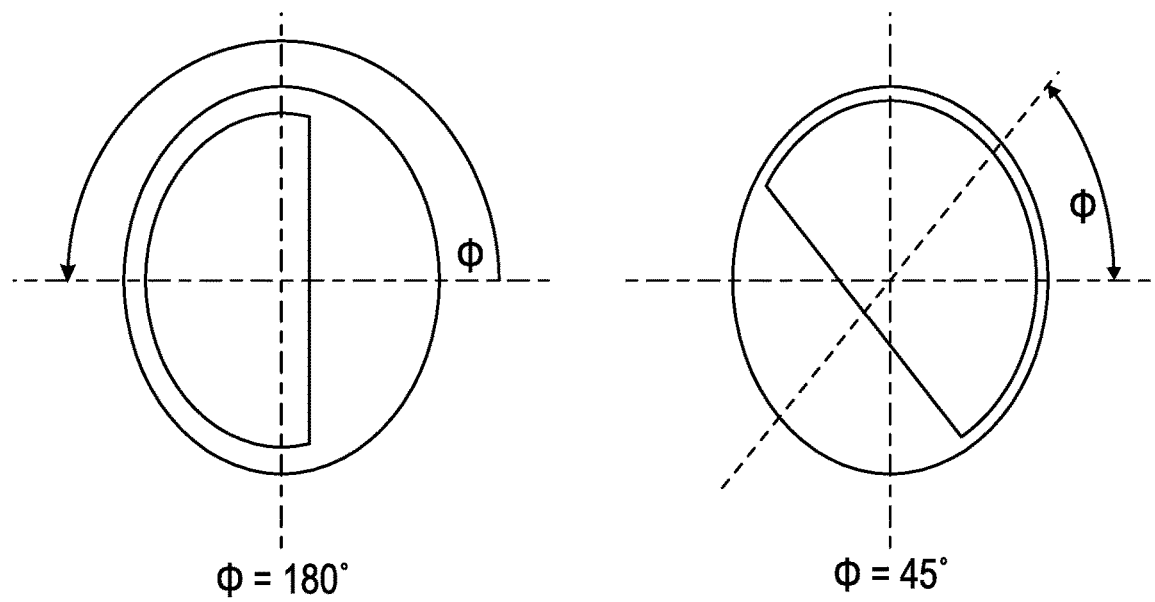
FIG. 34d schematically depicts a rotated view of cutting surfaces according to the present disclosure.

FIG. 34c provides 3D representations of three (3) of the aforementioned cutting element arrangements to establish the cutting surface in three dimensional spaces. Any of these aforementioned cutting surfaces can be rotated to establish different directional cutting capability as exemplified in FIG. 34d. A plethora of tips could be provided to the end user to enable the user to complete all desired cutting motions.

Variations of the cutting edge can increase or decrease the cutting capability of the leading edge.

FIG. 35 presents various manipulations to the cutting edge of the cutting element. These are generally classified as serrated cutting edges where multiple points of contact are introduced between the cutting edge and the tissue material. This can improve cutting function by improving the ease of use by the introduction of multiple lead cutting edges in the form of different shaped teeth. Configuration a) in the figure, presents a serrated square edge to break up the tissue into smaller pieces to streamline the collection process into the lumen of the cutting element. Configurations b) and c) display rounded serrated cutting edges. Lastly, Configuration d) in the figure depicts a triangular toothed serrated cutting edge. These variations can break up incoming tissue and prevent clogging of the device.

FIG. 36 presents a cutting tip element where there is a gradual reduction in tip diameter from the shaft to the cutting edge surface. This cutting element has a smaller diameter orifice that tapers into the larger shaft diameter. Any of the aforementioned modifications to the cutting element can be incorporated with a tapered transition. This can provide benefits for manufacturing and for concentrating the suction at the tip.

Figure 37:
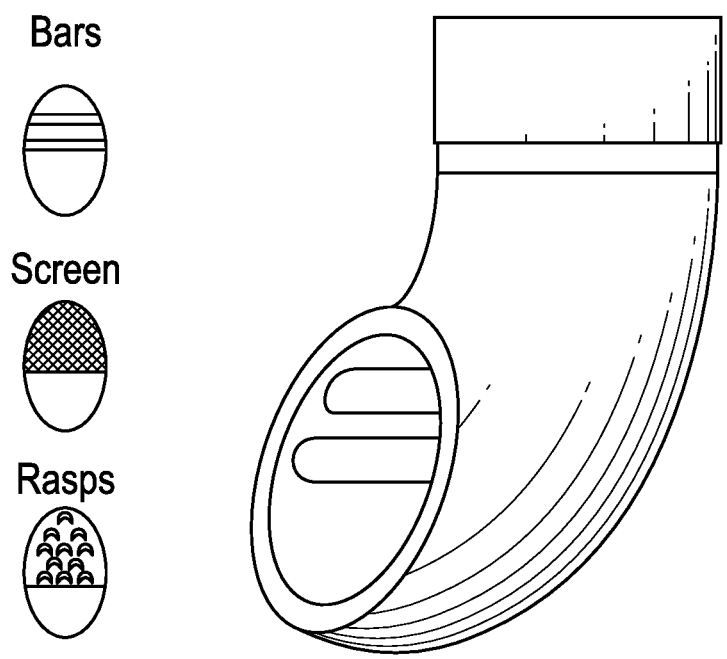
FIG. 37 schematically depicts a modified occlusion plate according to the present disclosure.

FIG. 37 presents a modified occlusion plate with the cutting element. These are alternate configurations that reduce the opening to the cutting element and control the size of tissue that enters the orifice. The introduction of at least one cross bar can restrict the size of tissue that enters the lumen of the cutting element. A screen can accomplish a similar function. The rasps are sharp cutting teeth on the occlusion surface to enable cutting or breaking up of tissue to occur with the actuation of this surface in addition to the cutting edge.

FIG. 38 depicts small rasp like cutting teeth that can be added as a feature to any aforementioned configuration of the cutting element. These teeth can break up additional tissue. The "blind rasps" are coarse features that would wrap around the outer surface of the cutting element. The "through-hole rasps" allow material to be cut and passed into the lumen of the cutting instrument.

Although advantageous features, functions and benefits of the disclosed devices, systems and methods have been described with reference to exemplary embodiments herein, the present disclosure is not limited by or to such exemplary embodiments.

The invention claimed is:

1. A tissue containment system, comprising:
   a. a suction canister that includes an internal reservoir, the suction canister including an outer wall and defining a longitudinal axis and an open end,
   b. a tissue containment insert removably received within the internal reservoir of the suction canister through the open end, the tissue containment insert including a discontinuous side wall that defines a gap or opening and that partially encloses a region for tissue collection and accumulation and including at least one extension finger extending axially from the discontinuous side wall to facilitate removal of the tissue containment insert from the suction canister, and
   c. a cap removably secured at the open end of the suction canister,
      wherein the at least one extension finger is positioned entirely within the suction canister when the cap is secured at the open end of the suction canister; and
      wherein, when the tissue containment insert is received within the suction canister, the gap or opening of the discontinuous side wall of the tissue containment insert overlaps with the outer wall of the suction canister so as to enclose the region for tissue collection and accumulation.

2. A tissue containment system of claim 1, further comprising means for manipulating tissue within the tissue containment insert, wherein the means for manipulating tissue includes a plunging mechanism that is linearly translatable relative to the suction canister.

3. A tissue containment system of claim 2, further comprising a delivery cannula assembled relative to the suction canister, and wherein the plunging mechanism is adapted to push tissue from the tissue containment insert into the delivery cannula.

4. A tissue containment system of claim 1, wherein the tissue containment insert is effective to maintain uninterrupted suction flow through the suction canister.

5. A tissue containment system of claim 1, wherein the tissue containment insert is effective to enable effective determination of the volume of tissue within the substantially enclosed region of the tissue containment insert.

6. A tissue containment system of claim 1, wherein the tissue containment insert includes a filter that defines a plurality of fine pores that are adapted to clog and restrict flow when the substantially enclosed region of the tissue containment insert reaches capacity.

7. A tissue containment system of claim 6, wherein the fine pores are calibrated to enable collection of cancellous bone and bone marrow within the substantially enclosed region of the tissue containment insert.

8. A tissue containment system of claim 1, wherein the tissue containment insert is modular and is adapted to establish a maximum tissue volume for receipt therewithin.

9. A tissue containment system of claim 1, wherein the tissue containment insert includes two or more perforated discs.

10. A tissue containment system of claim 9, wherein at least one of the two or more perforated discs is stationary relative to the suction canister and at least another of the two or more perforated discs is linearly translatable relative to the suction canister.

11. A tissue containment system of claim 10, wherein when spaced relative to each other, suction passes through the perforations of the stationary and linearly translatable discs, and wherein when the stationary and linearly translatable discs are in physical contact with each other, suction is_occluded from passing through the perforations of the stationary and linearly translatable discs.

12. A tissue containment system of claim 10, wherein as tissue enters the partially enclosed region of the tissue containment insert, the linearly translatable disc is adapted to be translated toward the stationary disc.

13. A tissue containment system of claim 2, wherein the means for manipulating tissue includes a manually actuable plunger.

14. A tissue containment system of claim 1, wherein the tissue containment insert is mounted with respect to the suction canister by at least one of screwing attachment, clip attachment, pin attachment and snap attachment.

15. A tissue containment system of claim 1, wherein the suction canister includes a window for viewing tissue content within the partially enclosed region of the tissue containment insert positioned within the internal reservoir.

16. A tissue containment system of claim 1, wherein the tissue containment insert defines one or more vent holes to permit suction to flow therethrough.

17. A tissue containment system of claim 1, wherein the tissue containment insert includes an internal structure that directs tissue to a side wall thereof.

18. A tissue containment system according to claim 1, wherein the at least one extension finger releasably secures the tissue containment insert relative to the suction canister.

19. A tissue containment system according to claim 1, wherein the at least one extension finger comprises a pair of spaced extension fingers.

20. A tissue containment system according to claim 1, wherein the tissue containment insert includes vent holes to enable vacuum to flow through the insert.

21. A tissue containment system according to claim 1, wherein the cap cooperates with the at least one extension finger to releasably secure the tissue containment insert in position within the internal reservoir.

22. A tissue containment system, comprising:
a. a suction canister that includes an internal reservoir, the suction canister including an outer wall and defining a longitudinal axis and an open end,
b. a tissue containment insert removably received within the internal reservoir of the suction canister, the tissue containment insert including a discontinuous side wall that defines a gap or opening that partially encloses a region for tissue collection and accumulation and including at least one extension finger extending axially from the discontinuous side wall to facilitate removal of the tissue containment insert from the suction canister, and
c. a cap removably secured at the open end of the suction canister,
wherein the at least one extension finger is positioned entirely within the suction canister when the cap is secured at the open end of the suction canister; and
wherein, when the tissue containment insert is received within the suction canister, the gap or opening of the discontinuous side wall of the tissue containment insert overlaps with the outer wall of the suction canister so as to enclose the region for tissue collection and accumulation.

* * * * *